United States Patent
Zhang

(10) Patent No.: US 7,037,911 B2
(45) Date of Patent: May 2, 2006

(54) AMINO-BICYCLIC PYRAZINONES AND PYRIDINONES AS COAGULATION SERINE PROTEASE INHIBITORS

(75) Inventor: Xiaojun Zhang, Hockessin, DE (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/465,538

(22) Filed: Jun. 19, 2003

(65) Prior Publication Data

US 2005/0038030 A1    Feb. 17, 2005

Related U.S. Application Data

(60) Provisional application No. 60/391,785, filed on Jun. 26, 2002.

(51) Int. Cl.
C07D 487/04    (2006.01)
A61K 31/407   (2006.01)
A61P 7/02      (2006.01)

(52) U.S. Cl. .................... 514/249; 544/349
(58) Field of Classification Search ........ 544/349; 514/249
See application file for complete search history.

(56) References Cited

U.S. PATENT DOCUMENTS

| | | | |
|---|---|---|---|
| 5,023,236 A | 6/1991 | Edgington et al. | |
| 5,843,442 A | 12/1998 | Soule et al. | |
| 5,859,010 A | 1/1999 | Petersen et al. | |
| 6,277,851 B1 | 8/2001 | De Nanteuil et al. | |
| 6,514,997 B1 | 2/2003 | Dragovich et al. | |
| 6,686,358 B1 * | 2/2004 | De Nanteuil et al. | 514/249 |
| 2001/0047006 A1 | 11/2001 | Dragovich et al. | |
| 2004/0006065 A1 | 1/2004 | Glunz | |

FOREIGN PATENT DOCUMENTS

| | | |
|---|---|---|
| WO | WO 95/35308 | 12/1995 |
| WO | WO 99/12034 | 3/1999 |
| WO | WO 01/64678 | 9/2001 |

OTHER PUBLICATIONS

Sanderson, P.E.J. et al., "Efficacious Orally Bioavailable Thrombin Inhibitors Based on 3-Aminopyridinone or 3-Aminopyrazinone Acetamide Peptidomimetic Templates", J. Med. Chem. vol. 41, pp. 4466-4474 (1998).

* cited by examiner

Primary Examiner—Bruck Kifle
(74) Attorney, Agent, or Firm—Jing G. Sum

(57) ABSTRACT

The present invention relates generally to compounds that inhibit serine proteases. In particular it is directed to novel amino-bicyclic pyrazinone and pyridinone compounds of Formula (I):

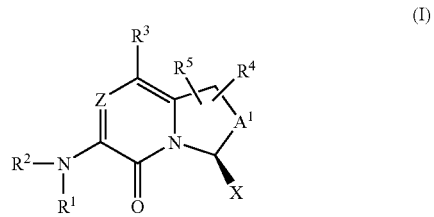

or a stereoisomer or pharmaceutically acceptable salt form thereof, which are useful as selective inhibitors of serine protease enzymes of the coagulation cascade; for example thrombin, factor Xa, factor XIa, factor IXa, and/or factor VIIa. In particular, it relates to compounds that are factor VIIa inhibitors. This invention also relates to pharmaceutical compositions comprising these compounds and methods of using the same.

25 Claims, No Drawings

AMINO-BICYCLIC PYRAZINONES AND PYRIDINONES AS COAGULATION SERINE PROTEASE INHIBITORS

CROSS-REFERENCE TO RELATED APPLICATIONS

The present application claims the priority benefit of U.S. Provisional Application No. 60/391,785, filed Jun. 26, 2002, which is expressly incorporated fully herein by reference.

FIELD OF THE INVENTION

The present invention relates generally to compounds that inhibit serine proteases. In particular it is directed to novel amino-bicyclic pyrazinone and pyridinone compounds of Formula (I):

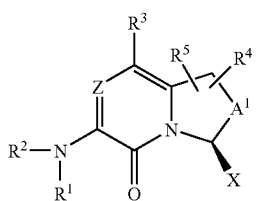

or a stereoisomer or pharmaceutically acceptable salt form thereof, which are useful as selective inhibitors of serine protease enzymes of the coagulation cascade; for example thrombin, factor Xa, factor XIa, factor IXa, and/or factor VIIa. In particular, it relates to compounds that are factor VIIa inhibitors. This invention also relates to pharmaceutical compositions comprising these compounds and methods of using the same.

BACKGROUND OF THE INVENTION

Factor VIIa is a plasma serine protease involved in the regulation of hemostasis. It binds with high affinity to Tissue Factor in the presence of calcium ions to form a complex. The complex exhibits enhanced proteolytic activity and is the primary initiator of the extrinsic pathway of blood coagulation. See Carson, S. D. and Brozna, J. P. *Blood Coag. Fibrinol.* 1993, 4, 281–292. The complex initiates blood coagulation by activating factor X to factor Xa, factor IX to factor IXa and additional factor VII to factor VIIa. Ultimately, the activity of factor VIIa induces the conversion of prothrombin to thrombin. Thrombin functions to convert fibrinogen to fibrin, which forms a clot through polymerization.

While blood coagulation is a necessary and important part in the regulation of an organism's hemostasis, blood coagulation can also have deleterious effects. For instance, thrombosis is the formation or presence of a blood clot inside a blood vessel or cavity of the heart. Such a blood clot can lodge in a blood vessel, blocking circulation and inducing a heart attack.

Because of the role of serine proteases in blood coagulation, researchers have postulated that the inhibition of factor VIIa could be used to treat or prevent disease states involving thrombosis. Work has accordingly been performed to identify and optimize factor VIIa inhibitors. For example, U.S. Pat. No. 5,859,010 discusses factor VIIa/Tissue Factor inhibitors that are dihydroxamates having a spacing from 0.37 nm to about 0.77 nm; U.S. Pat. No. 5,843,442 reports monoclonal-type antibodies or antibody fragments possessing inhibitory activity; and, U.S. Pat. No. 5,023,236 presents peptides and peptide derivatives that specifically inhibit the proteolytic active site of serine protease coagulation factor VII/VIIa.

In addition to the above, bicyclic pyridinones and pyrazinones are known in the art. For example, PCT International publication WO 01/64678 describes substituted bicyclic pyrazinones useful as inhibitors of the HCV NS3 protease. U.S. Patent Publication No. US2001047006 describes a generic scope of peptidyl compounds including, but not limited to, bicyclic pyridinones, useful as picornaviral 3C inhibitors. U.S. Pat. No. 6,277,851 describes a generic scope of bicyclic amino-pyrazinones, useful as inhibitors of trypsin-related serine proteases. PCT International publication WO 95/35308 describes a generic scope of compounds including, but not limited to, substituted bicyclic pyridinone compounds as peptide inhibitors of interleukin-1β converting enzyme. PCT International publication WO 99/12034 describes a generic scope of compounds including, but not limited to, substituted fully saturated bicyclic pyridinone compounds as useful pharmaceuticals. The scope of the above references is not considered to exemplify nor suggest the present invention.

While a number of factor VIIa inhibitors have been discussed in the art, improved inhibitors, especially non-peptide inhibitors, of serine proteases for the treatment of thromboembolic disorders are always desirable. The present invention discloses non-peptide serine protease inhibitors which are bicyclic pyrimidinones useful in the treatment of thromboembolic disorders.

In addition, it is also desirable to find new compounds with improved pharmacological characteristics compared with known serine protease inhibitors. For example, it is preferred to find new compounds with improved factor XIa inhibitory activity and selectivity for factor XIa versus other serine proteases. It is also desirable and preferable to find compounds with advantageous and improved characteristics in one or more of the following categories, but are not limited to: (a) pharmaceutical properties; (b) dosage requirements; (c) factors which decrease blood concentration peak-to-trough characteristics; (d) factors that increase the concentration of active drug at the receptor; (e) factors that decrease the liability for clinical drug-drug interactions; (f) factors that decrease the potential for adverse side-effects; and, (g) factors that improve manufacturing costs or feasibility.

SUMMARY OF THE INVENTION

Accordingly, the present invention provides novel bicyclic amino-bicyclic pyrazinone and pyridinone compounds, which are useful as selective inhibitors of serine protease enzymes, especially factor VIIa, and pharmaceutically acceptable salts or prodrugs thereof.

The present invention also provides pharmaceutical compositions comprising a pharmaceutically acceptable carrier and a therapeutically effective amount of at least one of the compounds of the present invention or a pharmaceutically acceptable salt or prodrug form thereof.

The present invention also provides a method for modulation of the coagulation cascade comprising administering to a host in need of such treatment a therapeutically effective amount of at least one of the compounds of the present invention or a pharmaceutically acceptable salt or prodrug form thereof.

The present invention also provides a method for treating thromboembolic disorders comprising administering to a host in need of such treatment a therapeutically effective amount of at least one of the compounds of the present invention or a pharmaceutically acceptable salt or prodrug form thereof.

The present invention also provides novel bicyclic amino-bicyclic pyrazinone and pyridinone compounds for use in therapy.

The present invention also provides the use of novel bicyclic pyrimidinone compounds for the manufacture of a medicament for the treatment of a thromboembolic disorder.

These and other embodiments, which will become apparent during the following detailed description, have been achieved by the inventors' discovery that the presently claimed novel bicyclic amino-bicyclic pyrazinone and pyridinone compounds, or pharmaceutically acceptable salt or prodrug forms thereof, are effective factor VIIa inhibitors.

DETAILED DESCRIPTION OF THE INVENTION

In a first aspect, the present invention provides, inter alia, compounds of Formula (I):

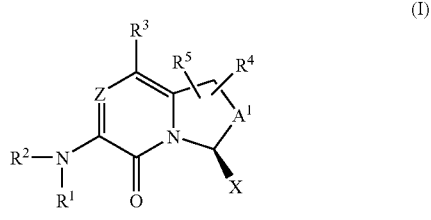

(I)

or a stereoisomer or pharmaceutically acceptable salt form thereof, wherein:

$A^1$ is —$CH_2$— or —$CH_2CH_2$—; wherein $A^1$ is optionally substituted with 0–2 $R^{14}$;

Z is CH or N;

X is —C(=O)NH—$(CR^{16}R^{16})_n$—$R^8$, —S(=O)$_2$NH—$(CR^{16}R^{16})_n$—$R^8$, —$CR^{15}R^{15}$—NHC(=O)—$(CR^{16}R^{16})_n$—$R^8$, —$CR^{15}R^{15}$—NHS(=O)$_2$—$(CR^{16}R^{16})_n$—$R^8$, or —$CR^{16}R^{16}$—NH—$R^8$;

n is 0, 1, or 2;

$R^1$ is selected from the group: H, $C_1$–$C_6$ alkyl substituted with 0–3 $R^{2b}$, $C_2$–$C_6$ alkenyl substituted with 0–3 $R^{2b}$, $C_2$–$C_6$ alkynyl substituted with 0–3 $R^{2b}$, $C_3$–$C_{10}$ carbocycle substituted with 0–3 $R^{2c}$, aryl substituted with 0–3 $R^{2c}$, and 5–10 membered heterocyclic group consisting of carbon atoms and 1–4 heteroatoms selected from the group: O, S, and N; and said 5–10 membered heterocyclic group is substituted with 0–3 $R^{2c}$;

$R^2$ is selected from the group: H, —C(=O)$R^{2a}$, —C(=O)O$R^{2a}$, —C(=O)N$R^{2a}R^{2a}$, —S(=O)$R^{2a}$, —S(=O)$_2R^{2a}$, —S(=O)$_2$N$R^{2a}R^{2a}$, —N$R^{2a}R^{2a}$, $C_1$–$C_6$ alkyl substituted with 0–3 $R^{2b}$, $C_2$–$C_6$ alkenyl substituted with 0–3 $R^{2b}$, $C_2$–$C_6$ alkynyl substituted with 0–3 $R^{2b}$, $C_3$–$C_{10}$ carbocycle substituted with 0–3 $R^{2c}$, aryl substituted with 0–3 $R^{2c}$, and 5–10 membered heterocyclic group consisting of carbon atoms and 1–4 heteroatoms selected from the group: O, S, and N; and said 5–10 membered heterocyclic group is substituted with 0–3 $R^{2c}$;

each $R^{2a}$ is, independently at each occurrence, H, $C_1$–$C_6$ alkyl substituted with 0–3 $R^{2b}$, $C_2$–$C_6$ alkenyl substituted with 0–3 $R^{2b}$, $C_2$–$C_6$ alkynyl substituted with 0–3 $R^{2b}$, $C_3$–$C_{10}$ carbocycle substituted with 0–3 $R^{2c}$, aryl substituted with 0–3 $R^{2c}$, or 5–10 membered heterocyclic group consisting of carbon atoms and 1–4 heteroatoms selected from the group: O, S, and N; and said 5–10 membered heterocyclic group is substituted with 0–3 $R^{2c}$;

provided when $R^2$ is —S(=O)$R^{2a}$ or —S(=O)$_2R^{2a}$, then $R^{2a}$ is not H;

each $R^{2b}$ is, independently at each occurrence, H, halogen, $NO_2$, CN, —NCS, =O, —CO$_2R^{21}$, —C(=O)N$R^{21}R^{21}$, —NHC(=O)$R^{21}$, —N$R^{21}R^{21}$, —NHSO$_2R^{21}$, —SO$_2R^{21}$, —SO$_2$N$R^{21}R^{21}$, —O$R^{21a}$, —S$R^{21a}$, —C(=O)$R^{21a}$, —S(=O)$R^{21a}$, $C_1$–$C_3$ alkyl, $C_1$–$C_4$ haloalkyl, $C_3$–$C_{10}$ carbocycle substituted with 0–3 $R^{2c}$, aryl substituted with 0–3 $R^{2c}$, or 5–10 membered heterocyclic group consisting of carbon atoms and 1–4 heteroatoms selected from the group: O, S, and N; and said 5–10 membered heterocyclic group is substituted with 0–3 $R^{2c}$;

each $R^{2c}$ is, independently at each occurrence, H, halogen, $NO_2$, CN, —NCS, =O, —CO$_2R^{21}$, —C(=O)N$R^{21}R^{21}$, —NHC(=O)$R^{21}$, —N$R^2$, $R^{21}$, —NHSO$_2R^{21}$, —SO$_2R^{21}$, —SO$_2$N$R^{21}R^{21}$, —O$R^{21a}$, —S$R^{21a}$, —C(=O)$R^{21a}$, —S(=O)$R^{21a}$, $C_1$–$C_4$ haloalkyl, $C_1$–$C_4$ alkyl substituted with 0–3 $R^{2d}$, $C_2$–$C_4$ alkenyl substituted with 0–3 $R^{2d}$, $C_2$–$C_4$ alkynyl substituted with 0–3 $R^{2d}$, $C_3$–$C_6$ carbocycle substituted with 0–3 $R^{2d}$, ($C_3$–$C_6$ carbocycle)$C_1$–$C_4$ alkyl-substituted with 0–3 $R^{2d}$, (aryl)$C_1$–$C_4$ alkyl-substituted with 0–5 $R^{2d}$, or 5–6 membered heterocyclic group consisting of carbon atoms and 1–4 heteroatoms selected from the group: O, S, and N; and said 5–6 membered heterocyclic group is substituted with 0–4 $R^{2d}$;

each $R^{2d}$ is, independently at each occurrence, H, halogen, $NO_2$, CN, —NCS, =O, OH, —CO$_2R^{21}$, —C(=O)N$R^{21}R^{21}$, —NHC(=O)$R^{21}$, —N$R^{21}R^{21}$, —NHSO$_2R^{21}$, —SO$_2R^{21}$, —SO$_2$N$R^{21}R^{21}$, —O$R^{21a}$, —S$R^{21a}$, —C(=O)$R^{21a}$, —S(=O)$R^{2a}$, $C_1$–$C_4$ alkyl, or $C_1$–$C_4$ haloalkyl;

alternatively, $R^1$ and $R^2$, when attached to the same nitrogen, combine to form a 5–6 membered heterocyclic ring consisting of one nitrogen atom, carbon atoms and 0–1 additional heteroatoms selected from the group consisting of —N($R^{24}$)—, O, and S;

$R^3$ is selected from the group: H, halogen, $NO_2$, CN, $CF_3$, OH, —SO$_2R^{3a}$, —C(=O)$R^{3a}$, —CO$_2R^{3a}$, —C(=O)N$R^{3a}R^{3a}$, —NHC(=O)$R^{3a}$, —N$R^{3a}R^{3a}$, $C_1$–$C_6$ alkyl substituted with 0–3 $R^{3b}$, $C_2$–$C_6$ alkenyl substituted with 0–3 $R^{3b}$, $C_2$–$C_6$ alkynyl substituted with 0–3 $R^{3b}$, $C_3$–$C_{10}$ carbocycle substituted with 0–3 $R^{3c}$, aryl substituted with 0–3 $R^{3c}$, and 5–10 membered heterocyclic group consisting of carbon atoms and 1–4 heteroatoms selected from the group: O, S, and N; and said 5–10 membered heterocyclic group is substituted with 0–3 $R^{3c}$;

each $R^{3a}$ is, independently at each occurrence, H, $C_1$–$C_6$ alkyl substituted with 0–3 $R^{3b}$, $C_2$–$C_6$ alkenyl substituted with 0–3 $R^{3b}$, $C_2$–$C_6$ alkynyl substituted with 0–3 $R^{3b}$, $C_3$–$C_{10}$ carbocycle substituted with 0–3 $R^{3c}$, aryl substituted with 0–3 $R^{3c}$, or 5–10 membered heterocyclic group consisting of carbon atoms and 1–4 heteroatoms selected from the group: O, S, and N; and said 5–10 membered heterocyclic group is substituted with 0–3 $R^{3c}$;

provided when $R^3$ is —SO$_2R^{3a}$, then $R^{3a}$ is not H;

each $R^{3b}$ is, independently at each occurrence, $C_3$–$C_{10}$ carbocycle substituted with 0–3 $R^{3c}$, aryl substituted with 0–3 $R^{3c}$, or 5–10 membered heterocyclic group consisting of carbon atoms and 1–4 heteroatoms selected from the group: O, S, and N; and said 5–10 membered heterocyclic group is substituted with 0–3 $R^{3c}$;

each $R^{3c}$ is, independently at each occurrence, H, F, Cl, Br, I, $NO_2$, CN, —NCS, =O, $NH_2$, —NH($C_1$–$C_4$ alkyl), —N(C$_1$–C$_4$ alkyl)$_2$, CO$_2$H, —CO$_2$(C$_1$–C$_4$ alkyl), —C(=O)NH$_2$, —C(=O)NH(C$_1$–C$_4$ alkyl), —C(=O)N(C$_1$–C$_4$ alkyl)$_2$, —NHC(=O)(C$_1$–C$_4$ alkyl), —NHSO$_2$(C$_1$–C$_4$ alkyl), —SO$_2$(C$_1$–C$_4$ alkyl), —SO$_2$NH$_2$, —SO$_2$NH(C$_1$–C$_4$ alkyl), —SO$_2$N(C$_1$–C$_4$ alkyl)$_2$, OH, —O(C$_1$–C$_4$ alkyl), —S(C$_1$–C$_4$ alkyl), —C(=O)H, —C(=O)(C$_1$–C$_4$ alkyl), —S(=O)(C$_1$–C$_4$ alkyl), C$_1$–C$_4$ alkyl, C$_1$–C$_4$ alkoxy, C$_1$–C$_4$ haloalkyl, or C$_1$–C$_4$ haloalkoxy;

R$^4$ is selected from the group: H, halogen, CF$_3$, —OCF$_3$, OH, CN, NO$_2$, —OR$^{22}$, —SR$^{22}$, —NR$^{22}$R$^{23}$, —C(=O)R$^{22}$, —C(=O)NR$^{22}$R$^{23}$, —NR$^{24}$C(=O)R$^{22}$, —NR$^{24}$C(=O)NR$^{22}$R$^{23}$, —NR$^{24}$C(=O)NR$^{24}$C(=O)R$^{22}$, —C(=O)OR$^{22}$, —OC(=O)R$^{22}$, —OC(=O)OR$^{22}$, —NR$^{24}$C(=O)OR$^{22}$, —OC(=O)NR$^{22}$R$^{23}$, —S(=O)R$^{22}$, —S(=O)$_2$R$^{22}$, —S(=O)NR$^{22}$R$^{23}$, —S(=O)$_2$NR$^{22}$R$^{23}$, —NR$^{24}$S(=O)$_2$NR$^{22}$R$^{23}$, —NR$^{24}$S(=O)R$^{22}$, —NR$^{24}$S(=O)$_2$R$^{22}$, C$_1$–C$_4$ haloalkyl, C$_1$–C$_8$ alkoxy, (C$_1$–C$_4$ haloalkyl)oxy, C$_1$–C$_8$ alkyl substituted with 0–3 R$^{4a}$, C$_2$–C$_8$ alkenyl substituted with 0–3 R$^{4a}$, C$_2$–C$_8$ alkynyl substituted with 0–3 R$^{4a}$, C$_3$–C$_{10}$ carbocycle substituted with 0–3 R$^{26}$, aryl substituted with 0–5 R$^{26}$, and 5–10 membered heterocycle containing from 1–4 heteroatoms selected from the group consisting of N, O, and S; said 5–10 membered heterocycle substituted with 0–3 R$^{27}$;

each R$^{4a}$ is, independently at each occurrence, H, halo, CF$_3$, —OCF$_3$, OH, CN, —NO$_2$, —OR$^{22}$, —SR$^{22}$, —NR$^{22}$R$^{23}$, —C(=O)R$^{22}$, —C(=O)NR$^{22}$R$^{23}$, —NR$^{24}$C(=O)R$^{22}$, —NR$^{24}$C(=O)NR$^{22}$R$^{23}$, —NR$^{24}$C(=O)NR$^{24}$(=O)R$^{22}$, —C(=O)OR$^{22}$, —OC(=O)R$^{22}$, —OC(=O)OR$^{22}$, —NR$^{24}$C(=O)OR$^{22}$, —OC(=O)NR$^{22}$R$^{23}$, —S(=O)R$^{22}$, —S(=O)$_2$R$^{22}$, —S(=O)NR$^{22}$R$^{23}$, —S(=O)$_2$NR$^{22}$R$^{23}$, —NR$^{24}$S(=O)$_2$NR$^{22}$R$^{23}$, —NR$^{24}$S(=O)R$^{22}$, —NR$^{24}$S(=O)$_2$R$^{22}$, C$_1$–C$_4$ haloalkyl, C$_1$–C$_8$ alkoxy, (C$_1$–C$_4$ haloalkyl)oxy, C$_3$–C$_{10}$ carbocycle substituted with 0–3 R$^{26}$, aryl substituted with 0–5 R$^{26}$, or 5–10 membered heterocycle containing from 1–4 heteroatoms selected from the group consisting of N, O, and S; said 5–10 membered heterocycle substituted with 0–3 R$^{27}$;

R$^5$ is selected from the group: H, halo, C$_1$–C$_4$ haloalkyl, C$_1$–C$_8$ alkyl substituted with 0–3 R$^{4a}$, C$_2$–C$_8$ alkenyl substituted with 0–3 R$^{4a}$, C$_2$–C$_8$ alkynyl substituted with 0–3 R$^{4a}$, C$_3$–C$_{10}$ carbocycle substituted with 0–3 R$^{26}$, aryl substituted with 0–5 R$^{26}$, and 5–10 membered heterocycle containing from 1–4 heteroatoms selected from the group consisting of N, O, and S; said 5–10 membered heterocycle substituted with 0–3 R$^{27}$;

alternatively, R$^4$ and R$^5$ may be joined together with the carbon atom to which they are attached to form C$_3$–C$_{10}$ carbocycle substituted with 0–3 R$^{26}$, or 5–10 membered heterocycle containing from 1–4 heteroatoms selected from the group consisting of N, O, and S; said 5–10 membered heterocycle substituted with 0–3 R$^{27}$;

R$^8$ is selected from the group: phenyl substituted with one R$^{8a}$ and 0–2 R$^{8b}$, 5–6 membered heteroaryl group comprising carbon atoms and 1, 2, or 3 heteroatoms selected from N, O, S, SO, and SO$_2$, wherein said 5–6 membered heteroaryl group is substituted with one R$^{8a}$ and 0–2 R$^{8b}$, 9–10 membered bicyclic carbocyclic group, wherein said 9–10 membered bicyclic carbocyclic group contains at least one aromatic ring, and said 9–10 membered bicyclic carbocyclic group is substituted with one R$^{8a}$ and 0–2 R$^{8b}$, and 9–10 membered bicyclic heterocyclic group comprising carbon atoms and 1, 2, or 3 heteroatoms selected from N, O, S, SO, and SO$_2$, wherein said 9–10 membered bicyclic heterocyclic group contains at least one aromatic ring, and said 9–10 membered bicyclic heterocyclic group is substituted with one R$^{8a}$ and 0–2 R$^{8b}$;

each R$^{8a}$ is, independently at each occurrence, C$_1$–C$_6$ alkyl, F, Cl, Br, I, OH, CF$_3$, —OCF$_3$, —OCH$_3$, —OCH$_2$CH$_3$, —OCH(CH$_3$)$_2$, —OCH$_2$CH$_2$CH$_3$, CN, NO$_2$, NH$_2$, —NH(C$_1$–C$_3$ alkyl), —N(C$_1$–C$_3$ alkyl)$_2$, —C(=NH)NH$_2$, —C(=O)NH$_2$, —CH$_2$NH$_2$, —CH$_2$NH(C$_1$–C$_3$ alkyl), —CH$_2$N(C$_1$–C$_3$ alkyl)$_2$, —CH$_2$CH$_2$NH$_2$, —CH$_2$CH$_2$NH(C$_1$–C$_3$ alkyl), —CH$_2$CH$_2$N(C$_1$–C$_3$ alkyl)$_2$, —(CR$^{18}$R$^{19}$)$_r$C(=NR$^{18}$)NR$^{17}$R$^{19}$, —(CR$^{18}$R$^{19}$)$_r$C(=NR$^{17}$)NR$^{18}$R$^{19}$, —(CR$^{18}$R$^{19}$)$_r$NHC(=NR$^{18}$)NR$^{17}$R$^{19}$, —(CR$^{18}$R$^{19}$)$_r$NHC(=NR$^{17}$)NR$^{18}$R$^{19}$, —(CR$^{18}$R$^{19}$)$_r$NR$^{17}$C(=NR$^{18}$)NR$^{18}$R$^{19}$, —(CR$^{18}$R$^{19}$)$_r$NR$^{18}$CH(=NR$^{17}$), —(CR$^{18}$R$^{19}$)$_r$NR$^{17}$CH(=NR$^{18}$), —(CR$^{18}$R$^{19}$)$_r$C(=O)H, —(CR$^{18}$R$^{19}$)$_r$C(=O)R$^{20}$, —(CR$^{18}$R$^{19}$)$_r$NR$^{18}$R$^{19}$, —(CR$^{19}$R$^{19}$)$_r$C(=O)NR$^{18}$R$^{19}$, —(CR$^{18}$R$^{19}$)$_r$NR$^{19}$C(=O)R$^{20}$, —(CR$^{18}$R$^{19}$)$_r$OR$^{20}$, —(CR$^{18}$R$^{19}$)$_r$S(=O)NR$^{18}$R$^{19}$, —(CR$^{18}$R$^{19}$)$_r$S(=O)$_2$NR$^{18}$R$^{19}$, —(CR$^{18}$R$^{19}$)$_r$NR$^{19}$S(=O)R$^{20}$, —(CR$^{18}$R$^{19}$)$_r$NR$^{19}$S(=O)$_2$R$^{20}$, —(CR$^{18}$R$^{19}$)$_r$SR$^{20}$, —(CR$^{18}$R$^{19}$)$_r$S(=O)R$^{20}$, or —(CR$^{18}$R$^{19}$)$_r$S(=O)$_2$R$^{20}$;

provided that the moiety S(=O)R$^{20}$ forms other than S(=O)H, and the moiety S(=O)$_2$R$^{20}$ forms other than S(=O)$_2$H;

each R$^{8b}$ is, independently at each occurrence, H, halogen, C$_1$–C$_4$ alkyl, C$_1$–C$_4$ alkoxy, OH, CF$_3$, —OCF$_3$, CN, NO$_2$, —C(=O)NH$_2$, NH$_2$, —NH(C$_1$–C$_3$ alkyl), or —N(C$_1$–C$_3$ alkyl)$_2$;

each R$^{14}$ is, independently at each occurrence, H, C$_1$–C$_6$ alkyl-, C$_2$–C$_6$ alkenyl-, C$_2$–C$_6$ alkynyl-, OH, C$_1$–C$_6$ alkoxy-, NH$_2$, (C$_1$–C$_3$ alkyl)HN—, (C$_1$–C$_3$ alkyl)$_2$N—, C$_2$–C$_6$ alkoxyalkyl-, C$_2$–C$_6$ alkylaminoalkyl-, or C$_3$–C$_6$ dialkylaminoalkyl-;

each R$^{15}$ is, independently at each occurrence, H, F, methyl, ethyl, or propyl;

alternatively, —CR$^{15}$R$^{15}$— forms a gem disubstituted cyclopropyl, cyclobutyl, cyclopentyl, or cyclohexyl group;

each R$^{16}$ is, independently at each occurrence, H, methyl, ethyl, propyl, butyl, phenyl, or benzyl;

each R$^{17}$ is, independently at each occurrence, H, OH, C$_1$–C$_6$ alkyl, —OR$^{17a}$, —C(=O)OR$^{17a}$, —OC(=O)R$^{17a}$, —OC(=O)OR$^{17a}$, —C(=O)R$^{17a}$, —CH$_2$C(=O)R$^{17a}$, —C(=O)SR$^{17a}$, —C(=S)OR$^{17a}$, —C(=S)SR$^{17a}$, phenyl, phenyl-NH$_2$—C(=O)—, phenyl-(C$_1$–C$_3$ alkyl)-, C$_1$–C$_6$ alkyl-NH$_2$—C(=O)—, C$_1$–C$_4$ alkyl-C(=O)O—(C$_1$–C$_4$ alkyl)-OC(=O)—, or aryl-C(=O)O—(C1—C$_4$ alkyl)-OC(=O)—;

each R$^{17a}$ is, independently at each occurrence, C$_1$–C$_6$ alkyl substituted with 0–3 R$^{17b}$, C$_2$–C$_6$ alkenyl substituted with 0–3 R$^{17b}$, C$_3$–C$_6$ alkynyl substituted with 0–3 R$^{17b}$, C$_3$–C$_8$ carbocycle substituted with 0–3 R$^{17b}$, C$_3$–C$_8$ carbocycle(C$_1$–C$_3$ alkyl)-substituted with 0–3 R$^{17b}$, aryl substituted with 0–3 R$^{17b}$, aryl(C$_1$–C$_3$ alkyl)-substituted with 0–3 R$^{17b}$, 5–6 membered heterocyclic group consisting of carbon atoms and 1–4 heteroatoms selected from the group: O, S, and N, and substituted with 0–3 R$^{17b}$, or 5–6 membered heterocyclic(C$_1$–C$_3$ alkyl) group consisting of carbon atoms and 1–4 heteroatoms selected from the group: O, S, and N, and substituted with 0–3 R$^{17b}$;

each R$^{17b}$ is, independently at each occurrence, H, halogen, CF$_3$, —OCF$_3$, C$_1$–C$_6$ alkyl, OH, C$_1$–C$_6$ alkoxy, CN, NO$_2$, NH$_2$, —N(CH$_3$)$_2$, CO$_2$H, —C(=O)O(C$_1$–C$_6$ alkyl), or —OC(=O)aryl;

each R$^{18}$ is, independently at each occurrence, H or C$_1$–C$_4$ alkyl;

alternatively, R$^{17}$ and R$^{18}$ combine to form —C(=O)OC(=O)—, —C(=O)O—, —C(=O)S—, or —C(=S)O—;

each R$^{19}$ is, independently at each occurrence, H or C$_1$–C$_4$ alkyl;

alternatively, $R^{18}$ and $R^{19}$, when attached to the same nitrogen, combine to form a 5–10 membered heterocyclic ring consisting of one nitrogen atom, carbon atoms and 0–2 additional heteroatoms selected from the group consisting of N, O, and S;

each $R^{20}$ is, independently at each occurrence, H or $C_1$–$C_6$ alkyl;

each $R^{21}$ is, independently at each occurrence, H, $C_1$–$C_4$ alkyl, aryl, or aryl($C_1$–$C_3$ alkyl)-;

each $R^{21a}$ is, independently at each occurrence, H, $C_1$–$C_4$ alkyl, aryl, aryl($C_1$–$C_3$ alkyl)-, or $C_1$–$C_4$ haloalkyl;

each $R^{22}$ is, independently at each occurrence, H, $C_1$–$C_8$ alkyl substituted with 0–3 $R^{25}$, $C_2$–$C_8$ alkenyl substituted with 0–3 $R^{25}$, $C_2$–$C_8$ alkynyl substituted with 0–3 $R^{25}$, $C_3$–$C_{10}$ carbocycle substituted with 0–3 $R^{26}$, aryl substituted with 0–5 $R^{26}$, or 5–10 membered heterocycle containing from 1–4 heteroatoms selected from the group consisting of N, O, and S; said 5–10 membered heterocycle substituted with 0–3 $R^{26}$;

provided when $R^4$ or $R^{4a}$ are —OC(=O)O$R^{22}$, —S(=O) $R^{22}$, —S(=O)$_2R^{22}$, —NR$^{24}$S(=O)$R^{22}$, or —NR$^{24}$S(=O)$_2$ $R^{22}$, then $R^{22}$ is not H;

each $R^{23}$ is, independently at each occurrence, H, $C_1$–$C_4$ alkyl, $C_2$–$C_4$ alkenyl, or $C_2$–$C_4$ alkynyl;

alternatively, $R^{22}$ and $R^{23}$, when attached to the same nitrogen, combine to form a 5–6 membered heterocyclic ring consisting of one nitrogen atom, carbon atoms and 0–1 additional heteroatoms selected from the group consisting of —N($R^{24}$)—, O, and S;

each $R^{24}$ is, independently at each occurrence, H or $C_1$–$C_4$ alkyl;

each $R^{25}$ is, independently at each occurrence, H, halo, $CF_3$, —OCF$_3$, OH, CN, NO$_2$, $C_1$–$C_4$ haloalkyl, $C_1$–$C_8$ alkoxy, ($C_1$–$C_4$ haloalkyl)oxy, $C_3$–$C_{10}$ carbocycle substituted with 0–3 $R^{26}$, aryl substituted with 0–5 $R^{26}$, or 5–10 membered heterocycle containing from 1–4 heteroatoms selected from the group consisting of N, O, and S; said 5–10 membered heterocycle substituted with 0–3 $R^{27}$;

each $R^{26}$ is, independently at each occurrence, H, OH, halo, CN, NO$_2$, CF$_3$, —SO$_2R^{28}$, —NR$^{29}R^{30}$, $C_1$–$C_6$ alkyl, $C_2$–$C_6$ alkenyl, $C_2$–$C_6$ alkynyl, $C_3$–$C_6$ cycloalkyl, $C_1$–$C_4$ haloalkyl, $C_1$–$C_4$ haloalkyloxy-, $C_1$–$C_4$ alkyloxy-, $C_1$–$C_4$ alkylthio-, $C_1$–$C_4$ alkyl-C(=O)—, or $C_1$–$C_4$ alkyl-C(=O) NH—;

each $R^{27}$ is, independently at each occurrence, H, OH, halo, CF$_3$, —SO$_2R^{28}$, —NR$^{29}R^{30}$, or $C_1$–$C_4$ alkyl;

each $R^{28}$ is, independently at each occurrence, $C_1$–$C_4$ alkyl, phenyl, or benzyl;

each $R^{29}$ is, independently at each occurrence, H, SO$_2R^{28}$, C(=O)$R^{28}$, $C_1$–$C_4$ alkyl, phenyl, or benzyl;

each $R^{30}$ is, independently at each occurrence, H or $C_1$–$C_4$ alkyl;

t, at each occurrence, is selected from 0, 1, 2, and 3;

provided when Z is N, X is —C(=O)NH—CH$_2$—$R^8$ or —C(=O)NH—CH$_2$CH$_2$—$R^8$, $R^8$ is phenyl, a 5–6 membered heteroaryl group, a 9–10 membered bicyclic carbocyclic group, or a 9–10 membered bicyclic heterocyclic group, $R^{8a}$ is $C_1$–$C_6$ alkyl, F, Cl, Br, I, OH, CF$_3$, —OCF$_3$, —OCH$_3$, —OCH$_2$CH$_3$, —OCH(CH$_3$)$_2$, —OCH$_2$CH$_2$CH$_3$, NH$_2$, —NH(C$_1$–C$_3$ alkyl), —N(C$_1$–C$_3$ alkyl)$_2$, —NR$^{18}R^{19}$, —(CR$^{18}R^{19}$)$_t$C(=O)NR$^{19}R^{19}$, or —(CR$^{18}R^{19}$)$_t$OR$^{20}$, and $R^{8b}$ is H, halogen, $C_1$–$C_4$ alkyl, $C_1$–$C_4$ alkoxy, OH, CF$_3$, —OCF$_3$, NH$_2$, —NH(C$_1$–C$_3$ alkyl), or —N(C$_1$–C$_3$ alkyl)$_2$, then one of $R^3$, $R^4$, or $R^5$, is not H; and provided when Z is N, X is —C(=O)NH—CH$_2$—$R^8$ or —C(=O)NH—CH$_2$CH$_2$—$R^8$, $R^8$ is phenyl or pyridyl, $R^{8a}$ is —C(=NH)NHOH or —C(=NOH)NH$_2$, and $R^{8b}$ is H or halogen, then one of $R^3$, $R^4$, or $R^5$, is not H.

In a second aspect, the present invention includes compounds of Formula (I) or a stereoisomer or pharmaceutically acceptable salt form thereof, wherein:

$A^1$ is —CH$_2$— or —CH$_2$CH$_2$—;

$R^1$ is H or $C_1$–$C_6$ alkyl;

$R^3$ is selected from the group: H, halogen, NO$_2$, CN, CF$_3$, OH, —SO$_2R^{3a}$, —C(=O)$R^{3a}$, —CO$_2R^{3a}$, —C(=O) NR$^{3a}R^{3a}$, —NHC(=O)$R^{3a}$, —NR$^{3a}R^{3a}$, $C_1$–$C_6$ alkyl substituted with 0–1 $R^{3b}$, $C_2$–$C_6$ alkenyl substituted with 0–1 $R^{3b}$, $C_2$–$C_6$ alkynyl substituted with 0–1 $R^{3b}$, $C_3$–$C_6$ carbocycle substituted with 0–3 $R^{3c}$, aryl substituted with 0–3 $R^{3c}$, and 5–6 membered heterocyclic group consisting of carbon atoms and 1–4 heteroatoms selected from the group: O, S, and N; and said 5–6 membered heterocyclic group is substituted with 0–3 $R^{3c}$;

each $R^{3a}$ is, independently at each occurrence, H, $C_1$–$C_6$ alkyl substituted with 0–1 $R^{3b}$, $C_2$–$C_6$ alkenyl substituted with 0–1 $R^{3b}$, $C_2$–$C_6$ alkynyl substituted with 0–1 $R^{3b}$, $C_3$–$C_6$ carbocycle substituted with 0–3 $R^{3c}$, aryl substituted with 0–3 $R^{3c}$, or 5–6 membered heterocyclic group consisting of carbon atoms and 1–4 heteroatoms selected from the group: O, S, and N; and said 5–6 membered heterocyclic group is substituted with 0–3 $R^{3c}$;

provided when $R^3$ is —SO$_2R^{3a}$, then $R^{3a}$ is not H;

each $R^{3b}$ is, independently at each occurrence, $C_3$–$C_6$ carbocycle substituted with 0–3 $R^{3c}$, aryl substituted with 0–3 $R^{3c}$, and 5–6 membered heterocyclic group consisting of carbon atoms and 1–4 heteroatoms selected from the group: O, S, and N; and said 5–6 membered heterocyclic group is substituted with 0–3 $R^{3c}$;

$R^4$ is selected from the group: H, halogen, CF$_3$, —OCF$_3$, OH, CN, NO$_2$, —OR$^{22}$, —SR$^{22}$, —NR$^{22}R^{23}$, —C(=O)$R^{22}$, —C(=O)NR$^{22}R^{23}$, —NR$^{24}$C(=O)$R^{22}$, —NR$^{24}$C(=O) NR$^{22}R^{23}$, —NR$^{24}$C(=O)NR$^{24}$C(=O)$R^{22}$, —C(=O)O$R^{22}$, —OC(=O)$R^{22}$, —OC(=O)O$R^{22}$, —NR$^{24}$C(=O)O$R^{22}$, —OC(=O)NR$^{22}R^{23}$, —S(=O)$R^{22}$, —S(=O)$_2R^{22}$, —S(=O)NR$^{22}R^{23}$, —S(=O)$_2$NR$^{22}R^{23}$, —NR$^{24}$S(=O)$_2$ NR$^{22}R^{23}$, —NR$^{24}$S(=O)$R^{22}$, —NR$^{24}$S(=O)$_2R^{22}$, $C_1$–$C_4$ haloalkyl, $C_1$–$C_8$ alkoxy, ($C_1$–$C_4$ haloalkyl)oxy, $C_1$–$C_8$ alkyl substituted with 0–2 $R^{4a}$, $C_2$–$C_8$ alkenyl substituted with 0–2 $R^{4a}$, $C_2$–$C_8$ alkynyl substituted with 0–2 $R^{4a}$, $C_3$–$C_{10}$ carbocycle substituted with 0–3 $R^{26}$, aryl substituted with 0–5 $R^{26}$, and 5–10 membered heterocycle containing from 1–4 heteroatoms selected from the group consisting of N, O, and S; said 5–10 membered heterocycle substituted with 0–3 $R^{27}$;

each $R^{4a}$ is, independently at each occurrence, H, halo, CF$_3$, —OCF$_3$, OH, CN, NO$_2$, —OR$^{22}$, —SR$^{22}$, —NR$^{22}R^{23}$, —C(=O)$R^{22}$, —C(=O)NR$^{22}R^{23}$, —NR$^{24}$C(=O)$R^{22}$, —NR$^{24}$C(=O)NR$^{22}R^{23}$, —NR$^{24}$C(=O)NR$^{24}$C(=O)$R^{22}$, —C(=O)O$R^{22}$, —OC(=O)$R^{22}$, —OC(=O)O$R^{22}$, —NR$^{24}$C(=O)O$R^{22}$, —OC(=O)NR$^{22}R^{23}$, —S(=O)$R^{22}$, —S(=O)$_2R^{22}$, —S(=O)NR$^{22}R^{23}$, —S(=O)$_2$NR$^{22}R^{23}$, —NR$^{24}$S(=O)$_2$NR$^{22}R^{23}$, —NR$^{24}$S(=O)$R^{22}$, —NR$^{24}$S (=O)$_2R^{22}$, $C_1$–$C_4$ haloalkyl, $C_1$–$C_8$ alkoxy, ($C_1$–$C_4$ haloalkyl)oxy, $C_3$–$C_{10}$ carbocycle substituted with 0–3 $R^{26}$, aryl substituted with 0–5 $R^{26}$, and 5–10 membered heterocycle containing from 1–4 heteroatoms selected from the group consisting of N, O, and S; said 5–10 membered heterocycle substituted with 0–3 $R^{27}$;

$R^5$ is selected from the group: H, halo, $C_1$–$C_4$ haloalkyl, $C_1$–$C_4$ alkyl, $C_2$–$C_4$ alkenyl, and $C_2$–$C_4$ alkynyl;

$R^8$ is selected from the group: phenyl substituted with one $R^{8a}$ and 0–1 $R^{8b}$, pyridyl substituted with one $R^{8a}$ and 0–1 $R^{8b}$, naphthyl substituted with one $R^{8a}$ and 0–1 $R^{8b}$, quinolinyl substituted with one $R^{8a}$ and 0–1 $R^{8b}$, isoquinolinyl substituted with one $R^{8a}$ and 0–1 $R^{8b}$, phthalazinyl substituted with one $R^{8a}$ and 0–1 $R^{8b}$, quinazolinyl substituted with one $R^{8a}$ and 0–1 $R^{8b}$, indolyl substituted with one $R^{8a}$ and 0–1 $R^{8b}$, isoindolyl substituted with one $R^{8a}$ and 0–1 $R^{8b}$, indolinyl substituted with one $R^{8a}$ and 0–1 $R^{8b}$, 1H-indazolyl substituted with one $R^{8a}$ and 0–1 $R^{8b}$, and benzimidazolyl substituted with one $R^{8a}$ and 0–1 $R^{8b}$;

each $R^{17}$ is, independently at each occurrence, H, OH, $C_1$–$C_6$ alkyl, $C_1$–$C_6$ alkyl-O—, $C_1$–$C_6$ alkyl-C(=O)—, $C_1$–$C_4$ alkyl-OC(=O)—, aryl-O—, aryl-OC(=O)—, aryl-CH$_2$—C(=O)—, phenyl, phenyl-($C_1$–$C_3$ alkyl)-, $C_1$–$C_4$ alkyl-C(=O)O—($C_1$–$C_4$ alkyl)-OC(=O)—, aryl-C(=O)O—($C_1$–$C_4$ alkyl)-OC(=O)—, $C_1$–$C_6$ alkyl-NH$_2$—C(=O)—, or phenyl-NH$_2$—C(=O)—;

each $R^{18}$ is, independently at each occurrence, H or $C_1$–$C_4$ alkyl;

each $R^{19}$ is, independently at each occurrence, H or $C_1$–$C_4$ alkyl;

alternatively, $R^{18}$ and $R^{19}$, when attached to the same nitrogen, combine to form a 5–10 membered heterocyclic ring consisting of one nitrogen atom, carbon atoms and 0–2 additional heteroatoms selected from the group consisting of N, O, and S; and t, at each occurrence, is selected from 0, 1, and 2.

In a third aspect, the present invention includes compounds of Formula (Ia):

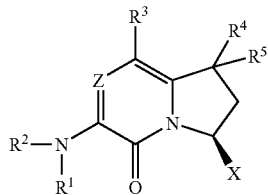

(Ia)

or a stereoisomer or pharmaceutically acceptable salt form thereof, wherein:

X is —C(=O)NH—CH$_2$—$R^8$, —S(=O)$_2$NH—CH$_2$—$R^8$, —CR$^{15}$R$^{15}$—NHC(=O)—CH$_2$—$R^8$, or —CR$^{15}$R$^{15}$—NHS(=O)$_2$—CH$_2$—$R^8$;

Z is CH or N;

$R^1$ is H, methyl, ethyl, propyl, or butyl;

$R^2$ is H, —C(=O)$R^{2a}$, —C(=O)O$R^{2a}$, —C(=O)NHR$^{2a}$, —S(=O)$R^{2a}$, —S(=O)$_2$R$^{2a}$, —S(=O)$_2$NHR$^{2a}$, $C_1$–$C_6$ alkyl substituted with 0–3 $R^{2b}$, $C_2$–$C_6$ alkenyl substituted with 0–3 $R^{2b}$, $C_2$–$C_6$ alkynyl substituted with 0–3 $R^{2b}$, $C_3$–$C_6$ carbocycle substituted with 0–3 $R^{2c}$, aryl substituted with 0–3 $R^{2c}$, or 5–6 membered heterocycle consisting of carbon atoms and 1–4 heteroatoms selected from the group: O, S, and N, and substituted with 0–3 $R^{2c}$;

each $R^{2a}$ is, independently at each occurrence, H, $C_1$–$C_6$ alkyl substituted with 0–2 $R^{2b}$, $C_2$–$C_6$ alkenyl substituted with 0–2 $R^{2b}$, $C_2$–$C_6$ alkynyl substituted with 0–2 $R^{2b}$, $C_3$–$C_6$ carbocycle substituted with 0–3 $R^{2c}$, aryl substituted with 0–3 $R^{2c}$, or 5–6 membered heterocyclic group consisting of carbon atoms and 1–4 heteroatoms selected from the group: O, S, and N; and said 5–6 membered heterocyclic group is substituted with 0–3 $R^{2c}$;

provided when $R^2$ is —S(=O)$R^{2a}$ or —S(=O)$_2$R$^{2a}$, then $R^{2a}$ is not H;

each $R^{2b}$ is, independently at each occurrence, H, F, Cl, Br, I, NO$_2$, CN, —NCS, CF$_3$, —OCF$_3$, CH$_3$, —CH$_2$CH$_3$, —OCH$_3$, =O, OH, CO$_2$H, NH$_2$, —NH(CH$_3$), N(CH$_3$)$_2$, CO$_2$R$^{21}$, —C(=O)NR$^2$, R$^{21}$, —NHC(=O)R$^{21}$, —NR$^{21}$R$^{21}$, —NHSO$_2$R$^{21}$, —SO$_2$R$^{21}$, —SO$_2$NR$^2$, R$^{21}$, —OR$^{21a}$, —SR$^{21a}$, —C(=O)R$^{21a}$, —S(=O)R$^{21a}$, $C_1$–$C_4$ haloalkyl, $C_1$–$C_4$ haloalkoxy, $C_3$–$C_6$ carbocycle substituted with 0–3 $R^{2c}$, aryl substituted with 0–3 $R^{2c}$, or 5–6 membered heterocycle consisting of carbon atoms and 1–4 heteroatoms selected from the group: O, S, and N, and substituted with 0–3 $R^{2c}$;

each $R^{2c}$ is, independently at each occurrence, H, F, Cl, Br, I, NO$_2$, CN, —NCS, CF$_3$, —OCF$_3$, CH$_3$, —OCH$_3$, =O, OH, CO$_2$H, NH$_2$, NH(CH$_3$), N(CH$_3$)$_2$, CO$_2$R$^{21}$, —C(=O)NR$^{21}$R$^{21}$, —NHC(=O)R$^{21}$, —NR$^2$, R$^{21}$, —NHSO$_2$R$^{21}$, —SO$_2$R$^{21}$, —SO$_2$NR$^2$, R$^{21}$, —OR$^{21a}$, —SR$^{21a}$, —C(=O)R$^{21a}$, —S(=O)R$^{21a}$, $C_1$–$C_4$ haloalkyl, $C_1$–$C_4$ haloalkoxy, or $C_1$–$C_4$ alkyl;

$R^3$ is selected from the group: H, Cl, Br, NO$_2$, CN, CF$_3$, $C_1$–$C_4$ alkyl, OH, CO$_2$H, —CO$_2$($C_1$–$C_4$ alkyl), NH$_2$, —NH($C_1$–$C_4$ alkyl), —N($C_1$–$C_4$ alkyl)$_2$, —C(=O)NH$_2$, —C(=O)NH($C_1$–$C_4$ alkyl), —C(=O)N($C_1$–$C_4$ alkyl)$_2$, —SO$_2$($C_1$–$C_4$ alkyl), —NHC(=O)H, —NHC(=O)($C_1$–$C_4$ alkyl), —C(=O)H, and —C(=O)($C_1$–$C_4$ alkyl);

$R^4$ is selected from the group: H, halogen, CF$_3$, —OCF$_3$, OH, CN, NO$_2$, —OR$^{22}$, —SR$^{22}$, —NR$^{22}$R$^{23}$, —C(=O)R$^{22}$, —C(=O)NR$^{22}$R$^{23}$, —NR$^{24}$C(=O)R$^{22}$, —NR$^{24}$C(=O)NR$^{22}$R$^{23}$, —NR$^{24}$C(=O)NR$^{24}$C(=O)R$^{22}$, —C(=O)OR$^{22}$, —OC(=O)R$^{22}$, —OC(=O)OR$^{22}$, —NR$^{24}$C(=O)OR$^{22}$, —OC(=O)NR$^{22}$R$^{23}$, —S(=O)R$^{22}$, —S(=O)$_2$R$^{22}$, —S(=O)NR$^{22}$R$^{23}$, —S(=O)$_2$NR$^{22}$R$^{23}$, —NR$^{24}$S(=O)$_2$NR$^{22}$R$^{23}$, —NR$^{24}$S(=O)R$^{22}$, —NR$^{24}$S(=O)$_2$R$^{22}$, $C_1$–$C_4$ haloalkyl, $C_1$–$C_6$ alkoxy, ($C_1$–$C_4$ haloalkyl)oxy, $C_1$–$C_6$ alkyl, $C_2$–$C_6$ alkenyl, $C_2$–$C_6$ alkynyl, and $C_1$–$C_4$ alkyl substituted with $R^{4a}$;

$R^{4a}$ is selected from the group: —NR$^{22}$R$^{23}$, —C(=O)NR$^{22}$R$^{23}$, —NR$^{24}$C(=O)R$^{22}$, —NR$^{24}$C(=O)NR$^{22}$R$^{23}$, —NR$^{24}$C(=O)NR$^{24}$C(=O)R$^{22}$, —C(=O)OR$^{22}$, —NR$^{24}$C(=O)OR$^{22}$, —NR$^{24}$S(=O)$_2$NR$^{22}$R$^{23}$, —NR$^{24}$S(=O)$_2$R$^{22}$, OH, and phenyl substituted with 0–2 $R^{26}$;

$R^8$ is phenyl substituted with one $R^{8a}$ and 0–1 $R^{8b}$, pyridyl substituted with one $R^{8a}$ and 0–1 $R^{8b}$, naphthyl substituted with one $R^{8a}$ and 0–1 $R^{8b}$, quinolinyl substituted with one $R^{8a}$ and 0–1 $R^{8b}$, or isoquinolinyl substituted with one $R^{8a}$ and 0–1 $R^{8b}$;

each $R^{8a}$ is, independently at each occurrence, —C(=NH)NH$_2$, —C(=O)NH$_2$, —NHC(=NH)NH$_2$, —NHCH(=NH), NH$_2$, —CH$_2$C(=NH)NH$_2$, —CH$_2$NHC(=NH)NH$_2$, —CH$_2$NHCH(=NH), —CH$_2$NH$_2$, or —CH$_2$C(=O)NH$_2$;

each $R^{15}$ is, independently at each occurrence, H, F, or methyl;

alternatively, —CR$^{15}$R$^{15}$— forms a gem disubstituted cyclopropyl group;

each $R^{21}$ is, independently at each occurrence, H, $C_1$–$C_4$ alkyl, aryl, or aryl($C_1$–$C_3$ alkyl)-;

each $R^{22}$ is, independently at each occurrence, H, $C_1$–$C_4$ alkyl, $C_2$–$C_4$ alkenyl, $C_3$–$C_6$ cycloalkyl, phenyl substituted with 0–5 $R^{26}$, benzyl substituted with 0–5 $R^{26}$, or 5–6 membered heterocycle containing from 1–4 heteroatoms selected from the group consisting of N, O, and S, and substituted with 0–3 $R^{26}$;

provided when $R^4$ or $R^{4a}$ are —OC(=O)OR$^{22}$, —S(=O)R$^{22}$, —S(=O)$_2$R$^{22}$, —NR$^{24}$S(=O)R$^{22}$, or —NR$^{24}$S(=O)$_2$R$^{22}$, then $R^{22}$ is not H;

each $R^{23}$ is, independently at each occurrence, H or $C_1$–$C_4$ alkyl;

alternatively, $R^{22}$ and $R^{23}$, when attached to the same nitrogen, combine to form a 5–6 membered heterocycle consisting of one nitrogen atom, carbon atoms and 0–1 additional heteroatoms selected from the group consisting of —N($R^{24}$)— and O; and each $R^{26}$ is, independently at each occurrence, H, OH, F, Cl, CN, $NO_2$, $CF_3$, —$SO_2CH_3$, —$SO_2CH_2CH_3$, $NH_2$, $NH(CH_3)$, $N(CH_3)_2$, methyl, ethyl, propyl, allyl, —$OCF_3$, methoxy, ethoxy, —$SCH_3$, —$SCH_2CH_3$, —C(=O)$CH_3$, —C(=O)$CH_2CH_3$, —NHC(=O)$CH_3$, or —NHC(=O)$CH_2CH_3$.

In a fourth aspect, the present invention includes compounds of Formula (Ib)

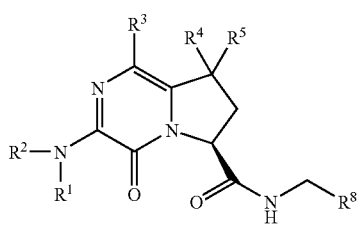

(Ib)

or a stereoisomer or pharmaceutically acceptable salt form thereof, wherein:

$R^1$ is H, methyl, or ethyl;

$R^2$ is H, —C(=O)$R^{2a}$, —C(=O)O$R^{2a}$, —S(=O)$_2R^{2a}$, —$NR^{2a}R^{2a}$, $C_1$–$C_6$ alkyl substituted with 0–1 $R^{2b}$, $C_2$–$C_6$ alkenyl substituted with 0–1 $R^{2b}$, $C_2$–$C_6$ alkynyl substituted with 0–1 $R^{2b}$, $C_3$–$C_6$ carbocycle substituted with 0–3 $R^{2c}$, aryl substituted with 0–3 $R^{2c}$, or 5–6 membered heterocycle consisting of carbon atoms and 1–4 heteroatoms selected from the group: O, S, and N, and substituted with 0–3 $R^{2c}$;

each $R^{2a}$ is, independently at each occurrence, H, $C_1$–$C_6$ alkyl substituted with 0–1 $R^{2b}$, $C_2$–$C_6$ alkenyl substituted with 0–1 $R^{2b}$, $C_2$–$C_6$ alkynyl substituted with 0–1 $R^{2b}$, $C_3$–$C_6$ carbocycle substituted with 0–3 $R^{2c}$, aryl substituted with 0–3 $R^{2c}$, or 5–6 membered heterocycle consisting of carbon atoms and 1–4 heteroatoms selected from the group: O, S, and N, and substituted with 0–3 $R^{2c}$;

provided when $R^2$ is —S(=O)$R^{2a}$ or —S(=O)$_2R^{2a}$, then $R^{2a}$ is not H;

each $R^{2b}$ is, independently at each occurrence, H, F, Cl, Br, I, $NO_2$, CN, —NCS, $CF_3$, —$OCF_3$, —$SCH_3$, —$SCH_2CH_3$, —$SCF_3$, $CH_3$, —$CH_2CH_3$, —CH($CH_3$)$_2$, —$OCH_3$, —$OCH_2CH_3$, =O, OH, $CO_2H$, $NH_2$, $NH(CH_3)$, $N(CH_3)_2$, —$NH(CH_2CH_3)$, —$N(CH_2CH_3)_2$, $CO_2H$, —$CO_2CH_3$, —$CO_2CH_2CH_3$, —C(=O)H, —C(=O)$CH_3$, —C(=O)$CH_2CH_3$, —C(=O)$CF_3$, —S(=O)$CH_3$, —S(=O)$CH_2CH_3$, —C(=O)$NH_2$, —C(=O)$NH(CH_3)$, —C(=O)$NH(CH_2CH_3)$, —C(=O)$N(CH_3)_2$, —C(=O)N($CH_2CH_3$)$_2$, —NHC(=O)H, —NHC(=O)$CH_3$, —NHC(=O)$CH_2CH_3$, —$NHSO_2(CH_3)$, —$NHSO_2(CH_2CH_3)$, —$SO_2CH_3$, —$SO_2CH_2CH_3$, —$SO_2NH_2$, —$SO_2NH(CH_3)$, —$SO_2NH(CH_2CH_3)$, $C_3$–$C_6$ carbocycle substituted with 0–3 $R^{2c}$, aryl substituted with 0–3 $R^{2c}$, or 5–6 membered heterocycle consisting of carbon atoms and 1–4 heteroatoms selected from the group: O, S, and N, and is substituted with 0–3 $R^{2c}$;

each $R^{2c}$ is, independently at each occurrence, H, F, Cl, $NO_2$, CN, $CF_3$, $CH_3$, —$CH_2CH_3$, —$CH_2CH_2CH_3$, —CH($CH_3$)$_2$, —$CH_2CH_2CH_2CH_3$, —CH($CH_3$)$CH_2CH_3$, —$CH_2CH(CH_3)_2$, —C($CH_3$)$_3$, $NH_2$, $NH(CH_3)$, $N(CH_3)_2$, —$NH(CH_2CH_3)$, —$N(CH_2CH_3)_2$, $CO_2H$, —$CO_2CH_3$, —$CO_2CH_2CH_3$, —C(=O)$NH_2$, —C(=O)$NH(CH_3)$, —C(=O)$NH(CH_2CH_3)$, —C(=O)$N(CH_3)_2$, —C(=O)N($CH_2CH_3$)$_2$, —NHC(=O)H, —NHC(=O)$CH_3$, —NHC(=O)$CH_2CH_3$, —$NHSO_2(CH_3)$, —$NHSO_2(CH_2CH_3)$, —$SO_2CH_3$, —$SO_2CH_2CH_3$, —$SO_2NH_2$, —$SO_2NH(CH_3)$, —$SO_2NH(CH_2CH_3)$, OH, —$OCH_3$, —$OCH_2CH_3$, —$OCF_3$, —$SCH_3$, —$SCH_2CH_3$, —$SCF_3$, —C(=O)H, —C(=O)$CH_3$, —C(=O)$CH_2CH_3$, —C(=O)$CF_3$, —S(=O)$CH_3$, or —S(=O)$CH_2CH_3$;

$R^3$ is selected from the group: H, Cl, Br, $NO_2$, CN, $CF_3$, $CH_3$, —$CH_2CH_3$, —$CH_2CH_2CH_3$, —CH($CH_3$)$_2$, —$CH_2CH_2CH_2CH_3$, —CH($CH_3$)$CH_2CH_3$, —$CH_2CH(CH_3)_2$, —C($CH_3$)$_3$, OH, $CO_2H$, —$CO_2CH_3$, —$CO_2CH_2CH_3$, $NH_2$, $NH(CH_3)$, $N(CH_3)_2$, —$NH(CH_2CH_3)$, —$N(CH_2CH_3)_2$, —C(=O)$NH_2$, —C(=O)$NH(CH_3)$, —C(=O)$NH(CH_2CH_3)$, —C(=O)$N(CH_3)_2$, —C(=O)N($CH_2CH_3$)$_2$, —NHC(=O)H, —NHC(=O)$CH_3$, —NHC(=O)$CH_2CH_3$, —$SO_2CH_3$, —$SO_2CH_2CH_3$, —C(=O)H, —C(=O)$CH_3$, or —C(=O)$CH_2CH_3$;

$R^4$ is H, F, Cl, Br, $CF_3$, $C_2$–$C_4$ haloalkyl, $C_1$–$C_6$ alkyl, $C_2$–$C_6$ alkenyl, $C_2$–$C_6$ alkynyl, —$NR^{22}R^{23}$, —$NR^{24}$C(=O)$R^{22}$, —$CH_2NR^{22}R^{23}$, —$CH_2$C(=O)$NR^{22}R^{23}$, —$CH_2NR^{24}$C(=O)$R^{22}$, —$CH_2NR^{24}$C(=O)$NR^{22}R^{23}$, —$CH_2$C(=O)O$R^{22}$, —$CH_2NR^{24}$C(=O)O$R^{22}$, —$CH_2NR^{24}$S(=O)$_2NR^{22}R^{23}$, —$CH_2NR^{24}$S(=O)$_2R^{22}$, —$C_1$–$C_4$ alkyl-(OH), or —$C_1$–$C_4$ alkyl-(aryl);

$R^5$ is H, methyl, ethyl, propyl, butyl, or allyl;

$R^8$ is phenyl substituted with —C(=NH)$NH_2$ and 0–1 $R^{8b}$;

$R^{8b}$ is H, F, Cl, Br, $CH_3$, —$OCH_3$, OH, $CF_3$, —$OCF_3$, CN, $NO_2$, —C(=O)$NH_2$, $NH_2$, $NH(CH_3)$, or $N(CH_3)_2$;

each $R^{22}$ is independently at each occurrence, H, methyl, ethyl, propyl, butyl, allyl, cyclopropyl, cyclobutyl, cyclopentyl, cyclohexyl, phenyl, pyridinyl, furanyl, thienyl, pyrrolyl, pyrazolyl, pyrazinyl, piperazinyl, piperidinyl, imidazolyl, imidazolidinyl, isoxazolyl, morpholinyl, oxazolyl, oxazolidinyl, or tetrahydrofuranyl;

provided when $R^4$ is —$CH_2NR^{24}$S(=O)$_2R^{22}$, then $R^{22}$ is not H;

each $R^{23}$ is, independently at each occurrence, H, methyl, ethyl, propyl, and butyl; and alternatively, $R^{22}$ and $R^{23}$, when attached to the same nitrogen, combine to form pyrrolidinyl, piperidinyl, morpholinyl, piperazinyl, or N-methylpiperazinyl; and each $R^{24}$ is, independently at each occurrence, H, methyl, ethyl, propyl, or butyl.

In a fifth aspect, the present invention includes compounds of Formula (Ic):

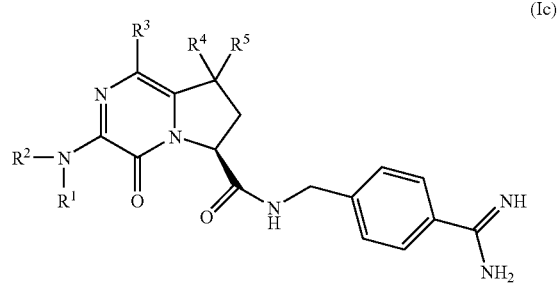

(Ic)

or a stereoisomer or pharmaceutically acceptable salt form thereof, wherein:

$R^1$ is H or methyl;

$R^2$ is H, —C(=O)$R^{2a}$, —C(=O)O$R^{2a}$, —S(=O)$_2R^{2a}$, $N(CH_3)_2$, methyl, ethyl, propyl, butyl, pentyl, hexyl, propenyl, butenyl, pentenyl, cyclopropyl, cyclobutyl, cyclopentyl, cyclohexyl, methyl substituted with $R^{2b}$, ethyl substituted with $R^{2b}$, propyl substituted with $R^{2b}$, butyl substituted with $R^{2b}$, pentyl substituted with $R^{2b}$, propenyl substituted with 0–1 $R^{2b}$, butenyl substituted with 0–1 $R^{2b}$, pentenyl substituted with 0–1 $R^{2b}$, or phenyl substituted with 0–3 $R^{2c}$;

each $R^{2a}$ is, independently at each occurrence, methyl, ethyl, propyl, butyl, pentyl, hexyl, propenyl, butenyl, pentenyl, cyclopropyl, cyclobutyl, cyclopentyl, cyclohexyl, methyl substituted with $R^{2b}$, ethyl substituted with $R^{2b}$, propyl substituted with $R^{2b}$, butyl substituted with $R^{2b}$, pentyl substituted with $R^{2b}$, propenyl substituted with 0–1 $R^{2b}$, butenyl substituted with 0–1 $R^{2b}$, pentenyl substituted with 0–1 $R^{2b}$, or phenyl substituted with 0–3 $R^{2c}$;

each $R^{2b}$ is, independently at each occurrence, H, F, Cl, $NO_2$, CN, $CF_3$, $CH_3$, —$CH_2CH_3$, —$CH_2CH_2CH_3$, —CH$(CH_3)_2$, $NH_2$, $NH(CH_3)$, $N(CH_3)_2$, —$NH(CH_2CH_3)$, —$N(CH_2CH_3)_2$, $CO_2H$, —$CO_2CH_3$, —$CO_2CH_2CH_3$, —$C(=O)NH_2$, —$C(=O)NH(CH_3)$, —$C(=O)NH(CH_2CH_3)$, —$C(=O)N(CH_3)_2$, —$C(=O)N(CH_2CH_3)_2$, —$NHC(=O)H$, —$NHC(=O)CH_3$, —$NHC(=O)CH_2CH_3$, —$NHSO_2(CH_3)$, —$NHSO_2(CH_2CH_3)$, —$SO_2CH_3$, —$SO_2CH_2CH_3$, —$SO_2NH_2$, —$SO_2NH(CH_3)$, —$SO_2NH(CH_2CH_3)$, OH, —$OCH_3$, —$OCH_2CH_3$, —$OCF_3$, —$SCH_3$, —$SCH_2CH_3$, —$SCF_3$, —$C(=O)H$, —$C(=O)CH_3$, —$C(=O)CH_2CH_3$, —$C(=O)CF_3$, —$S(=O)CH_3$, —$S(=O)CH_2CH_3$, cyclopropyl, cyclobutyl, cyclopentyl, cyclohexyl, phenyl substituted with 0–3 $R^{2c}$, or furanyl substituted with 0–3 $R^{2c}$;

alternatively, $R^1$ and $R^2$ are combined to form morpholinyl or piperidinyl;

$R^4$ is H, F, methyl, ethyl, propyl, allyl, —$NR^{22}R^{23}$, —$NHC(=O)R^{22}$, —$C(=O)NHR^{22}$, —$CH_2NR^{22}R^{23}$, —$CH_2C(=O)NR^{22}R^{23}$, —$CH_2NHC(=O)R^{22}$, —$CH_2NHC(=O)NR^{22}R^{23}$, —$CH_2C(=O)OR^{22}$, —$CH_2NHS(=O)_2R^{22}$, —$CH_2OH$, —$CH_2CH_2OH$, benzyl, phenethyl, phenylpropyl, naphthylmethyl, naphthylethyl, or naphthylpropyl;

$R^5$ is H, methyl, ethyl, propyl, or allyl;

each $R^{22}$ is, independently at each occurrence, H, methyl, ethyl, propyl, allyl, cyclopropyl, cyclobutyl, cyclopentyl, cyclohexyl, phenyl, benzyl;

provided when $R^4$ is —$CH_2NHS(=O)_2R^{22}$, then $R^{22}$ is not H; and $R^{23}$ is H, methyl, ethyl, propyl, or butyl; and alternatively, —$NR^{22}R^{23}$ forms piperidinyl.

In a sixth aspect, the present invention provides a compound selected from Examples 1–15 and 17–58 or a stereoisomer or pharmaceutically acceptable salt form thereof.

In another embodiment of the present invention, when Z is CH, $R^8$ is phenyl or 5–6 membered heteroaryl, $R^{8a}$ is OH, F, Cl, Br, I, or $CF_3$; and $R^{8b}$ is OH, F, Cl, Br, I, or $CF_3$; then $R^{16}$ is H.

In a preferred embodiment $R^8$ is —$C(=NH)NH_2$ or —$CH_2NH_2$.

In a preferred embodiment $R^8$ is —$C(=NH)NH_2$.

In another embodiment the present invention provides a pharmaceutical composition comprising a pharmaceutically acceptable carrier and a therapeutically effective amount of at least one of the compounds of the present invention or a pharmaceutically acceptable salt or prodrug form thereof.

In another embodiment the present invention provides a method for modulation of the coagulation cascade comprising administering to a patient in need of such treatment a therapeutically effective amount of at least one of the compounds of the present invention or a pharmaceutically acceptable salt or prodrug form thereof.

In another embodiment the present invention provides a method for treating thromboembolic disorders comprising: administering to a patient in need of such treatment a therapeutically effective amount of at least one of the compounds of the present invention or a pharmaceutically acceptable salt or prodrug form thereof.

In another embodiment, the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

In another embodiment, the thromboembolic disorder is selected unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

In another embodiment, the present invention provides a novel method of treating a patient in need of thromboembolic disorder treatment, comprising: administering a compound of the present invention or a pharmaceutically acceptable salt form thereof in an amount effective to treat a thromboembolic disorder.

In another embodiment, the present invention provides a method for treating a thromboembolic disorder, comprising: administering to a patient in need thereof a therapeutically effective amount of a first and additional therapeutic agent(s), wherein the first therapeutic agent is compound of Formula (I) or a pharmaceutically acceptable salt thereof and the additional therapeutic agent(s) are selected from an anti-coagulant agent, an anti-platelet agent, a thrombin inhibiting agent, a thrombolytic agent, and a fibrinolytic agent or a combination thereof.

In a preferred embodiment, the present invention provides a method for treating a thromboembolic disorder, wherein the second therapeutic agent is selected from warfarin, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

In a preferred embodiment, the present invention provides a method for treating a thromboembolic disorder, wherein the additional therapeutic agent(s) are an anti-platelet agent or a combination thereof.

In a preferred embodiment, the present invention provides a method for treating a thromboembolic disorder, wherein the additional therapeutic agent(s) is the anti-platelet agent clopidogrel.

In another embodiment, the present invention provides a novel method, comprising: administering a compound of the present invention or a pharmaceutically acceptable salt form thereof in an amount effective to treat a thromboembolic disorder.

In another embodiment, the present invention provides a compound of the present invention for use in therapy.

In another embodiment, the present invention also provides the use of a compound of the present invention for the manufacture of a medicament for the treatment of a thromboembolic disorder.

In another embodiment, the present invention provides a novel method for treating a thromboembolic disorder, comprising: administering to a patient in need thereof a therapeutically effective amount of a first and second therapeutic agent, wherein the first therapeutic agent is compound of the present invention or a pharmaceutically acceptable salt thereof and the second therapeutic agent is at least one agent selected from a second factor Xa inhibitor, an anti-coagulant agent, an anti-platelet agent, a thrombin inhibiting agent, a thrombolytic agent, and a fibrinolytic agent.

In another preferred embodiment, the present invention provides a novel method, wherein the second therapeutic agent is at least one agent selected from warfarin, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

In another preferred embodiment, the present invention provides a novel method, wherein the second therapeutic agent is at least one anti-platelet agent.

In another preferred embodiment, the present invention provides a novel method, wherein the anti-platelet agent is aspirin and clopidogrel.

In another preferred embodiment, the present invention provides a novel method, wherein the anti-platelet agent is clopidogrel.

In another embodiment, the present invention provides a novel article of manufacture, comprising:
  (a) a first container;
  (b) a pharmaceutical composition located within the first container, wherein the composition, comprises: a first therapeutic agent, comprising: a compound of the present invention or a pharmaceutically acceptable salt form thereof; and,
  (c) a package insert stating that the pharmaceutical composition can be used for the treatment of a thromboembolic disorder.

In another preferred embodiment, the present invention provides a novel article of manufacture, further comprising:
  (d) a second container;

wherein components (a) and (b) are located within the second container and component (c) is located within or outside of the second container.

In another embodiment, the present invention provides a novel article of manufacture, comprising:
  (a) a first container;
  (b) a pharmaceutical composition located within the first container, wherein the composition, comprises: a first therapeutic agent, comprising: a compound of the present invention or a pharmaceutically acceptable salt form thereof; and,
  (c) a package insert stating that the pharmaceutical composition can be used in combination with a second therapeutic agent to treat a thromboembolic disorder.

In another preferred embodiment, the present invention provides a novel article of manufacture, further comprising:
  (d) a second container;

wherein components (a) and (b) are located within the second container and component (c) is located within or outside of the second container.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

Definitions

The compounds herein described have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. All tautomers of shown or described compounds are also considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^{2b}$, $R^{8b}$, etc.) occurs more than one time in any constituent or formula for a compound, its definition at each occurrence is independent of its definition at every other occurrence. Thus, for example, if a group is shown to be substituted with 0–3 $R^{2b}$, then said group may optionally be substituted with up to three $R^{2b}$ groups and $R^{2b}$ at each occurrence is selected independently from the definition of $R^{2b}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. For example, "$C_1$–$C_{10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$–$C_6$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

"Alkenyl" or "alkenylene" is intended to include hydrocarbon chains of either a straight or branched configuration having the specified number of carbon atoms and one or more unsaturated carbon-carbon bonds which may occur in any stable point along the chain. For example, "$C_2$–$C_6$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration and one or more carbon-carbon triple bonds which may occur in any stable point along the chain. For example, "$C_2$–$C_6$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

"Cycloalkyl" is intended to include saturated ring groups, having the specified number of carbon atoms. For example, "$C_3$–$C_6$ cycloalkyl" denotes such as cyclopropyl, cyclobutyl, cyclopentyl, or cyclohexyl.

"Alkoxy" or "alkyloxy" represents an alkyl group as defined above with the indicated number of carbon atoms attached through an oxygen bridge. For example, "$C_1$–$C_6$ alkoxy" (or alkyloxy), is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" represents an alkyl group as defined above with the indicated number of carbon atoms attached through a sulphur bridge; for example methyl-S—, ethyl-S—, and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$–$C_6$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

As used herein, "carbocycle" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred carbocycles, unless otherwise specified, are cyclopropyl, cyclobutyl, cyclopentyl, cyclohexyl, phenyl, and indanyl.

As used herein, the term "heterocycle" or "heterocyclic group" is intended to mean a stable 5, 6, or 7-membered monocyclic or bicyclic or 7, 8, 9, 10, 11, 12, 13, or 14-membered bicyclic heterocyclic ring which is saturated, partially unsaturated or fully unsaturated, and which consists of carbon atoms and 1, 2, 3 or 4 heteroatoms independently selected from the group consisting of N, O and S; and including any bicyclic group in which any of the above-defined heterocyclic rings is fused to a benzene ring. The nitrogen and sulfur heteroatoms may optionally be oxidized to —NO—, —SO—, or —SO$_2$—. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heteroatoms independently selected from the group consisting of N, NH, O and S. It is to be noted that total number of S and O atoms in the aromatic heterocycle is not more than 1.

Examples of heterocycles include, but are not limited to, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred 5 to 10 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9 or 10-membered heterocycle which contains two fused rings and consists of carbon atoms and 1, 2, 3, or 4 heteroatoms independently selected from the group consisting of N, O and S. Of the two fused rings, one ring is a 5 or 6-membered monocyclic aromatic ring comprising a 5 membered heteroaryl ring, a 6-membered heteroaryl ring or a benzo ring, each fused to a second ring. The second ring is a 5 or 6 membered monocyclic ring which is saturated, partially unsaturated, or unsaturated, and comprises a 5 membered heterocycle, a 6 membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinoline, 2,3-dihydrobenzofuranyl, chromanyl, 1,2,3,4-tetrahydro-quinoxaline, and 1,2,3,4-tetrahydro-quinazoline.

As used herein, the term "bicyclic carbocycle" or "bicyclic carbocyclic group" is intended to mean a stable 9 or 10-membered carbocycle which contains two fused rings and consists of carbon atoms. Of the two fused rings, one ring is a benzo ring fused to a second ring; and the second ring is a 5 or 6 membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

As used herein, the term "aryl", "$C_6$–$C_{10}$ aryl" or "aromatic residue", is intended to mean an aromatic moiety containing, if specified, the specified number of carbon atoms; for example phenyl or naphthyl. Unless otherwise specified, "aryl", "$C_6$–$C_{10}$ aryl" or "aromatic residue" may be unsubstituted or substituted with 0 to 3 groups selected from the group: H, OH, OCH$_3$, Cl, F, Br, I, CN, NO$_2$, NH$_2$, N(CH$_3$)H, N(CH$_3$)$_2$, CF$_3$, OCF$_3$, C(=O)CH$_3$, SCH$_3$, S(=O)CH$_3$, S(=O)$_2$CH$_3$, CH$_3$, CH$_2$CH$_3$, CO$_2$H, and CO$_2$CH$_3$.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

General Synthetic Procedures and Specific Examples

The general synthetic approach to the 3-amino bicyclic pyrazinone is shown in Scheme 1. Cyclocondensation of the cyano-substituted proline derivative 1A with oxalyl chloride in solvent such as toluene or 1,2-dichlorobenzene provides the dichloropyrazine hetereocyclic core 1B with an acetic acid ester at N-5. Heating a solution of the pyrazinone 1B in ethyl acetate or dioxane in the presence of excess amine results in a selective nucleophilic displacement of the C-3 chlorine atom to give intermediate 1C. Saponification of the substituted pyrazinone ester 1C with lithium hydroxide or NaOH results in the acid 1D. At this point, the acid can be optionally hydrogenated in the presence of base and Pd/C to remove the 5-chlorine atom, or coupled under standard peptide coupling conditions with various amines. These amines are typically multi-functional, and are introduced in a protected form. Removal of these protecting groups provides the compound 1E for screening.

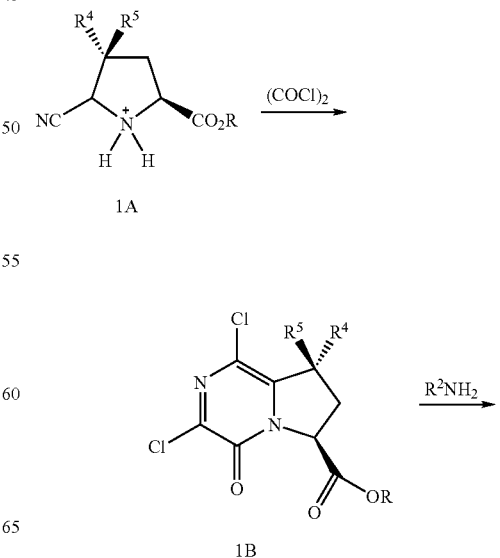

Scheme 1

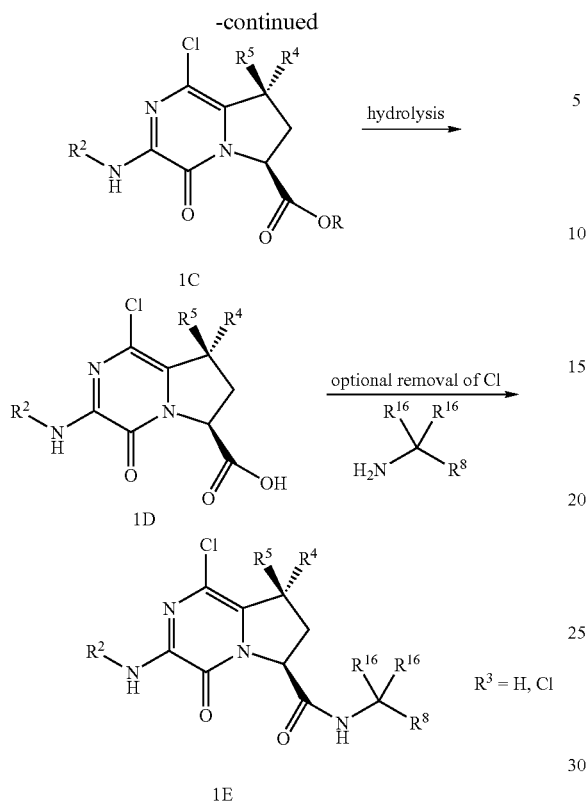

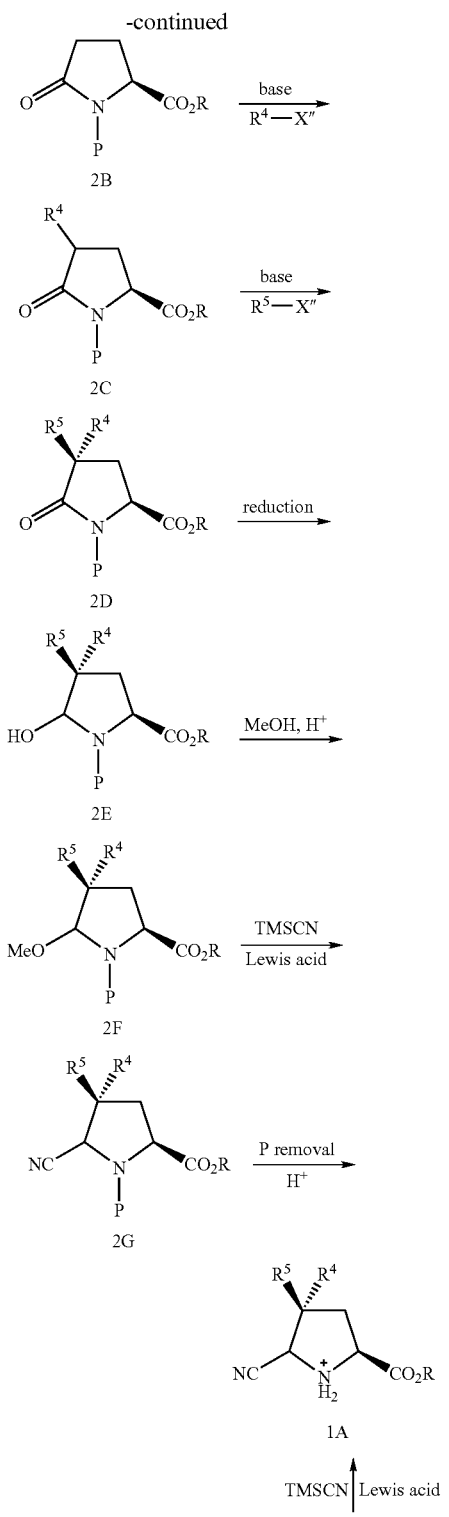

Synthesis of cyano-substituted proline derivative 1A can be accomplished by the chemistry outlined in Scheme 2. Commercial pyroglutamate is protected with a suitable protecting group, e.g. Boc. The protected pyroglutamate 2B is treated with a strong base such as lithium bis(trimethysilyl)amide (LHMDS) and alkylated with an electrophile $R^4$—X" to give 4-substituted pyroglutamate 2C. This alkylation procedure is stereoselective and can be carried out twice to give 4,4-disubstituted derivatives 2D (*J. Org. Chem.* 1994, 59, 4327). Pyroglutamate 2D is reduced by lithium triethylborohydride (super hydride) or diisobutylaluminum hydride (DIBAL) to the corresponding aminal 2E, which is exchanged with methanol under acidic conditions through acyl-iminium ion chemistry to 5-methoxy prolinate 2F. The hydroxy can also be converted to acetoxyl derivatives 2H under basic conditions. Intermediate 2F and 2H can react with trimethylsilyl cyanide catalyzed by a Lewis acid such as $BF_3$ etherate or $ZnCl_2$ in methylene chloride to give 5-cyano prolinate 2G. The protecting group is removed under acidic conditions to generate aminonitrile salt 1A that is ready to undergo cyclocondensation according to the chemistry outlined in Scheme 1.

Scheme 2

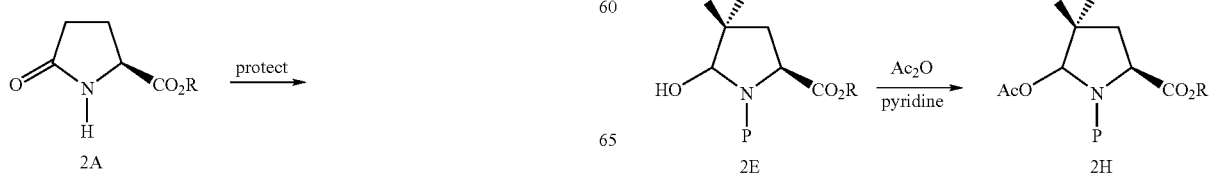

General Synthesis of 3-Aminobicyclic Pyridone are Outlined in Scheme 3

Removal of protecting group in 2D (prepared as in Scheme 2) followed by acylation of the resulting 3A with diazo acyl chloride (may be prepared by method described in *J. Org. Chem.* 1994, 59, 1418) generates the diazo compound 3B. This intermediate is subject to a rhodium-catalyzed cyclization reaction involving a dienophile to give a bicyclic intermediate 3C (*J. Org. Chem.*, 1999, 64, 8648). Treatment of intermediate 3C with acid, e.g. PTSA, results in formation of alcohol 3D. Dehydration of 3D gives rise to bicyclic pyridone carboxylate 3E. Treatment of 3E with an acid and a Curtis rearrangement of the resulting acid affords 3-amino bicyclic pyridone 3F. Deprotection of the 3-amino group followed by capping the amine functionality with sulfonyl chlorides gives rise to sulfonamide 3G. Saponification of the methyl ester 3G provides acid 3H, which is coupled under standard peptide coupling conditions with various amines. These amines are typically multi-functional, and are introduced in a protected form. Removal of these protecting groups provides the compound 3I for screening.

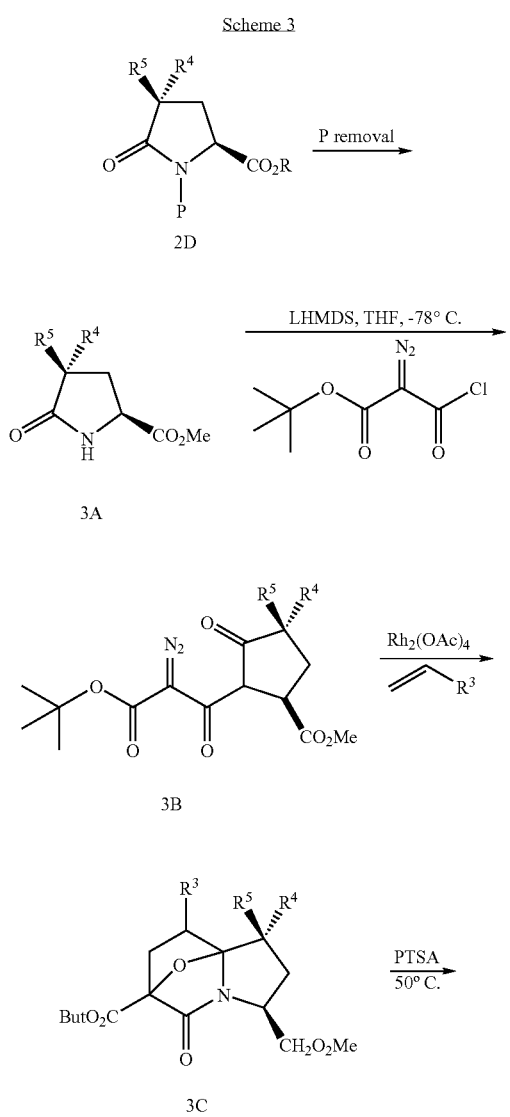

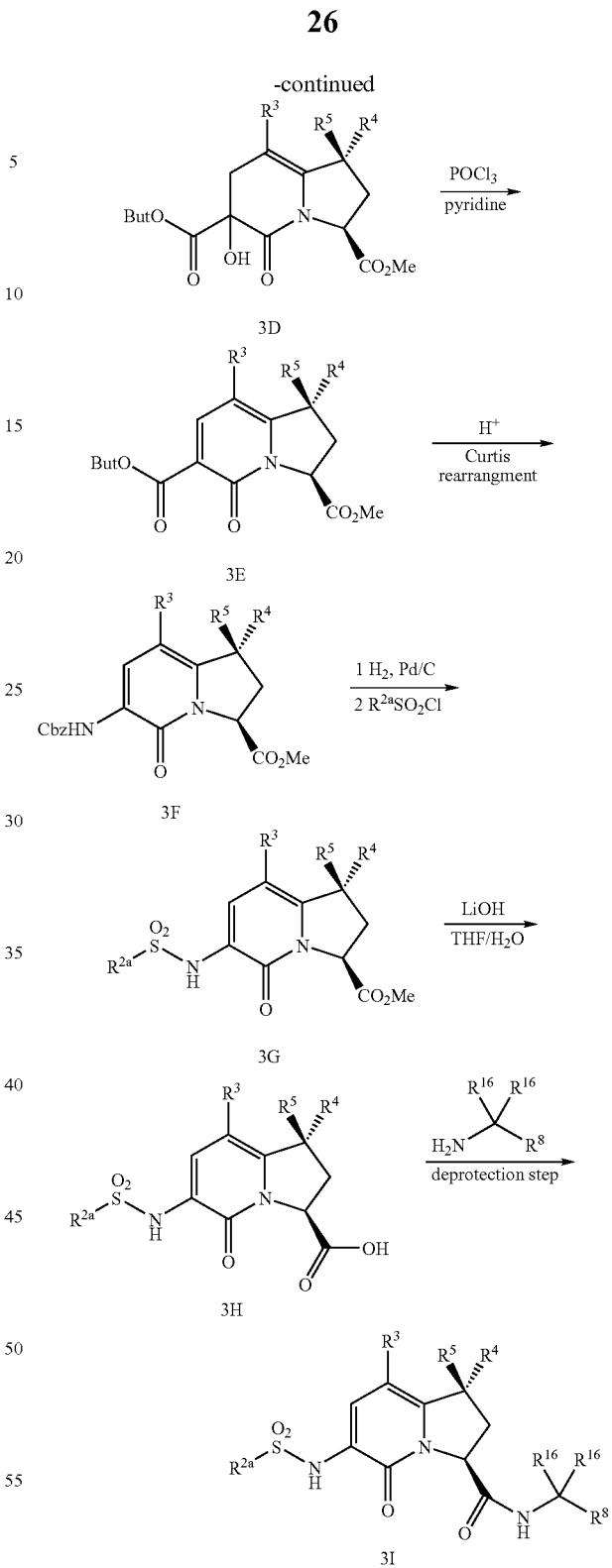

General synthesis of bicyclic pyrazine and pyridone derivatives of structure 4F and 4G is summarized in Scheme 4. Intermediate acid 4A (prepared as in Schemes 1 and 3) is reduced to alcohol 4B. Alcohol 4B is reacted with methanesulfonyl chloride to give an intermediate 4C which is displaced by sodium azide to provide azide derivative 4D. Azide in 4D is reduced to amine 4E. The intermediate 4E can either be acylated with acids carrying multifunctional groups R[8], or reductively aminated with aldehydes carrying a multifunctional group R[8], to provide 4F. Alternatively, 4E is reacted with sulfonyl chlorides carrying a multifunctional group R[8] to give 4G.

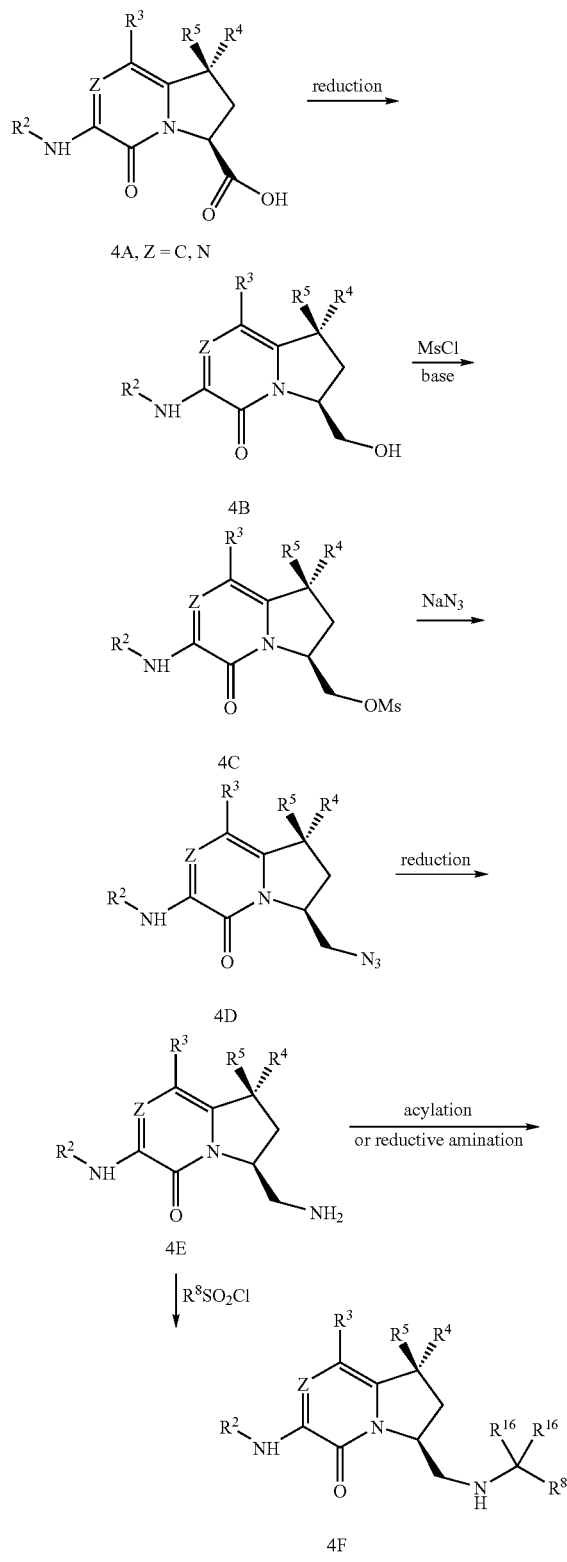

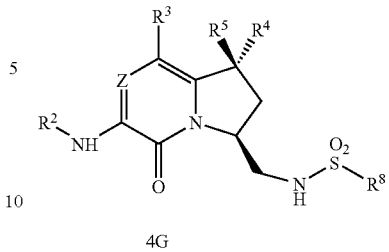

When required, separation of the racemic material can be achieved by HPLC using a chiral column and methods generally known to one skilled in the art or by a resolution using a resolving agent, for example camphonic chloride (Wilen, S. H. *Tables of Resolving Agents and Optical Resolutions* 1972, 308 pp). A chiral compound may also be directly synthesized using a chiral catalyst or a chiral ligand (e.g., Jacobsen, E. *Acc. Chem. Res.* 2000, 33, 421–431).

Other features of the invention will become apparent in the course of the following descriptions of exemplary embodiments which are given for illustration of the invention and are not intended to be limiting thereof.

EXAMPLES

Solution ratio express a volume relationship, unless stated otherwise. NMR chemical shifts ($\delta$) are reported in parts per million. Flash chromatography was carried out on silica gel according to Still's method (Still, W. C. et al. *J. Org. Chem.* 1978, 43, 2923). Abbreviations used in the Examples are defined as follows: "° C." for degrees Celsius, "MS" for mass spectrometry, "ESI" for electrospray ionization mass spectroscopy, "HR" for high resolution, "LC-MS" for liquid chromatography mass spectrometry, "eq" for equivalent or equivalents, "g" for gram or grams, "h" for hour or hours, "mg" for milligram or milligrams, "mL" for milliliter or milliliters, "mmol" for millimolar, "M" for molar, "min" for minute or minutes, "HPLC" for high pressure liquid chromatography, "rt" for room temperature, "NMR" for nuclear magnetic resonance spectroscopy, "tlc" for thin layer chromatography, "atm" for atmosphere, and "$\alpha$", "$\beta$", "R", "S", "E", and "Z" are stereochemical designations familiar to one skilled in the art.

As used throughout the specification, the following abbreviations for chemical reagents apply:
Boc is tert-butyl oxycarbonyl,
Cbz is carbonylbenzyloxy,
DIEA is diethylpropyl amine,
DMAP is dimethylaminopyridine,
DMF is dimethylformamide,
DMSO is dimethyl sulfoxide,
DMF is dimethylformamide,
DPPA is diphenylphosphoryl azide,
EDCI is 1-(3-dimethylaminopropyl)-3-ethylcarbodiimide hydrochloride,
Et is ethyl,
EtOAc is ethyl acetate,
HOAc or AcOH is acetic acid,
LHMD is lithium hexamethyldisily amide,
LiHMDS is bis(trimethylsilyl)amide,
Me is methyl,
MeOTf is methyl trifluoromethanesulfonate,
MsCl is methanesulfonyl chloride,
NMM is 4-methyl morpholine, OAc is acetate,
Pr is propyl,
PTSA is p-toluenesulfonic acid,
PyAOP is [7-Azabenzotriazol-1-yloxytris(pyrrolidino)-phosphonium hexafluorophosphate,
TFA is trifluoroacetic acid,
THF is tetrahydrofuran,
TMSCN is Trimethylsilyl cyanide, and
p-TsOH is p-toluenesulphonic acid.

The following Examples have been prepared, isolated and characterized using the methods disclosed herein. The following Examples demonstrate a partial scope of the invention and are not meant to be limiting of the scope of the invention.

Example 1

(6S)-1-Chloro-3-cyclobutylamino-4-oxo-4,6,7,8-tetrahydro-pyrrolo[1,2-a]pyrazine-6-carboxylic acid 4-carbamimidoyl-benzylamide hydrochloride

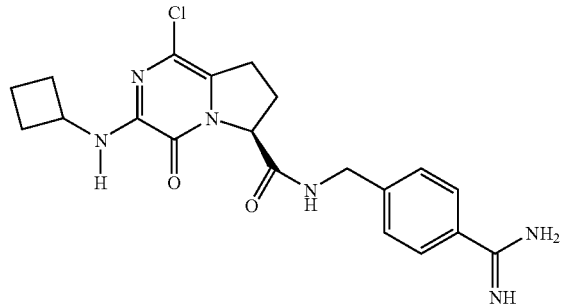

Step A: Ethyl(2S)-N-tert-butoxycarbonyl-5-hydroxyprolinate.

In a flask was placed the (2S)-5-oxo-pyrrolidine-2-carboxylic acid ethyl ester (50 g, 0.318 mol) and dissolved in 800 mL acetonitrile. Boc-anhydride was added (86 g, 0.394 mol) followed by addition of DMAP (5.8 g, 0.0477 mol). The reaction was allowed to stir overnight at room temperature at which time TLC indicated a complete reaction. The solvent was removed under vacuum and the residue diluted with EtOAc and washed with 5% citric acid. The aqueous layer was extracted 1× with EtOAc and the organics washed with brine and dried with sodium sulfate, filtered, concentrated and purified by flash chromatography (silica gel; 25–35% EtOAc/hexanes) to give ethyl(2S)-N-tert-butoxycarbonyl pyroglutamate as a yellowish solid (81 g, 99% yield). $^1$HNMR (300 MHz, CDCl$_3$) δ 1.308 (t, 3H, J=7.1 Hz), 1.50 (s, 9H) 2.05 (m, 1H) 2.3–2.8 (m, 3H) 4.24 (q, 2H, J=6.9, 14.3 Hz) 4.61 (dd, 1H J=2.9, 9.1 Hz) MS m/e 258.2 [M+H].

To a solution of the above compound (5.0 g, 19.4 mmol) in THF (80 mL) cooled at −60° C. was added LiBEt$_3$H (1.0 M in THF, 23.0 mL). The reaction was stirred at −60° C. for 30 min before it was quenched with 10 mL of saturated NaHCO$_3$ and 1.0 mL of 30% hydrogen peroxide. THF was removed under reduced pressure. The mixture was extracted with ethyl acetate. The combined organic phases were washed with brine, dried over K$_2$CO$_3$. Filtration and evaporation of the solvent gave colorless viscous oil used directly for next Step without further purification. MS m/e 242 (M−17).

Step B: Ethyl(2S)-N-tert-butoxycarbonyl-5-methoxyprolinate.

To a solution of the compound obtained from Step A (19.4 mmol) in methanol (200 mL) was added conc. H$_2$SO$_4$ (0.544 mL, 0.5 eq). The mixture was stirred at rt for 1.0 h before it was quenched with 20 mL of saturated NaHCO$_3$. Methanol was removed under reduced pressure. The residue was extracted with ethyl acetate. The combined organic phases were washed with brine and dried over Na$_2$SO$_4$. Evaporation of solvent gave a viscous oil used in the next Step without further purification. MS m/e 242 (M−MeO).

Step C: Ethyl(2S)-N-tert-butoxycarbonyl-5-cyanoprolinate.

To a solution of ethyl(2S)-N-tert-butoxycarbonyl-5-methoxyprolinate (4.10 g, 15.81 mmol) in CH$_2$Cl$_2$ (40 mL) at −50° C. was added trimethylsilyl cyanide (6.3 mL, 47.4 mmol) and BF$_3$ etherate (5.60 mL, 47.4 mmol). The mixture was stirred from −50° C. to −30° C. for 2.0 h before it was quenched with saturated NaHCO$_3$. The organic layer was separated and the aqueous phase was extracted with CH$_2$Cl$_2$. The combined organic layers were washed with brine and dried over MgSO$_4$. Filtration, evaporation of solvent and flash column chromatography (hexane/ethyl acetate, 3:1) gave separated cis and tran isomers (2.20 g). $^1$HNMR (300 MHz, CDCl$_3$) δ isomer 1: 4.68 (dd, J=4.0, 2.0 Hz) and 4.55 (t, J=5.4 Hz) for 1H, 4.40 (t, J=7.7 Hz) and 4.26 (t, J=6.9 Hz) for 1H, 3.79 (s, 3H), 2.42–1.98 (m, 4H), 1.52 (s) and 1.44 (s) for 9 H; isomer 2: 4.78 (dd, J=8.8, 1.5 Hz) and 4.67 (d, J=8.0 Hz) for 1H, 4.45 (d, J=8.8 Hz) and 4.34 (d, J=8.0 Hz) for 1H, 3.75 (s) and 3.73 (s) for 3H, 2.56–2.12 (m, 4H), 1.52 (s) and 1.43 (s) for 9H; CIMS 255 (M+H).

Step D: Ethyl(2S)-5-cyanoprolinate trifluroacetic acid salt.

To a solution of the compound obtained from Step C (2.20 g) in CH$_2$Cl$_2$ (10 mL) was added trifluoroacetic acid (11.0 mL). The mixture was stirred at rt for 1.0 h before the solvent was removed under reduced pressure. The residue was further chased with toluene to remove residual trifluoroacetic acid. The TFA salt obtained was used in the next Step without further purification.

Step E: (6S)-1,3-dichloro-4-oxo-4,6,7,8-tetrahydropyrrolo[1,2a]pyrazine-6-carboxylic acid ethyl ester.

The TFA salt obtained in Step D was suspended in toluene (15 mL) and oxaly chloride (3.02 mL, 34.0 mmol). The mixture was heated at 85° C. overnight in a pressure vessel. Toluene and excess oxaly chloride were removed under reduced pressure. The residue was purified by flash column chromatography (hexane/ethyl acetate, 1:1) to give 1.10 g of the product as a viscous, brownish oil. $^1$HNMR (300 MHz, CDCl$_3$) δ 5.17 (dd, J=9.5, 2.9 Hz, 1H), 3.83 (s, 3H), 3.20 (m, 2H), 2.62 (m, 1H), 2.41 (m, 1H).

Step F: (6S)-1-chloro-3-cyclobutyl-4-oxo-4,6,7,8-tetrahydropyrrolo[1,2a]pyrazine-6-carboxylic acid ethyl ester.

A mixture of the dichloropyrazinone obtained from Step E (90 mg, 0.32 mmol) and cyclobutyl amine (114 μL, 4.0 eq) in ethyl acetate (2.0 mL) was refluxed for 4.0 h. Solvent was removed and the product was purified by a flash column chromatography eluting with hexane/ethylacetate (2:1) to give 80 mg product. $^1$HNMR (300, CDCl$_3$) δ 6.19 (d, br, 1H), 5.05 (dd, J=9.5 and 3.3 Hz, 1H), 4.46 (m, 1H), 3.80 (s, 3H), 3.03 (m, 2H), 2.54–2.32 (m, 4H), 1.93 (m 2H), 1.75 (m, 2H).

Step G: (6S)-1-chloro-3-cyclobutyl-4-oxo-4,6,7,8-tetrahydropyrrolo[1,2a]pyrazine-6-carboxylic acid.

To the ester from Step F (78 mg, 0.25 mmol) dissolved in THF (1.5 mL) was added LiOH (1.0 M, 0.5 mL). The mixture was stirred at rt for 1.5 h. It was acidified with 5% citric acid, and extracted with EtOAc. The organic layer was washed with brine and dried over MgSO$_4$. Evaporation of solvent and lyopholization gave 70 mg of a white solid product. $^1$HNMR (300 MHz, DMSO-d$_6$) δ 7.65 (d, J=7.7 Hz, 1H), 4.97 (dd, J=9.7 and 3.2 Hz, 1H), 4.28 (m, 1H), 3.34 (s br), 2.91 (m, 2H), 2.22–2.01 (m, 6H), 1.64 (m, 2H).

Step H: (6S)-[(4-{[(1-Chloro-3-cyclobutylamino-4-oxo-4,6,7,8-tetrahydro-pyrrolo[1,2-a]pyrazine-6-carbonyl)-amino]-methyl}-phenyl)-imino-methyl]-carbamic acid benzyl ester.

To a solution of the above acid (31 mg, 0.09 mmol) in DMF (1.0 mL) was added [(4-aminomethyl-phenyl)-imino-methyl]-carbamic acid benzyl ester HCl salt (32.2 mg, 0.09 mmol, prepared as described in Synth. Commun. 1998, 28, 4419), PyAOP (58.9 mg, 1.25 eq) and DIEA (78.8 μL, 5.0 eq). The mixture was stirred at rt for 3 h. It was then subjected to HPLC purification to give the desired product as a white solid (54 mg, 74% yield). $^1$HNMR (300 MHz, CDCl$_3$) δ 8.38 (br, 1H), 7.61 (br, 2H), 7.34 (s, 5H), 7.19 (br, 2H), 5.25 (s, 2H), 5.09 (br, 1H), 4.39 (m, 2H), 4.15 (br, 1H), 3.01–2.91 (m, 2H), 2.33 (br, 4H), 1.89 (m, 2H), 1.72 (m, 2H). MS m/e 549 (M+1).

Step I: Example 1

To a solution of the compound obtained from Step H (50 mg) in methanol (2.0 mL) was added HCl in dioxane (4.0 M, 0.13 mL) and 10% Pd/C (20 mg). This mixture was hydrogenated with a hydrogen ballon for 1.0 h. Removal of Pd/C and solvent gave the desired product as a white solid (34 mg, 82%). $^1$HNMR (300 MHz, DMSO-d$_6$) δ 9.34 (br, 2H), 9.05 (m, 3H), 7.78 (d, J=8.5 Hz, 2H), 7.49 (d, J=8.4 Hz, 2H), 5.02 (m 1H), 4.43–4.31 (m, 3H), 3.5 (s, br), 2.90 (m, 2H), 2.21–2.05 (m, 6H), 1.65 (m, 2H). MS m/e 415(M+1).

Example 2

(6S,8R)-1-Chloro-3-cyclobutylamino-4-oxo-8-(3-phenyl-propyl)-4,6,7,8-tetrahydro-pyrrolo[1,2-a]pyrazine-6-carboxylic acid 4-carbamimidoyl-benzylamide hydrochloride

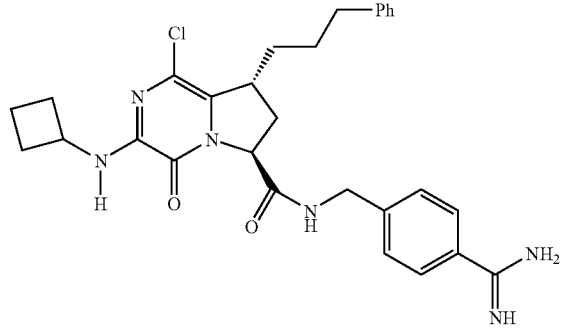

Step A: (2S,4R)-5-oxo-4-(3-phenyl-allyl)-pyrrolidine-1,2-dicarboxylic acid 1-tert-butyl ester 2-ethyl ester.

To a solution of ethyl(2S)-N-tert-butoxycarbonyl pyroglutamate (8.80 g, 34.2 mmol) in THF (200 mL) at −78° C. was slowly added LHMDS (1.0 M in THF, 41 mL, 41.0 mmol). After the mixture was stirred for 1.0 h at −78° C., cinnamyl bromide (7.6 mL, 51 mmol) was added, and stirring was continued at −78° C. for 2.0 h. The reaction was quenched at −78° C. with 5% citric acid and extracted with ethyl acetate. The combined organic phases were washed with 5% NaHCO$_3$, brine, and dried over MgSO$_4$. Evaporation of the solvent and flash column chromatography (hex-anes/EtOAc, 5:1) gave the desired trans product (6.0 g) as a viscous oil. $^1$HNMR (300 MHz, CDCl$_3$) δ 7.35–7.20 (m, 5H), 6.46 (d, J=16.0 Hz, 1H), 6.15 (dt, J=16.0, 7.3 Hz, 1H), 4.50 (d, J=9.5 Hz, 1H), 4.20 (q, J=7.3 Hz, 2H), 2.80 (m, 2H), 2.40 (m, 1H), 2.20–2.00 (m, 2H), 1.50 (s, 9H), 1.27 (t, J=7.3 Hz, 3H). MS m/e 512 (M+Na). The cis-isomer (1.0 g) was obtained as a minor product.

Step B: (2S, 4R)-5-oxo-4-(3-phenyl-propyl)-pyrrolidine-1,2-dicarboxylic acid 1-tert-butyl ester 2-ethyl ester.

A solution of the compound obtained from Step A (6.0 g) and Pd/C (10%, 620 mg) in methanol (150 mL) was hydrogenated at 40 psi in a par-shaker for 3.0 h. Pd/C was removed by filtration through a pad of celite. Removal of solvent under reduced pressure gave practically pure product as a viscous oil. $^1$HNMR (300 MHz, CDCl$_3$) δ 7.29–7.14 (m, 5H), 4.53 (d, J=9.5 Hz, 1H), 4.22 (q, J=7.0 Hz, 2H), 2.60 (m, 3H), 2.20 (m, 1 H), 1.98 (m, 2H), 1.64 (m, 2H), 1.50 (s, 9H), 1.28 (t, J=7.0 Hz, 3H).

Step C: Ethyl(2S, 4R)-N-tert-butoxycarbonyl-3-phenylpropyl-5-methoxyprolinate.

This compound was prepared in a procedure similar to that of Example 1, Steps A–B. $^1$HNMR (300 MHz, CDCl$_3$) δ 7.30–7.15 (m, 5H), 5.17–4.99 (m, 1H), 4.20 (m, 3H), 3.45, 3.43, 3.39 (s, 3H), 2.61 (m, 2H), 2.22–1.60 (m, 9H), 1.56, 1.48, 1.43, 1.40 (s, 9H), 1.28 (m, 3H), MS m/e 414.2 (M+Na).

Step D: (6S, 8R)-1,3-dichloro-4-oxo-8-(3-phenyl-propyl)-4,6,7,8-tetrahydro-pyrrolo[1,2-a]pyrazine-6-carboxylic acid ethyl ester.

This compound was prepared in a procedure similar to that of Example 1, Steps C–E. $^1$HNMR (300 MHz, CDCl$_3$) δ 7.33–7.15 (m, 5H), 4.98 (dd, J=8.8, 6.5 Hz, 1H), 4.22 (m, 2H), 3.51 (m, 1H), 2.64 (m, 2H), 2.40 (m, 2H), 2.04 (m, 1H), 1.45 (m, 3H), 1.30 (t, J=6.9 Hz, 3H).

Step E: (6S, 8R)-1-Chloro-3-cyclobutylamino-4-oxo-8-(3-phenyl-propyl)-4,6,7,8-tetrahydro-pyrrolo[1,2-a]pyrazine-6-carboxylic acid ethyl ester.

A mixture of the dichloropyrazinone obtained from Step D (90 mg, 0.22 mmol) and cyclobutyl amine (78 μL, 4.0 eq) in ethyl acetate (2.0 mL) was refluxed for 4.0 h. Solvent was removed and the product was purified by a flash column chromatography eluting with hexane/ethylacetate (3:1) to give 78 mg product. $^1$HNMR (300 MHz, CDCl$_3$) δ 7.25–7.13 (m, 5H), 6.91 (d, 1H, J=7.0 Hz), 4.93 (t, 1H, J=8.0 Hz), 4.39 (m, 1H), 4.20 (q, 2H, J=7.8 Hz), 3.40 (m, 2H), 2.60 (m, 2H), 2.34 (m, 4H), 2.00 (m, 3H), 1.90–1.80 (m, 6H), 1.22 (t, 3H, J=7.8 Hz);

Step F: (6S, 8R)-1-Chloro-3-cyclobutylamino-4-oxo-8-(3-phenyl-propyl)-4,6,7,8-tetrahydro-pyrrolo[1,2-a]pyrazine-6-carboxylic acid.

To the ester from Step E (78 mg, 0.18 mmol) dissolved in methanol (1.0 mL) was added LiOH (1.0 M, 0.36 mL). The mixture was stirred at rt for 1.5 h. It was acidified with 5% citric acid, and extracted with EtOAc. The organic layer was washed with brine and dried over MgSO$_4$. Evaporation of solvent and lyopholization gave 70 mg white solid used directly in the next Step.

Step G: (6S, 8R)-{4-({[1-Chloro-3-cyclobutylamino-4-oxo-8-(3-phenyl-propyl)-4,6,7,8-tetrahydro-pyrrolo[1,2-a]pyrazine-6-carbonyl]-amino}-methyl)-phenyl]-imino-methyl}-carbamic acid tert-butyl ester.

To the above acid (44.2 mg, 0.11 mmol) in THF (2.0 ML) at −20° C. was added N-methyl morpholine (16.5 μL, 1.36 eq) and isobutyl chloroformate (16.5 μL, 1.15 eq). The mixture was stirred at −20° C. for 30 min, followed by addition of [(4-aminomethyl-phenyl)-imino-methyl]-carbamic acid tert-butyl ester (32 mg, 1.15 eq). The mixture was stirred from −20° C. to rt over 2.0 h. The mixture was diluted with EtOAc, washed with 5% citric acid, 5% NaHCO3 and brine. Column chromatography gave 54 mg (75%) of product as a white solid. $^1$HNMR (300 MHz, CDOD$_3$) δ 7.78 (d, 2H, J=8.0 Hz), 7.40 (m, 2H), 7.24 (t, 2H, J=8.0 Hz), 7.16 (m, 3H), 4.94 (m, 1H), 4.4 (m, 3H), 3.4 (m, 1H), 2.6 (m, 2H), 2.36 (m, 4H), 2.0 (m, 3H), 1.6 (m, 5H).

Step H: Example 2.

To a solution the compound (54 mg, 0.085 mmol) obtained from Step G was added HCl in dioxane (4.0 M, 0.38 mL, 1.5 mmol) and 2 drops of methanol. The mixture was stirred at rt overnight. Solvent was removed to give a white solid as product in quantitative yield. $^1$HNMR (300 MHz, CDOD$_3$) δ 9.35 (s, 2H), 9.07 (s, 2H), 7.80 (d, 2H, J=8.5 Hz), 7.47 (d, 2H, J=6.6 Hz), 7.30–7.16 (m, 5H), 4.96 (t, 1H, J=7.3 Hz), 4.42–4.23 (m, 3H), 3.24 (m, 1H), 2.60 (m, 2H), 2.2–1.6 (m, 12H). MS m/e 533.4 (M+H).

Example 3

(6S,8S)-1-Chloro-3-cyclobutylamino-4-oxo-8-(3-phenyl-propyl)-4,6,7,8-tetrahydro-pyrrolo[1,2-a]pyrazine-6-carboxylic acid 4-carbamimidoyl-benzylamide hydrochloride

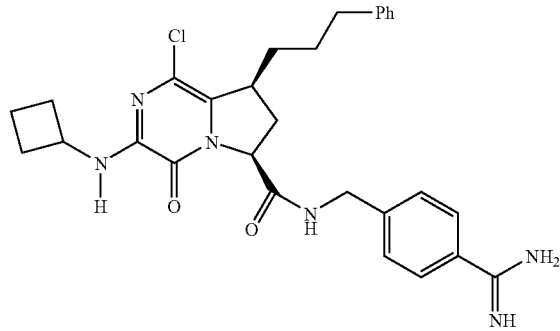

This compound was prepared in a procedure similar to that of Example 2, starting with the cis-isomer obtained in Step A of Example 2. MS m/e 533 (M+H).

Example 4

(6S, 8R)-1-Chloro-3-cyclobutylamino-8-(3-naphthalen-1-yl-propyl)-4-oxo-4,6,7,8-tetrahydro-pyrrolo[1,2-a]pyrazine-6-carboxylic acid 4-carbamimidoyl-benzylamide hydrochloride

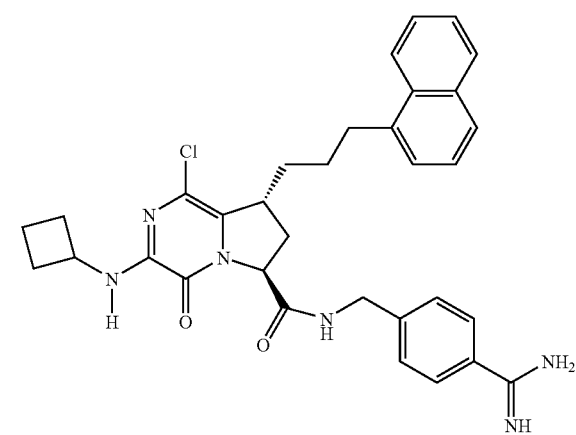

This compound was prepared in a procedure similar to that of Example 2. $^1$HNMR (300 MHz, CDCl$_3$) δ 9.34 (s, 2H), 9.07 (s, 2H), 8.08 (d, 1H, J=7.30 Hz), 7.90 (d, 1H, J=7.30 Hz), 7.77 (d, 3H, J=8.5 Hz), 7.6–7.3 (m, 6H), 4.95 (t, 1H, J=7.7 Hz), 4.5–4.2 (m, 3H), 3.05 (m, 2 H), 2.2–2.0 (6H, 1.7 (m, 6H); MS m/e 583.4 (M+H).

Example 5

(6S,8S)-1-Chloro-3-cyclobutylamino-8-(3-naphthalen-1-yl-propyl)-4-oxo-4,6,7,8-tetrahydro-pyrrolo[1,2-a]pyrazine-6-carboxylic acid 4-carbamimidoyl-benzylamide hydrochloride

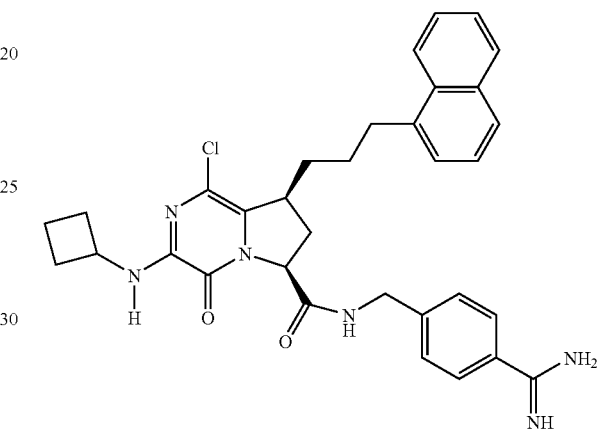

This compound was prepared in a procedure similar to that of Example 2. MS m/e 583.4 (M+H).

Example 6

(6S, 8R)-8-Benzyl-1-chloro-3-cyclobutylamino-4-oxo-4,6,7,8-tetrahydro-pyrrolo[1,2-a]pyrazine-6-carboxylic acid 4-carbamimidoyl-benzylamide hydrochloride

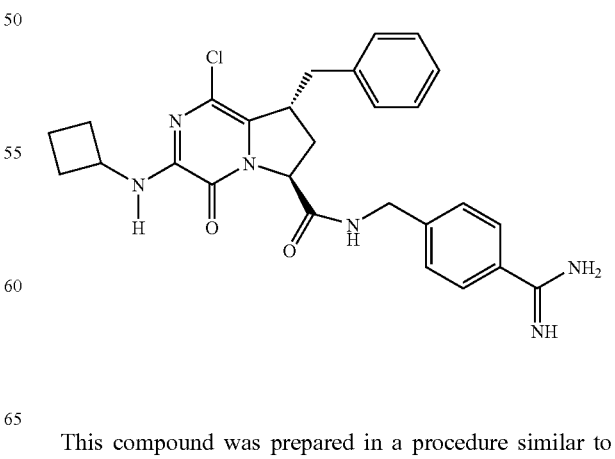

This compound was prepared in a procedure similar to that of Example 2. MS m/e 505 (M+1).

Example 7

(6S,8S)-8-Benzyl-1-chloro-3-cyclobutylamino-4-oxo-4,6,7,8-tetrahydro-pyrrolo[1,2-a]pyrazine-6-carboxylic acid 4-carbamimidoyl-benzylamide hydrochloride

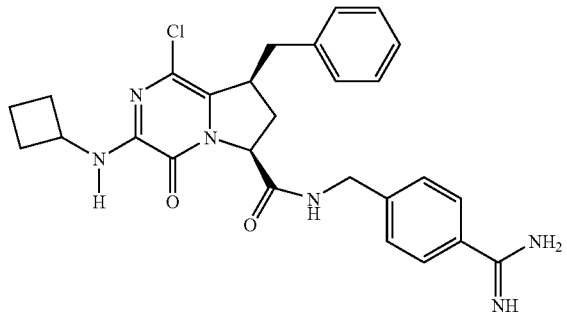

This compound was prepared in a procedure similar to that of Example 2. MS m/e 505 (M+1).

Example 8

(6S,8R)-1-Chloro-3-cyclobutylamino-8-naphthalen-2-ylmethyl-4-oxo-4,6,7,8-tetrahydro-pyrrolo[1,2-a]pyrazine-6-carboxylic acid 4-carbamimidoyl-benzylamide hydrochloride

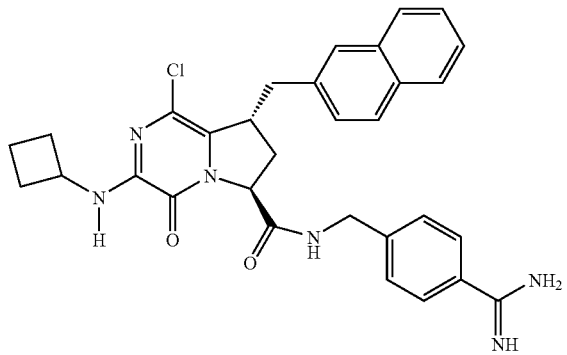

This compound was prepared in a procedure similar to that of Example 2. MS m/e 555 (M+1).

Example 9

(6S,8S)-1-Chloro-3-cyclobutylamino-8-naphthalen-2-ylmethyl-4-oxo-4,6,7,8-tetrahydro-pyrrolo[1,2-a]pyrazine-6-carboxylic acid 4-carbamimidoyl-benzylamide hydrochloride

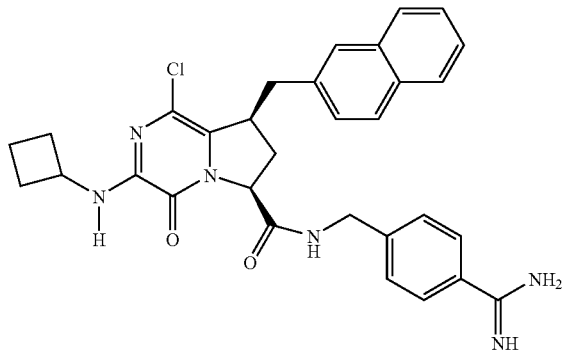

This compound was prepared in a procedure similar to that of Example 2. MS m/e 555(M+1).

Example 10

(6S)-1-Chloro-3-cyclobutylamino-8,8-dimethyl-4-oxo-4,6,7,8-tetrahydro-pyrrolo[1,2-a]pyrazine-6-carboxylic acid 4-carbamimidoyl-benzylamide tri-hydrochlroride

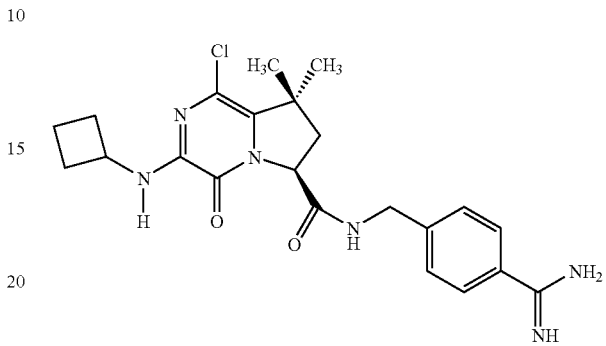

Step A: Ethyl(2S)-N-tert-butoxycarbonyl-4,4-dimethyl-5-hydroxyprolinate.

To a solution of the ethyl(2S)-N-tert-butoxycarbonylpyroglutamate (500 mg, 1.94 mmol) in THF at −60° C. was added LHMDS (1.0 M in THF, 2.14 mL). After 10 min, methyl triflate (0.242 mL, 1.10 eq) was slowly introduced. The mixture was stirred between −60° C. to −50° C. for 30 min. A second portion of LHMDS (2.14 mL) was added, followed by methyl triflate (0.242 mL) after 10 min. The reaction mixture was stirred between −55° C. to −40° C. for 30 min. It was quenched by addition of 5% citric acid. Removal of solvent, extraction with EtOAc and column chromatography gave 510 mg of desired product as colorless solid (92%). $^1$HNMR (300 MHz, CDCl$_3$) δ 4.53 (dd, 1H, J=9.1, 5.6 Hz), 4.2 (q, 2H, J=7.6 Hz), 2.2 (1H, m), 1.94 (dd, 1H, J=13.1, 5.1 Hz), 1.53 (s, 9H), 1.32 (t, 3 H, J=7.6 Hz), 1.28 (s, 6H).

Step B: (6S)1,3-dichloro-8,8-dimethyl-4-oxo-4,6,7,8-tetrahydro-pyrrolo[1,2-a]pyrazine-6-carboxylic acid ethyl ester.

This compound was prepared in 34% overall yield as a brownish solid in a procedure similar to that of Example 1, Steps A–E. $^1$HNMR (300 MHz, CDCl$_3$) δ 5.01 (dd, 1H, J=9.9, 4.4 Hz), 4.28 (m, 2H), 2.57 (m, 1H), 2.24 (dd, 1H, J=13.6, 3.8 Hz), 1.56 (s, 3 H), 1.51 (s, 1H), 1.34 (t, 3 H, J=7.8 Hz).

Step C: (6S)-1-Chloro-3-cyclobutylamino-8,8-dimethyl-4-oxo-4,6,7,8-tetrahydro-pyrrolo[1,2-a]pyrazine-6-carboxylic acid ethyl ester.

This compound was prepared in a procedure similar to that of Example 1, Step F. $^1$HNMR (300 MHz, CDCl$_3$) δ 6.15 (d, b, 1H), 4.89 (dd, J=9.5 and 4.3 Hz, 1H), 4.46 (m, 1H), 4.26 (q, J=7.1 Hz, 2H), 2.39 (m, 3H), 2.16 (dd, J=13.2 and 4.4 Hz, 1H), 1.92 (m, 2H), 1.74 (m, 2H), 1.45 (s, 3H), 1.42 (s, 3H), 1.30 (t, J=7.1 Hz, 3H).

Step D: (6S)-1-Chloro-3-cyclobutylamino-8,8-dimethyl-4-oxo-4,6,7,8-tetrahydro-pyrrolo[1,2-a]pyrazine-6-carboxylic acid.

This compound was prepared in a procedure similar to that of Example 1, Step G. $^1$HNMR (300 MHz, DMSO-d$_6$) δ 7.78 (d, J=7.7 Hz 1H), 4.89 (dd, J=9.9 and 3.6 Hz, 1H), 4.29 (m, 1H), 2.46 (m 2H), 2.11 (m, 4H), 1.65 (m, 2H), 1.39 (s, 3H), 1.31 (s, 3H).

Step E: (6S)-[(4-{[(1-Chloro-3-cyclobutylamino-8,8-dimethyl-4-oxo-4,6,7,8-tetrahydro-pyrrolo[1,2-a]pyrazine-6-carbonyl)-amino]-methyl}-phenyl)-imino-methyl]-carbamic acid benzyl ester.

This compound was prepared in a procedure similar to that of Example 1, Step H. ¹HNMR (300 MHz, DMSO-d₆) δ 8.94 (t, J=5.8 Hz, 1H), 7.78 (d, J=8.4 Hz, 2H), 7.48–7.38 (m, 7H), 5.32 (s, 2H), 4.93 (dd, J=9.5 and 3.7 Hz, 1H), 4.41 (dd, J=14.6, and 6.2 Hz, 1H), 4.28 (m, 1H), 3.58 (s, b), 2.41 (dd, J=13.1 and 9.9 Hz, 1H), 2.19 (m, 2H), 2.07 (t, J=9.4 Hz, 2H), 1.99 (dd, J=13.2 and 4.1 1H), 1.64 (m, 2H), 1.39 (s, 3H), 1.33 (s, 3H). MS m/e 577 (M+1).

Step F: Example 10.

This compound was prepared in a procedure similar to that of Example 1, Step I. ¹HNMR (300 MHz, DMSO-d₆) δ 9.35 (s, 2H), 9.08 (s, 2H), 9.00 (t, b, 1H), 7.78 (d, J=8.4 Hz 2H), 7.50 (d, J=8.1 Hz, 2H), 4.94 (dd, J=9.5 and 3.7 Hz, 1H), 4.42 (m, 1H), 4.33 (m, 1H), 2.41 (dd, J=13.2 and 9.9 Hz, 1H), 2.18 (m, 2H), 2.08 (t, J=9.7 Hz, 2H), 1.98 (dd, J=13.2 and 4.0 Hz, 1H), 1.65 (m, 2H), 1.39 (s, 3H), 1.33 (s 1H). MS m/e 443 (M+1).

Example 11

(6S)-1-Chloro-3-cyclopropylamino-8,8-dimethyl-4-oxo-4,6,7,8-tetrahydro-pyrrolo[1,2-a]pyrazine-6-carboxylic acid 4-carbamimidoyl-benzylamide hydrochloride

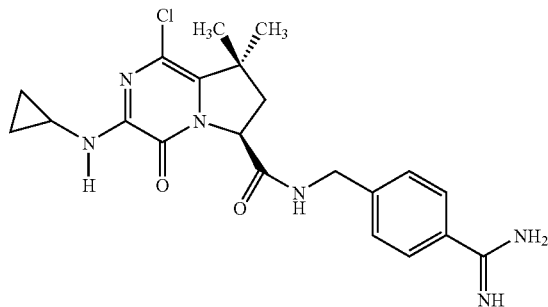

Step A: (6S)-1-Chloro-3-cyclopropylamino-8,8-dimethyl-4-oxo-4,6,7,8-tetrahydro-pyrrolo[1,2-a]pyrazine-6-carboxylic acid ethyl ester.

This compound was prepared in a procedure similar to that of Example 1, Step F. ¹HNMR (300 MHz, CDCl₃) δ 6.15 (br, 1H), 4.91 (dd, J=9.7 and 4.6 Hz, 1H), 4.27 (q, J=7.1 Hz, 2H), 2.85 (m, 1H), 2.41 (dd, J=13.4 and 9.7 Hz, 1H), 2.18 (dd, J=13.4 and 4.6 Hz, 1H), 1.49 (s, 3H), 1.45 (s, 3H), 1.31 (t, J=7.1 Hz, 3H), 0.87 (m, 2H), 0.59 (m, 2H).

Step B: (6S)-1-Chloro-3-cyclopropylamino-8,8-dimethyl-4-oxo-4,6,7,8-tetrahydro-pyrrolo[1,2-a]pyrazine-6-carboxylic acid.

This compound was prepared in a procedure similar to that of Example 1, Step G. ¹HNMR (300 MHz, DMSO-d₆) δ 7.58 (d, J=4.4 Hz, 1H), 4.88 (dd, J=10.3 and 3.7 Hz, 1H), 3.33 (s, br), 2.69 (m, 1H), 2.43 (m, 1H), 2.07 (dd, J=13.6 and 3.5 Hz, 1H), 1.41 (s, 3H), 1.32 (s, 3H), 0.71–0.55 (m, 4H).

Step C: (6S)-[(4-{[(1-Chloro-3-cyclopropylamino-8,8-dimethyl-4-oxo-4,6,7,8-tetrahydro-pyrrolo[1,2-a]pyrazine-6-carbonyl)-amino]-methyl}-phenyl)-imino-methyl]-carbamic acid benzyl ester.

This compound was prepared in a procedure similar to that of Example 1, Step H. ¹HNMR (300 MHz, CD₃OD) δ 7.82 (d, J=8.4 Hz, 2H), 7.46–7.29 (m, 7H), 5.19 (s, 2H), 4.94 (dd, J=9.9 and 4.7 Hz, 1H), 4.47 (q, J=11.7 Hz, 2H), 2.74 (m, 1H), 2.45 (dd, J=13.2 and 9.9 Hz, 1H), 2.12 (dd, J=13.2 and 4.7 Hz, 1H), 0.79 (m, 2H), 0.56 (m, 2H).

Step D: Example 10.

This compound was prepared in a procedure similar to that of Example 1, Step I. ¹HNMR (300 MHz, CD₃OD) δ 9.25 (br 2H), 8.75 (br, 2H), 7.76 (d, J=8.4 Hz, 2H), 7.59 (d, J=8.4 Hz, 2H), 5.00 (dd, 1H), 4.52 (q, 2H), 2.78 (m, 1H), 2.50 (dd, 1H), 2.16 (dd, 1H), 1.48 (s, 3H), 1.46 (s, 3H), 0.87 (m, 2H), 0.64 (m, 2H).

Example 12

(6S)-1-Chloro-3-cyclopentylamino-8,8-dimethyl-4-oxo-4,6,7,8-tetrahydro-pyrrolo[1,2-a]pyrazine-6-carboxylic acid 4-carbamimidoyl-benzylamide hydrochloride

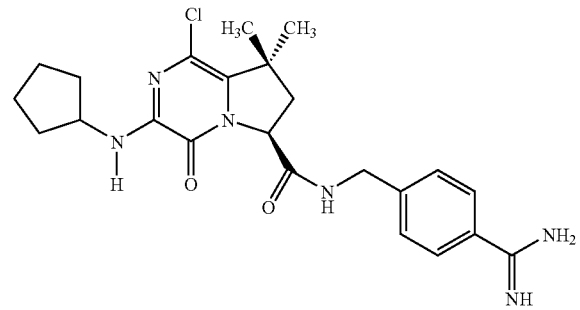

Step A: (6S)-1-Chloro-3-cyclopentylamino-8,8-dimethyl-4-oxo-4,6,7,8-tetrahydro-pyrrolo[1,2-a]pyrazine-6-carboxylic acid ethyl ester.

This compound was prepared in a procedure similar to that of Example 1, Step F. ¹HNMR (300 MHz, CDCl₃) δ 6.07 (br, 1H), 4.90 (dd, J=9.5 and 4.8 Hz, 1H), 4.29 (m, 3H), 2.40 (dd, J=13.2 and 4.8 Hz, 1H), 2.18 (dd, J=13.2 and 9.5 Hz, 1H), 2.07 (m, 2H), 1.77–1.61 (m, 4H), 1.50 (m, 2H), 1.48 (s, 3H), 1.44 (s, 3H), 1.32 (t, J=7.2 Hz, 3H).

Step B: (6S)-1-Chloro-3-cyclopentylamino-8,8-dimethyl-4-oxo-4,6,7,8-tetrahydro-pyrrolo[1,2-a]pyrazine-6-carboxylic acid.

This compound was prepared in a procedure similar to that of Example 1, Step G. ¹HNMR (300 MHz, DMSO-d₆) δ 7.24 (d, J=7.7 Hz, 1H), 4.88 (dd, J=9.9 and 4.3 Hz, 1H), 4.11 (m, 1H). 2.44 (m, 1H), 2.06 (m, 1H), 1.99 (m, 2H), 1.66 (m, 2H), 1.54 (m, 4H), 1.40 (s, 3H), 1.31 (s, 3H).

Step C: (6S)-[(4-{[(1-Chloro-3-cyclopentylamino-8,8-dimethyl-4-oxo-4,6,7,8-tetrahydro-pyrrolo[1,2-a]pyrazine-6-carbonyl)-amino]-methyl}-phenyl)-imino-methyl]-carbamic acid benzyl ester.

This compound was prepared in a procedure similar to that of Example 1, Step H. ¹HNMR (300 MHz, CD₃OD) δ 7.97 (s, 1H), 7.83 (d, J=8.1 hz, 2H), 7.46–7.29 (m, 7H), 6.52 (s, 2H), 4.94 (dd, J=9.6 and 4.8 Hz, 1H), 4.55 (q, J=15.4 Hz, 2H), 4.20 (m, 1H), 2.42 (m, 1H), 2.11 (m, 1H), 2.01 (m, 2H), 1.75–1.52 (m, 6H), 1.45 (s, 3H), 1.44 (s, 3H).

Step D: Example 12.

This compound was prepared in a procedure similar to that of Example 1, Step I. ¹HNMR (300 MHz, CD₃OD) δ 9.25 (s, br, 2H), 8.75 (s, br, 2H), 7.98 (s, 1H), 7.77 (d, J=8.4 Hz, 2H), 7.60 (d, J=8.4 Hz, 2H), 4.54 (dd, 1H), 4.50 (q, 2H), 4.22 (m, 1H), 2.50 (dd, 1H), 2.15 (dd, 1H), 2.05 (m, 2H), 1.82–1.54 (m, 6H), 1.47 (s, 3H), 1.45 (s, 3H).

Example 13

(6S,8R)-1-Chloro-3-cyclobutylamino-8-hydroxymethyl-8-methyl-4-oxo-4,6,7,8-tetrahydro-pyrrolo[1,2-a]pyrazine-6-carboxylic acid 4-diaminomethyl-benzylamide hydrochloride

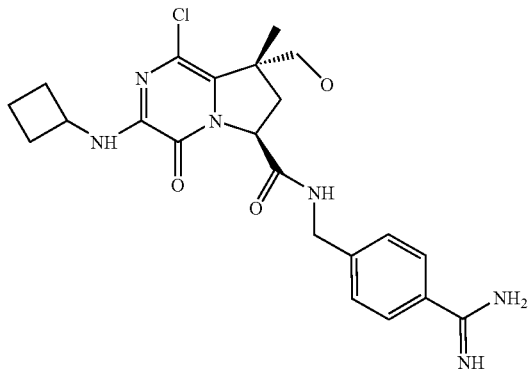

Step A: (2S, 4R)-4-Methyl-5-oxo-pyrrolidine-1,2,4-tricarboxylic acid 4-benzyl ester 1-tert-butyl ester 2-methyl ester.

To a solution of (2S)-5-oxo-pyrrolidine-1,2-dicarboxylic acid 1-tert-butyl ester 2-methyl ester (6.0 g, 24.9 mmol) in THF (100 mL) at −78° C. was added LHMDS (1.0 M in THF, 27.13 mL). After 15 min stirring at −78° C., MeOTf (2.93 mL, 1.05 eq) was added slowly. The mixture was stirred at −78° C. for 30 min before a second portion of LHMDS (27.13 mL) was added. After 20 min stirring, benzyl chloroformate (4.42 mL, 1.25 eq) was added. The mixture was stirred at −78° C. for 2.0 h, and was quenched with 5% citric acid. Removal of solvent, extraction with EtOAC and column chromatography gave the product as a white solid (7.3 g, 75%). $^1$HNMR (300 MHz, CDCl$_3$) δ 7.38 (m, 5H), 5.2 (m, 2H), 4.6 (m, 1H), 3.8 (s, 3H), 2.87 (dd, 1H, 13.6, 8.8 Hz), 1.88 (dd, 1H, J=13.6; 6.6 Hz), 1.6 (s, 3H), 1.5 (s, 9H).

Step B: (6S, 8R)-1,3-Dichloro-8-methyl-4-oxo-4,6,7,8-tetrahydro-pyrrolo[1,2-a]pyrazine-6,8-dicarboxylic acid 8-benzyl ester 6-methyl ester.

This compound was prepared as a light yellow solid in a procedure similar to that of Example 1, Steps A–E. $^1$HNMR (300 MHz, CDCl$_3$) δ 7.40 (m, 5H), 5.28 (q, 2H, J=12.1 Hz), 5.20 (m, 1H), 3.85 (s, 3H), 3.00 (dd, 1H, J=13.8, 10.2 Hz), 2.30 (dd, 1H, J=13.8, 3.6 Hz), 1.63 (s, 3H).

Step C: (6S, 8R)-1-Chloro-3-cyclobutylamino-8-methyl-4-oxo-4,6,7,8-tetrahydro-pyrrolo[1,2-a]pyrazine-6,8-dicarboxylic acid 8-benzyl ester 6-methyl ester.

This compound was prepared in a procedure similar to that of Example 1, Step F. $^1$HNMR (300 MHz, CDCl$_3$) δ 7.38–7.28 (m, 5H), 6.30 (br, 1H), 5.19 (q, 2H), 5.04 (dd, J=9.9 and 4.0 Hz, 1H), 4.50 (m, 1H), 3.82 (s, 3H), 2.92 (dd, J=13.5 and 9.9 Hz, 1H), 2.44 (m, 2H), 2.24 (dd, J=13.6 and 4.0 hz, 1H), 1.97 (m, 2H), 1.77 (m, 2H), 1.64 (s, 3H).

Step D: (6S, 8R)-1-Chloro-3-cyclobutylamino-8-hydroxymethyl-8-methyl-4-oxo-4,6,7,8-tetrahydro-pyrrolo[1,2-a]pyrazine-6-carboxylic acid methyl ester.

A solution of the compound (155 mg) obtained from Step B in EtOAC (20 mL) and 10% Pd/C (30 mg) was hydrogenated under a hydrogen ballon for 2.0 h. Filtration and evaporation of solvent gave the corresponding acid in quantitative yield. To the acid (144 mg, 0.4 mmol) in THF (4.0 mL) at −20° C. was added Et$_3$N (0.069 mL, 1.25 eq) and ethyl chloroformate (0.045 mL, 1.15 eq). The mixture was stirred at −10° C. for 30 min. The precipitae was filtered. The filtrate was cooled back to −50° C., and NaBH$_4$ (45 mg, 3.0 eq) was added, followed by addition of methanol (2.0 mL). The mixture was stirred at −50° C. for 45 min before it was quenched by addition of 5% citric acid. Extraction with EtOAc, drying over MgSO$_4$ and evaporation of solvent gave practically pure product (110 mg, 80%) as white solid. $^1$HNMR (300 MHz, CDCl$_3$) δ 6.20 (br, 1H), 4.95 (dd, 1H, J=9.9, 4.8 Hz), 4.42 (m, 1H), 4.13 (d, 1H, J=11.0 Hz), 3.80 (s, 3H), 3.5 (d, 1H, J=1.0 Hz), 2.81 (dd, 1H, J=13.2, 9.9 Hz), 2.4 (m, 2H), 1.95 (m, 2H), 1.78 (m, 3H), 1.38 (s, 3H). MS, m/e 341 (M+H).

Step E: (6S, 8R)-1-Chloro-3-cyclobutylamino-8-hydroxymethyl-8-methyl-4-oxo-4,6,7,8-tetrahydro-pyrrolo[1,2-a]pyrazine-6-carboxylic acid.

This compound was prepared in a procedure similar to that of Example 1, Step G. $^1$HNMR (300 MHz, DMSO-d$_6$) δ 7.64 (d, J=7.7 Hz, 1H), 5.00 (s, br, 1H), 4.76 (dd, J=9.9 and 5.0 Hz, 1H), 4.27 (m, 1H), 3.71 (d, br, 1H), 3.42 (d, br, 1H), 2.72 (m, 1H), 2.49–2.03 (m, 4H), 1.82 (dd, J=13.2 and 5.1 Hz, 1H), 1.24 (s, 3H).

Step F: (6S,8R)-[(4-{[(1-Chloro-3-cyclobutylamino-8-hydroxymethyl-8-methyl-4-oxo-4,6,7,8-tetrahydro-pyrrolo[1,2-a]pyrazine-6-carbonyl)-amino]-methyl}-phenyl)-iminomethyl]-carbamic acid benzyl ester.

This compound was prepared in a procedure similar to that of Example 1, Step H. $^1$HNMR (300 MHz, CD$_3$OD) δ 7.83 (d, J=8.0, 2H), 7.48–7.29 (m, 7H), 5.20 (s, 2H), 4.91 (dd, J=9.5 and 4.8 Hz, 1H), 4.45 (m, 3H), 3.96 (d, J=11.0 Hz, 1H), 3.49 (d, J=11.3 Hz, 1H), 2.76 (dd, J=13.2 and 9.2 Hz, 1H), 2.38 (m, 2H), 2.03–1.93 (m, 3H), 1.77 (m, 2H), 1.39 (s, 3H).

Step G: Example 13.

This compound was prepared in a procedure similar to that of Example 1, Step I. $^1$HNMR (300 MHz, DMSO-d$_6$) δ 9.34 (s, 2H), 9.03 (m, br, 3H), 7.78 (d, J=8.4 Hz, 2H), 7.52 (d, J=8.4 Hz, 2H), 4.89 (dd, 1H), 4.55–4.25 (m, 3H), 3.82 (s, br), 3.74 (d, J=10.3 Hz, 1H), 3.38 (d, J=10.6 Hz, 1H), 2.68 (m, 1H), 2.26–2.04 (m, 4H), 1.79 (dd, 1H), 1.66 (m, 2H), 1.28 (s, 3H). MS m/e 459(M+1).

Example 14

(6S,8R)-8-Amino-1-chloro-8-methyl-4-oxo-3-(3-trifluoromethyl-benzylamino)-4,6,7,8-tetrahydro-pyrrolo[1,2-a]pyrazine-6-carboxylic acid 4-carbamimidoyl-benzylamide

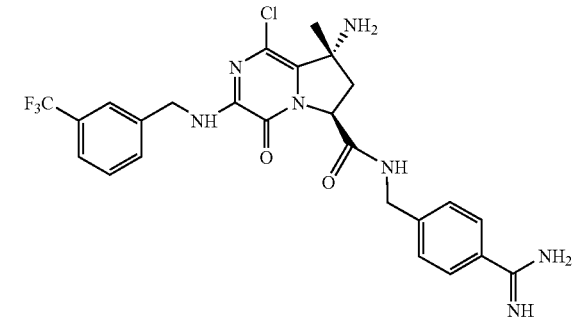

Step A: (6S,8R)-8-Benzyloxycarbonylamino-1-chloro-8-methyl-4-oxo-3-(3-trifluoromethyl-benzyloxy)-4,6,7,8-tetrahydro-pyrrolo[1,2-a]pyrazine-6-carboxylic acid.

In a flask (6S,8R)-8-benzyloxycarbonylamino-1-chloro-8-methyl-4-oxo-3-(3-trifluoromethyl-benzyloxy)-4,6,7,8-tetrahydro-pyrrolo[1,2-a]pyrazine-6-carboxylic acid ethyl ester (50 mg, 0.0862 mmol) was dissolved in THF (800 μL)

and 2 drops MeOH and cooled to 0° C. Lithium hydroxide (260 μL, 0.259 mmol) 1.0 M in water was added and the mixture allowed to stir for approximately 2 h at 0° C. TLC indicated complete reaction. The mixture was diluted with EtOAc and 5% citric acid was added. The mixture was separated and the aqueous layer extracted 1× with EtOAc. The organics were dried with $Na_2SO_4$ filtered and concentrated to give the product as a white solid (47 mg, 99% yield). $^1$HNMR (300 MHz, $CD_3OD$) δ 1.6(s, 3H) 2.25 (m, 1H) 2.95(m, 1H) 4.63 (s, 2H) 5.05 (m, 2H) 7.25–7.8 (m, 9H)

Step B: (6S,8R)-[6-[4-(Benzyloxycarbonylamino-imino-methyl)-benzylcarbamoyl]-1-chloro-8-methyl-4-oxo-3-(3-trifluoromethyl-benzylamino)-4,6,7,8-tetrahydro-pyrrolo[1,2-a]pyrazin-8-yl]-carbamic acid benzyl ester.

In a flask was placed the compound (43 mg, 0.078 mmol) obtained from Step A, PyAOP (51 mg, 0.0975 mmol), and the [(4-aminomethyl-phenyl)-imino-methyl]-carbamic acid benzyl ester (31 mg, 0.0859 mmol). The reactants were dissolved in DMF (0.8 mL) at room temperature and DIEA (68 μL, 0.390 mmol) was added. The reaction was allowed to stir for approximately 4 h. The solution was diluted with EtOAc and 5% $NaHCO_3$ was added and let stir for about 10 min. The phases were separated and the aqueous phase extracted 2× with EtOAc. The organics were concentrated and purified by HPLC to give the product as a white solid (48 mg, 59% yield). $^1$HNMR (300 MHz, $CD_3OD$) δ 1.65 (s, 3H) 2.2 (m, 1H) 3.1 (m, 1H) 4.65 (m, 4H) 5.0 (m, 2H) 5.05 (m, 1H) 5.43 (s, 2H) 7.25–7.9 (m, 18H).

Step C: Example 14.

The compound (34 mg, 0.0325 mmol) obtained from Step B was dissolved in MeOH (0.5 mL) and 10% Pd/C (7 mg) was added. A hydrogen balloon was attached and the reaction allowed to stir for approximately 4 h at which time MS indicated a complete reaction. The reaction was filtered and concentrated under vacuum to give the product as a white solid (20 mg, 79% yield). $^1$HNMR (300 MHz, $CD_3OD$) δ 1.56 (s, 3H) 2.25 (m, 1H) 2.45 (m, 1H) 4.5 (m, 2H) 4.6 (m, 2H) 5.1 (m, 1H) 7.5–7.8 (m, 8H).

Example 15

(3S)-[8-Acetyl-3-(4-carbamimidoyl-benzylcarbamoyl)-5-oxo-1,2,3,5-tetrahydro-indolizin-6-yl]-carbamic acid benzyl ester

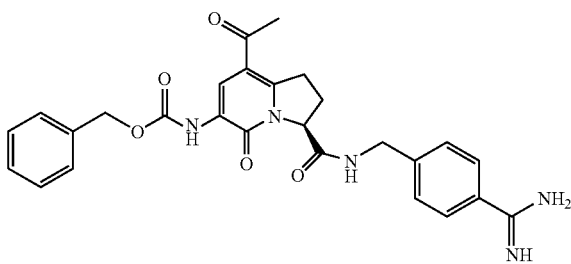

Step A: (2S)-1-(2-tert-Butoxycarbonyl-2-diazo-acetyl)-5-oxo-pyrrolidine-2-carboxylic acid methyl ester.

In a flask methyl(s)-(+)-2 pyrrolidone-5-carboxylate (1.0 g, 6.99 mmol) was dissolved in 40 mL THF and cooled to −78° C. LHMDS (8.0 mL, 8.0 mmol) 1.0M in THF was added and the reaction stirred at −78° C. for 25 mins. The chlorocarbonyl-diazo-acetic acid tert-butyl ester (1.7 g, 8.39 mmol, *J. Org. Chem.* 1994, 59, 1418) was then slowly added and the reaction stirred at −78° C. for 1.5 h, quenched at −78° C. with 5% citric acid and let warm to room temperature. Diluted with EtOAc, seperated, extracted 2× with EtOAc, washed with brine, and dried with magnesium sulfate. Concentrated under vacuum and purified by flash chromatography (10–30% EtOAc/hexanes) to give the product as a viscous yellow oil (1.1 g, 65%). $^1$HNMR (300 MHz, $CDCl_3$) δ 1.51 (s, 9H) 2.1(m, 1H) 2.2–2.8 (m, 3H) 3.79 (s, 3H) 4.74 (dd, 1H, J 4.0 8.8).

Step B: (3S)-8-Acetyl-5-oxo-1,2,3,5-tetrahydro-indolizine-3,6-dicarboxylic acid 6-tert-butyl ester 3-methyl ester.

In a flack the compound (1.1 g, 5.52 mmol) obtained from Step A was dissolved in 40 mL benzene and methyl vinyl ketone (1.3 mL, 15.4 mmol) and $[Rh(OAc_2)]_2$ (3 mg) were added. The reaction was heated to 90° C. for 6 h and TLC showed a complete conversion. Let cool to room temperature and added p-TsOH (130 mg, 0.678 mmol) and then heated to 50° C. overnight. Let the reaction cool to room temperature and concentrated to remove solvent. Diluted with EtOAc and washed with 5% $NaHCO_3$, brine, and dried with $MgSO_4$. Concentrated and purified by flash chromatography to give the product (605 mg, 38%).

The alcohol obtained above (605 mg, 1.71 mmol) was dissolved in pyridine, $POCl_3$ was added at room temperature and the reaction allowed to stir overnight. Concentrated under vacuum. Diluted with EtAOc and washed with 5% citric acid, saturated aqueous $CuSO_4$, and brine. Dried with $MgSO_4$, concentrated and purified by flash chromatography to give the product (279 mg, 49%). $^1$HNMR (300 MHz, $CDCl_3$) δ 1.6 (m, 9H) 2.5–2.7 (m, 5H) 3.6–3.9 (m, 5H) 5.3 (dd, 1H, J=3.1 10.1) 8.99(s, 1H).

Step C: (3S)-8-Acetyl-6-benzyloxycarbonylamino-5-oxo-1,2,3,5-tetrahydro-indolizine-3-carboxylic acid methyl ester.

The t-butylester (279 mg, 0.832 mmol) obtained from Step B was dissolved in 2.3 mL EtOAc and treated with 4.0M HCl/dioxane (2.1 mL, 8.32 mmol). Let stir 3 h at room temperature. Concentrated under vacuum to give the acid (230 mg, 99%). The acid (230 mg, 0.824 mmol) was dissolved in 8 mL THF and cooled to −20° C. To this solution was added NMM (136 μL, 1.24 mmol) followed by slow addition of EtOCOCl (87 μL, 0.906 mmol) and let stir for 40 mins at −20° C. The reaction was allowed to warm to −5° C. and $NaN_3$ (134 mg, 2.06 mmol) in 600 μL water was added and allowed to stir for 40 min. Diluted with EtAOc, washed with brine, dried with $MgSO_4$, concentrated. The concentrate was dissolved in 10 mL toluene and heated to 70° C. for 0.5 h and let cool. Benzyl alcohol (256 μL, 2.47 mmol) and p-TsOH (13 mg, 0.0659 mmol) were added and the reaction heated to 85° C. for 40 mins. Let cool to rt and stirred overnight. Solvent was removed under vacuum and the remaining material taken up in EtOAC, washed with 5% $NaHCO_3$ and brine. Dried with $MgSO_4$, concentrated and purified by flash chromatography (25–50% EtAOc/hexanes) to give the product (68 mg, 21%). $^1$HNMR (300 MHz, $CDCl_3$) δ 2.3–2.6 (m, 5H) 3.5(m, 1H) 3.7(m, 1H) 3.8 (s, 3H) 5.18 (dd, 1H, J=3.3 9.9 Hz), 7.4 (m, 5H) 7.67 (bs, 1H) 8.62 (bs, 1H). MS m/e 385.3 [M+H].

Step D: (3S)-8-Acetyl-6-benzyloxycarbonylamino-5-oxo-1,2,3,5-tetrahydro-indolizine-3-carboxylic acid.

The methyl ester (68 mg, 0.177 mmol) was dissolved in 1.3 mL THF and cooled to 0° C. Lithium hydroxide (440 μL, 0.442 mmol) 11.0M in water was added and the mixture allowed to stir for approximately 2 h at 0° C. TLC indicated complete reaction. The mixture was diluted with EtOAc and 5% citric acid was added. The mixture was separated and the aqueous layer extracted 1× with EtOAc. The organics were dried with sodium sulfate, filtered and concentrated to give the product as a white solid (43 mg, 66% yield). ¹HNMR (300 MHz, CD₃OD) δ 2.2–2.4 (m, 1H) 2.487 (s, 3H) 2.6 (m, 1H) 3.4 (m, 1H) 3.65 (m, 1H) 5.15 (dd, 1H, J 2.7 10.1) 5.22(s, 2H) 7.3–7.5 (m, 5H) 8.47 (BS, 1H) 8.62 (br, 1H).

Step E: (3S)-{8-Acetyl-3-[4-(tert-butoxycarbonylamino-imino-methyl)-benzylcarbamoyl]-5-oxo-1,2,3,5-tetrahydro-indolizin-6-yl}-carbamic acid benzyl ester.

The acid (43 mg, 0.116 mmol) obtained from Step D was placed in a flask with [(4-aminomethyl-phenyl)-imino-methyl]-carbamic acid tert-butyl ester (32 mg, 0.128 mmol), PyAOP (76 mg, 0.145 mmol) and dissolved in 2 mL DMF. DIEA (61 μL, 0.348 mmol) was added and the reaction allowed to stir for 2 h. The reaction was diluted with EtOAc and 5% NaHCO₃ was added and stirred for 10 min. The phases were separated and the aqueous phase extracted 2× with EtOAc, dried with sodium sulfate and concentrated. Purified by HPLC and lyopholized to give the product as a white solid (34 mg, 41% yield). ¹HNMR (300 MHz, CDCl₃) δ 1.614 (s, 9H) 2.3 (m, 1H) 2.5 (s, 3H) 2.6 (m, 1H) 3.4–3.6 (m, 2H) 3.6–3.8 (m, 2H) 5.2 (m, 1H) 5.25 (s, 2H) 7.4 (m, 9H) 7.6 (m, 2H) 7.8 (m, 2H).

Step F: Example 15.

The compound (22 mg, 0.116 mmol) obtained from Step E was dissolved in CH₂Cl₂ and treated with TFA (180 μL, 2.32 mmol). Let stir 2 h at room temperature. Concentrated under vacuum, lyopholized to give a white solid (18 mg). ¹HNMR (300 MHz, CD₃OD) δ 2.49 (s, 3H) 3.2–3.4 (m, 2H) 4.6–4.9 (m, 2H) 5.2 (m, 1H), 5.25 (s, 2H) 7.3–7.5 (m, 9H), 7.6 (m, 2H) 7.8 (m, 2H). MS m/e 502.4 [M+H].

Example 17

4-Carbamimidoyl-N-(1-chloro-3-cyclobutylamino-4-oxo-4,6,7,8-tetrahydro-pyrrolo[1,2-a]pyrazin-6-ylmethyl)-benzamide hydrochloride

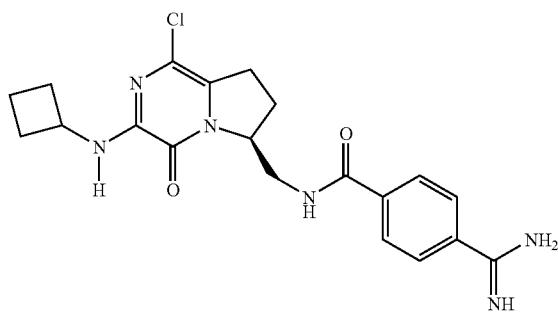

Step A: 1-Chloro-3-cyclobutylamino-6-hydroxymethyl-7,8-dihydro-6H-pyrrolo[1,2-a]pyrazin-4-one.

To a solution of the intermediate (90 mg, 0.31 mmol) obtained in Step G of Example 1 at −20° C. in THF (3.0 mL) was added triethyl amine (0.055 mL, 0.4 mmol) and ethyl chloroformate (0.035 mL, 0.37 mmol). The mixture was stirred at −20° C. for 30 min. The precipitate was filtered. The filtrate was cooled back to −50° C., and NaBH₄ (36 mg, 0.95 mmol) was added, followed by addition of methanol (2.0 mL). The mixture was stirred at −50° C. for 45 min before it was quenched by addition of 5% citric acid. Extraction with EtOAc, drying over MgSO₄ and evaporation of solvent gave practically pure product (86 mg) as white solid used directly for the next Step.

Step B: 6-Azidomethyl-1-chloro-3-cyclobutylamino-7,8-dihydro-6H-pyrrolo[1,2-a]pyrazin-4-one.

To the alcohol (86 mg, 0.32 mmol) obtained above in CH₂Cl₂ at 0° C. was added methanesulfonyl chloride (0.037 mL, 0.48 mmol) and triethyl amine (0.067 mL, 0.48 mmol). The mixture was stirred at 0° C. for 1.0 h before it was quenched with 5% citric acid. Extraction with EtOAc, drying over MgSO₄ and evaporation of solvent gave practically pure product used directly for next Step.

To the sulfonate (0.319 mmol) obtained above in DMF was added NaN₃ (104 mg, 1.6 mmol). The mixture was heated at 70° C. for 3 h. It was diluted with EtOAc, washed with brine. The organic layers were dried over MgSO₄. A column chromatography gave the desired product as white solid (51 mg, 51% for 2 Steps).

Step C: ({4-[(1-Chloro-3-cyclobutylamino-4-oxo-4,6,7,8-tetrahydro-pyrrolo[1,2-a]pyrazin-6-ylmethyl)-carbamoyl]-phenyl}-imino-methyl)-carbamic acid benzyl ester.

A solution of the azide (50 mg) obtained above in methanol was hydrogenated over Pd/C (10%, 10 mg) for 2.0 h to give the desired amine in quantitative yield as a white solid. To a solution of the above amine (24 mg, 0.089 mmol) and 4-(benzyloxycarbonylamino-imino-methyl)-benzoic acid pentafluorophenyl ester (50 mg, 0.10 mmol) in DMF (1.0 mL) was added DIEA (0.031 mL, 0.178 mmol) and a catalytic amount of DMAP. The mixture was heated at 125° C. for 6 h. After HPLC purification the product was obtained as a white solid (16 mg).

Step D: Example 17.

The above intermediate (16 mg) dissolved in 0.1 M HCl/EtOAC (1.0 mL) was hydrogenated over Pd/C (10%, 10 mg) for 2.0 h to give the desired amine in quantitative yield as a white solid. ¹HNMR (300 MHz, methanol-d₄) δ 7.96 (d, 2H, J=8.1 Hz), 7.89 (d, 2 H, J=8.1 Hz), 4.40 (m, 1 H), 3.98 (m, 1 H), 3.70 (m, 1 H), 2.98 (m, 2 H), 2.4–1.6 (m, 10 H), HMS m/e 415 (M+H).

Example 18

1-Chloro-3-cyclobutylamino-4-oxo-4,6,7,8-tetrahydro-pyrrolo[1,2-a]pyrazine-6-carboxylic acid (1-amino-isoquinolin-6-ylmethyl)-amide

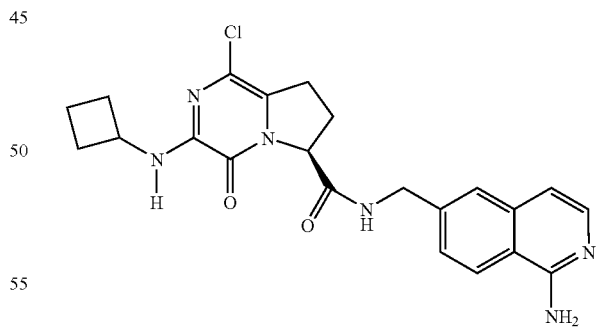

To (6S)-1-chloro-3-cyclobutyl-4-oxo-4,6,7,8-tetrahydro-pyrrolo[1,2a]pyrazine-6-carboxylic acid (68 mg, 0.24 mmol (obtained from Step G, Example 1), in a mixture of CH₂Cl₂/DMF (1.8/0.6 mL) was added Et₃N (0.1 mL, 0.72 mmol), HOAt (2 mg), EDCI (55 mg, 0.288 mmol) and 6-aminomethyl-isoquinolin-1-ylamine dihydrochloride (71 mg, 0.288 mmol, Bioorg. & Med. Chem. Lett. 1999, 9, 685–690). The mixture was stirred at rt overnight. Extraction with EtOAc, drying with MgSO₄ and evaporation of solvent gave crude product which was further purified by column chromatography (CH$_2$Cl$_2$/methanol) to give a white solid as product. $^1$HNMR (300 MHz, DMSO-d$_6$) δ 8.91 (t, 1 H, J=5.4 Hz), 8.11 (d, 1 H, J=8.5 Hz), 7.77 (d, 1 H, J=5.9 Hz), 7.58 (d, 1 H, J=8.0 Hz), 7.52 (s, 1 H), 7.33 (d, 1 H, J=8.4 Hz), 6.80 (d, 1 H, J=5.9 Hz), 6.7 (s, 1 H), 5.0 (d, 1 H, J=6.9 Hz), 4.4 (m, 3 H), 2.82 (m, 2 H), 2.1 (m, 5 H), 1.6 (m, 2 H). MS m/e 439 [M+H].

Example 19

1-Chloro-3-cyclobutylamino-8,8-dimethyl-4-oxo-4,6,7,8-tetrahydro-pyrrolo[1,2-a]pyrazine-6-carboxylic acid (1-amino-isoquinolin-6-ylmethyl)-amide

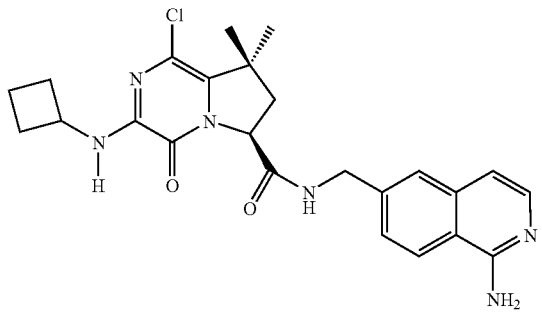

In a similar procedure to that of Example 18, starting with (6S)-1-Chloro-3-cyclobutylamino-8,8-dimethyl-4-oxo-4,6,7,8-tetrahydro-pyrrolo[1,2-a]pyrazine-6-carboxylic acid (obtained from Step D, Example 10), the title compound was obtained as a white solid. $^1$HNMR (300 MHz, DMSO-d$_6$) δ 8.89 (t, 1 H, J=5.9 Hz), 8.12 (d, 1 H, J=8.4 Hz), 7.77 (d, 1 H, J=5.50 Hz), 7.58 (d, 1 H, J=8.0 Hz), 7.55 (s, 1 H), 7.35 (d, 1 H, J=8.8 Hz), 6.85 (d, 1 H, J=5.5 Hz), 6.72 (s, 1 H), 4.94 (dd, 1 H, J=9.9, 4.1 Hz), 4.4 (m, 3 H), 2.1 (m, 5 H), 1.6 (m, 2 H), 1.37 (s, 3 H), 1.33 (s, 3 H). MS m/e 467 [M+H].

Example 20

1-Chloro-8,8-diethyl-4-oxo-3-(3-phenyl-propylamino)-4,6,7,8-tetrahydro-pyrrolo[1,2-a]pyrazine-6-carboxylic acid (1-amino-isoquinolin-6-ylmethyl)-amide

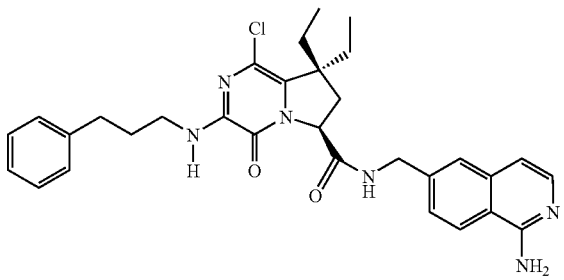

In a procedure similar to that of Example 18, the title compound was prepared as a white solid. $^1$HNMR (300 MHz, methanol-d$_4$) δ 9.05 (t, 1 H, J=5.9 Hz), 8.38 (d, 1 H, J=8.4 Hz), 8.00 (s, 1 H), 7.78 (d, 1 H, J=8.00 Hz), 7.52 (d, 1 H, J=6.9 Hz), 7.22 (m, 6 H), 4.8–4.9 (m, 2 H), 4.56 (m, 1 H), 3.40 (t, 3 H, J=9.3 Hz), 2.64 (t, 2 H, J=9.3 Hz), 2.41 (m, 1 H), 2.20 (m, 1 H), 1.98 (m, 4 H), 1.68 (m, 1 H), 0.90 (t, 3 H, J=7.86 Hz), 0.86 (t, 3 H, J=7.86 Hz). MS m/e 559 [M+H].

Example 56

(6S, 8R)-1-Chloro-3-cyclobutylamino-8-ethyl-4-oxo-4,6,7,8-tetrahydro-pyrrolo[1,2-a]pyrazine-6-carboxylic acid-4-carbamimidoyl-benzylamide

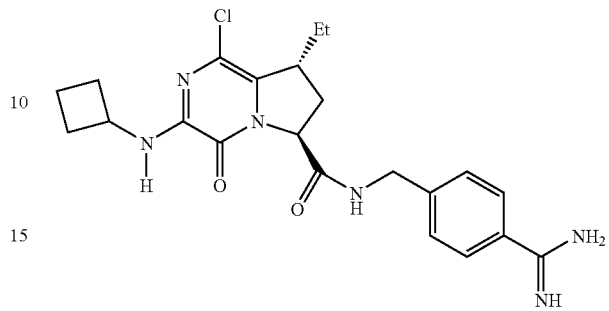

Step A: (3R, 5S)-5-(tert-Butyl-diphenyl-silanyloxymethyl)-3-ethyl-2-oxo-pyrrolidine-1-carboxylic acid tert-butyl ester.

To a solution of (5S)-5-(tert-Butyl-diphenyl-silanyloxymethyl)-2-oxo-pyrrolidine-1-carboxylic acid tert-butyl ester (5.0 g, 11.0 mmol) in THF (50 mL) at −78° C. was added LHMDS (1.0 M in THF, 12.6 mL, 12.6 mmol). The mixture was stirred for 30 min before ethyl triflate (1.78 mL, 1.25 equiv.) was added. The reaction was stirred between −78° C. to −40° C. for 45 min. It was quenched with 5% citric acid at −50° C., extracted with ethyl acetate. The combined organic phases were washed with 5% NaHCO$_3$, brine, and dried over MgSO$_4$NaHCO$_3$, brine, and dried over MgSO$_4$. Evaporation of the solvent and flash column chromatography (hexanes/EtOAc, 4:1) gave the desired product (90% yield) as viscous oil. $^1$HNMR (400 MHz, CDCl$_3$) δ 7.63 (m, 4 H), 7.41 (m, 6 H), 4.13 (m, 2 H), 3.86 (m, 1 H), 3.74 (d, 1 H), 2.71 (m, 1 H), 2.24 (t, 1 H), 1.95 (m, 1 H), 1.78 (q, 1 H), 1.46 (s, 9 H), 0.95 (t, 3 H).

Step B: (3R, 5S)-3-Ethyl-5-hydroxymethyl-2-oxo-pyrrolidine-1-carboxylic acid tert-butyl ester.

To a solution of the compound obtained from step A (5.2 g, 10.8 mmol) in THF (20 mL) and acetic acid (1.36 mL, 2.2 equiv.) at 0° C. was added TBAF (1.0 M in THF, 17.8 mL, 1.65 equiv). The mixture was stirred at rt for 2.0 h. It was then diluted with ethyl acetate and washed with 5% KHSO$_4$ and brine. Evaporation of solvent and a column chromatography (EtOAc: hexane=1:1) gave the desired product as viscous oil (yield, 95%). $^1$HNMR (400 MHz, CDCl$_3$) δ 4.11 (m, 1 H), 3.78 (dd, 2 H), 2.63 (m, 1 H), 2.15 (dd, 1 H), 1.99 (m, 1 H), 1.82 (m, 1 H), 1.55 (s, 9 H), 1.54 (m, 1 H), 0.97 (t, 3 H).

Step C: (3R, 5S)-4-Ethyl-5-oxo-pyrrolidine-1,2-dicarboxylic acid 1-tert-butyl ester.

To a solution of the compound obtained in step B (2.46 g, 10.1 mmol) in a mixture of CH$_3$CN/CCl$_4$/water (1:1:2, 60 mL) was added NaIO$_4$ (6.49 g, 3.0 equiv), followed by RuCl$_3$ (105 mg, 0.05 equiv). The mixture was stirred at rt for 2.0 h. It was diluted with CH$_2$Cl$_2$ and organic layer was collected. Evaporation of solvent and a column purification (EtOAc: MeOH=15:1) gave the desired product as a solid (70% yield). M/e 258 (M+H).

Step D: (3R, 5S)-4-Ethyl-5-oxo-pyrrolidine-1,2-dicarboxylic acid 1-tert-butyl ester 2-methyl ester.

To a solution of the compound obtained from step C (1.48 g, 5.75 mmol) in a mixture of methanol (5.0 mL) and benzene (15 mL) was added trimethylsilyldiazomethane (2.0 M in hexane, 4.89 mL, 1.7 equiv.). The mixture was stirred at rt for 45 min. After evaporation of solvent, the product was obtained as viscous oil (yield, 99%). $^1$HNMR (400 MHz, CDCl$_3$) δ 4.57 (dd, 1 H), 3.78 (s, 3 H), 2.56 (m, 1 H), 2.05 (dd, 1 H), 1.95 (m, 2 H), 1.50 (s, 9 H), 1.49 (m, 1 H), 0.96 (t, 3 H).

Step E: Example 56.

In procedures similar to these in Example 1, the title compound was obtained as a white solid. $^1$HNMR (400 MHz, methanol-d$_4$) δ 7.76 (d, 2 H), 7.56 (d, 2 H), 4.90 (dd, 1 H), 4.39 (m, 2 H), 3.00–1.78 (m, 12 H), 0.93 (t, 3 H). MS m/e 443 [M+H].

Example 57

(6S, 8R)-1-Chloro-3-cyclobutylamino-8-ethyl-4-oxo-4,6,7,8-tetrahydro-pyrrolo[1,2-a]pyrazine-6-carboxylic acid (1-amino-isoquinolin-6-ylmethyl)-amide

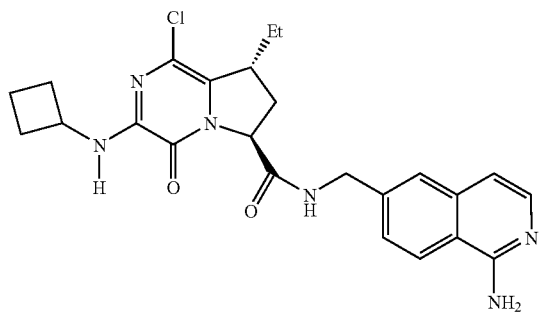

The title compound was prepared in a similar procedure to that of Example 18. $^1$HNMR (400 MHz, methanol-d$_4$) δ 8.10 (m, 1 H), 7.8 (d, 1 H), 7.56 (m, 1 H), 7.7.35 (d, 1 H), 7.15 (t, 1 H), 4.95 (dd, 1 H), 4.60–4.20 (m, 3 H), 2.6–1.90 (m, 12 H), 1.58 (t, 3 H). MS m/e 467 [M+H].

Example 58

1-Chloro-3-cyclobutylamino-8-ethyl-4-oxo-4,6,7,8-tetrahydro-pyrrolo[1,2-a]pyrazine-6-carboxylic acid 4-aminomethyl-benzylamide

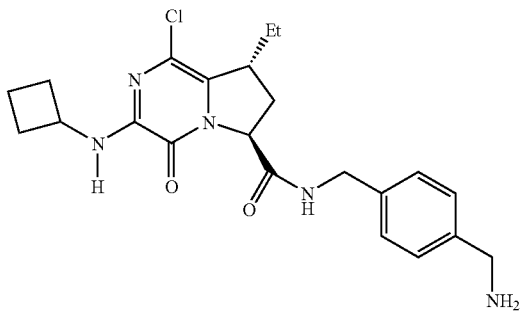

The title compound was prepared as a white solid following a procedure similar to that of Example 1, but using (4-aminomethyl-benzyl)-carbamic acid tert-butyl ester in the coupling step. $^1$HNMR (400 MHz, methanol-d$_4$) δ 7.42 (4 H), 4.42 (m, 3 H), 4.01 (s, 2 H), 3.29 (t, 1 H), 2.67 (t, 1 H), 2.30–1.70 (m, 9 H), 0.94 (t, 3 H). MS m/e 452 [M+Na].

Parallel Synthesis of Compound 5E:

The following compounds summarized in Table 1 were prepared according to chemistry outlined in Scheme 5. Benzyl ester 5A was prepared similarly to that of ethyl ester exemplified in Example 1, Step E. It reacted with a primary amine in EtOAc at temperature ranging from rt to 70° C. to give 5B. Hydrogenation of 5B gave the acid 5C in good yield. Coupling of the acid 5C to the 4-amidinobenzyl amine, followed by a reductive removal of the Cbz protecting group gave the final compound 5E for testing. This sequence allowed a more rapid parallel synthesis.

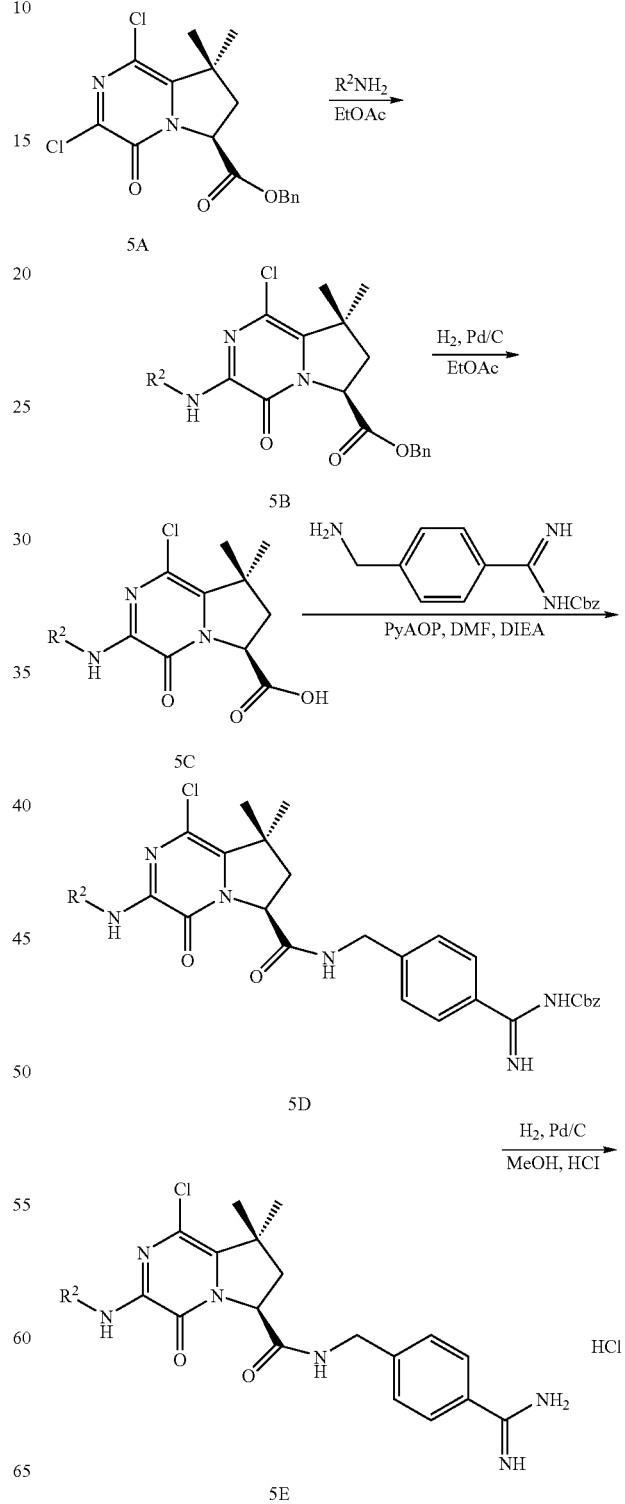

Scheme 5

Various analogs synthesized using Schemes and methods disclosed herein are listed in the Table 1 below.

TABLE 1

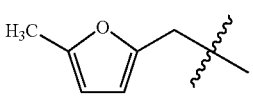

| # | Name | R² | MS (M + 1) |
|---|------|----|-----------| 
| 21 | (6S)-1-chloro-8,8-dimethyl-3-[(5-methyl-furan-2-ylmethyl)-amino]-4-oxo-4,6,7,8-tetrahydro-pyrrolo[1,2-a]pyrazine-6-carboxylic acid 4-carbamimidoyl-benzylamide | 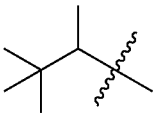 | 483 |
| 22 | (6S)-1-chloro-8,8-dimethyl-4-oxo-3-(1,2,2-trimethyl-propylamino)-4,6,7,8-tetrahydro-pyrrolo[1,2-a]pyrazine-6-carboxylic acid 4-carbamimidoyl-benzylamide | 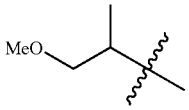 | 473 |
| 23 | (6S)-1-chloro-3-(2-methoxy-1-methyl-ethylamino)-8,8-dimethyl-4-oxo-4,6,7,8-tetrahydro-pyrrolo[1,2-a]pyrazine-6-carboxylic acid 4-carbamimidoyl-benzylamide | 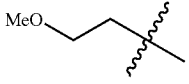 | 447 |
| 24 | (6S)-1-chloro-3-(2-methoxy-ethylamino)-8,8-dimethyl-4-oxo-4,6,7,8-tetrahydro-pyrrolo[1,2-a]pyrazine-6-carboxylic acid 4-carbamimidoyl-benzylamide | 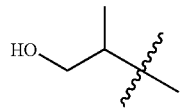 | 432 |
| 25 | (6S)-1-chloro-3-(2-hydroxy-1-methyl-ethylamino)-8,8-dimethyl-4-oxo-4,6,7,8-tetrahydro-pyrrolo[1,2-a]pyrazine-6-carboxylic acid 4-carbamimidoyl-benzylamide | 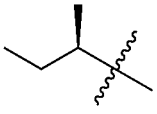 | 418 |
| 26 | (6R)-3-sec-butylamino-1-chloro-8,8-dimethyl-4-oxo-4,6,7,8-tetrahydro-pyrrolo[1,2-a]pyrazine-6-carboxylic acid 4-carbamimidoyl-benzylamide | 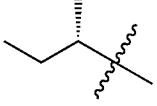 | 445 |
| 27 | (6S)-3-sec-butylamino-1-chloro-8,8-dimethyl-4-oxo-4,6,7,8-tetrahydro-pyrrolo[1,2-a]pyrazine-6-carboxylic acid-4-carbamimidoyl-benzylamide | 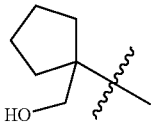 | 445 |
| 28 | (6S)-1-chloro-3-(1-hydroxymethyl-cyclopentylamino)-8,8-dimethyl-4-oxo-4,6,7,8-tetrahydro-pyrrolo[1,2-a]pyrazine-6-carboxylic acid 4-carbamimidoyl-benzylamide | 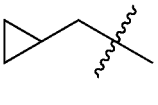 | 487 |
| 29 | (6S)-1-chloro-3-(cyclopropylmethyl-amino)-8,8-dimethyl-4-oxo-4,6,7,8-tetrahydro-pyrrolo[1,2-a]pyrazine-6-carboxylic acid 4-carbamimidoyl-benzylamide | | 443 |

TABLE 1-continued

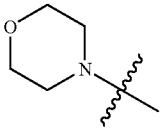

| # | Name | R² | MS (M + 1) |
|---|---|---|---|
| 30 | (6S)-1-chloro-8,8-dimethyl-3-(morpholin-4-ylamino)-4-oxo-4,6,7,8-tetrahydro-pyrrolo[1,2-a]pyrazine-6-carboxylic acid 4-carbamimidoyl-benzylamide | 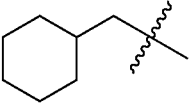 | 474 |
| 31 | (6S)-3-(3-amino-propylamino)-1-chloro-8,8-dimethyl)-4-oxo-4,6,7,8-tetrahydro-pyrrolo[1,2-a]pyrazine-6-carboxylic acid 4-carbamimidoyl-benzylamide | NH₂(CH₂)₃— | 446 |
| 32 | (6S)-1-chloro-3-(cyclohexylmethyl-amino)-8,8-dimethyl-4-oxo-4,6,7,8-tetrahydro-pyrrolo[1,2-a]pyrazine-6-carboxylic acid 4-carbamimidoyl-benzylamide |  | 485 |
| 33 | (6S)-3-tert-butylamino-1-chloro-8,8-dimethyl-4-oxo-4,6,7,8-tetrahydro-pyrrolo[1,2-a]pyrazine-6-carboxylic acid 4-carbamimidoyl-benzylamide | t-Bu | 445 |
| 34 | (6S)-1-chloro-3-(N',N'-dimethyl-hydrazino)-8,8-dimethyl-4-oxo-4,6,7,8-tetrahydro-pyrrolo[1,2-a]pyrazine-6-carboxylic acid 4-carbamimidoyl-benzylamide | Me₂N— | 432 |
| 35 | (6S)-1-chloro-3-isobutylamino-8,8-dimethyl-4-oxo-4,6,7,8-tetrahydro-pyrrolo[1,2-a]pyrazine-6-carboxylicacid 4-carbamimidoyl-benzylamide | i-Bu | 445 |
| 36 | (6S)-1-chloro-8,8-dimethyl-4-oxo-3-(3-phenyl-propylamino)-4,6,7,8-tetrahydro-pyrrolo[1,2-a]pyrazine-6-carboxylic acid 4-carbamimidoyl-benzylamide | Ph(CH₂)₃— | 507 |
| 37 | (6S)-1-chloro-3-ethylamino-8,8-dimethyl-4-oxo-4,6,7,8-tetrahydro-pyrrolo[1,2-a]pyrazine-6-carboxylic acid 4-carbamimidoyl-benzylamide | Et | 417 |
| 38 | (6S)-1-chloro-3-isopropylamino-8,8-dimethyl-4-oxo-4,6,7,8-tetrahydro-pyrrolo[1,2-a]pyrazine-6-carboxylic acid 4-carbamimidoyl-benzylamide | i-Pr | 431 |
| 39 | (6S)-1-chloro-8,8-dimethyl-3-methylamino-4-oxo-4,6,7,8-tetrahydro-pyrrolo[1,2-a]pyrazine-6-carboxylic acid 4-carbamimidoyl-benzylamide | Me | 403 |
| 40 | (6S)-1-chloro-8,8-dimethyl-4-oxo-3-phenethylamino-4,6,7,8-tetrahydro-pyrrolo[1,2-a]pyrazine-6-carboxylic acid 4-carbamimidoyl-benzylamide | Ph(CH₂)₂— | 493 |
| 41 | (6S)-1-chloro-3-[2-(4-hydroxy-phenyl)-ethylamino]-8,8-dimethyl-4-oxo-4,6,7,8-tetrahydro-pyrrolo[1,2-a]pyrazine-6-carboxylic acid 4-carbamimidoyl]-benzylamide | 4-OH-Ph(CH₂)₂— | 509 |

TABLE 1-continued

| # | Name | R² | MS (M + 1) |
|---|------|----|-----------| 
| 42 | (6S)-3-amino-1-chloro-8,8-dimethyl-4-oxo-4,6,7,8-tetrahydro-pyrrolo[1,2-a]pyrazine-6-carboxylic acid 4-carbamimidoyl-benzylamide | H | 389 |

Additional compounds prepared according to the chemistry illustrated in the above Schemes and in specific Example sections are summarized in Table 2.

TABLE 2

| # | R⁵ | R⁴ | Name | R² | MS (M + H) |
|---|----|----|------|----|-----------|
| 43 | H | H | (6S)-1-chloro-3-methylamino-4-oxo-4,6,7,8-tetrahydro-pyrrolo[1,2-a]pyrazine-6-carboxylic acid 4-carbamimidoyl-benzylamide | Me | 375 |
| 44 | H | H | (6S)-1-chloro-3-isopropylamino-4-oxo-4,6,7,8-tetrahydro-pyrrolo[1,2-a]pyrazine-6-carboxylic acid 4-carbamimidoyl-benzylamide | i-Pr | 403 |
| 45 | H | H | (6S)-1-chloro-3-ethylamino-4-oxo-4,6,7,8-tetrahydro-pyrrolo[1,2-a]pyrazine-6-carboxylic acid 4-carbamimidoyl-benzylamide | Et | 389 |
| 46 | Et | Et | (6S)-1-chloro-3-cyclobutylamino-8,8-diethyl-4-oxo-4,6,7,8-tetrahydro-pyrrolo[1,2-a]pyrazine-6-carboxylic acid 4-carbamimidoyl-benzylamide | cyclobutyl | 471 |
| 47 | Et | Et | (6S)-1-chloro-3-cyclopropylamino-8,8-diethyl-4-oxo-4,6,7,8-tetrahydro-pyrrolo[1,2-a]pyrazine-6-carboxylic acid 4-carbamimidoyl-benzylamide | cyclopropyl | 457 |
| 48 | Et | Et | (6S)-1-chloro-8,8-diethyl-3-ethylamino-4-oxo-4,6,7,8-tetrahydro-pyrrolo[1,2-a]pyrazine-6-carboxylic acid 4-carbamimidoyl-benzylamide | Et | 445 |
| 49 | Et | Et | (6S)-1-chloro-8,8-diethyl-3-isopropylamino-4-oxo-4,6,7,8-tetrahydro-pyrrolo[1,2-a]pyrazine-6-carboxylic acid 4-carbamimidoyl-benzylamide | i-Pr | 459 |
| 50 | Et | Et | (6S)-1-chloro-8,8-diethyl-4-oxo-3-(3-phenyl-propylamino)-4,6,7,8-tetrahydro-pyrrolo[1,2-a]pyrazine-6-carboxylic acid 4-carbamimidoyl-benzylamide | Ph(CH₃)₂— | 535 |
| 51 | Me | Pr | (6S, 8R)-1-chloro-8-methyl-4-oxo-3-(3-phenyl-propylamino)-8-propyl-4,6,7,8-tetrahydro-pyrrolo[1,2-a]pyrazine-6- | cyclobutyl | 471 |

TABLE 2-continued

| # | R⁵ | R⁴ | Name | R² | MS (M+H) |
|---|----|----|------|-----|----------|
| 52 | Pr | Pr | (6S)-1-chloro-3-cyclobutylamino-4-oxo-8,8-dipropyl-4,6,7,8-tetrahydro-pyrrolo[1,2-a]pyrazine-6-carboxylic acid 4-carbamimidoyl-benzylamide | cyclobutyl | 499 |
| 53 | Pr | Pr | (6S)-1-chloro-3-ethylamino-4-oxo-8,8-dipropyl-4,6,7,8-tetrahydro-pyrrolo[1,2-a]pyrazine-6-carboxylic acid 4-carbamimidoyl-benzylamide | Et | 473 |
| 54 | Me | CONHMe | (6S, 8R)-1-chloro-3-cyclobutylamino-8-methyl-4-oxo-4,6,7,8-tetrahydro-pyrrolo[1,2-a]pyrazine-6,8-dicarboxylic acid 6-(4-carbamimidoyl-benzylamide) 8-methylamide | cyclobutyl | 486 |
| 55 | Me | CONHBn | (6S, 8R)-1-chloro-3-cyclobutylamino-8-methyl-4-oxo-4,6,7,8-tetrahydro-pyrrolo[1,2-a]pyrazine-6,8-dicarboxylic acid 8-benzylamide 6-(4-carbamimidoyl-benzylamide) | cyclobutyl | 562 |

Utility

The compounds of the present invention are inhibitors of factor VIIa and are useful as anticoagulants for the prevention or treatment of thromboembolic disorders in mammals. In general, a thromboembolic disorder is a circulatory disease caused by blood clots (i.e., diseases involving fibrin formation, platelet activation, and/or platelet aggregation). The term "thromboembolic disorders" as used herein includes arterial or venous cardiovascular or cerebovascular thromboembolic disorders, and thromboembolic disorders in the chambers of the heart. The term "thromboembolic disorders" as used herein also includes specific disorders selected from, but not limited to, unstable angina or other acute coronary syndromes, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary and cerebral arterial thrombosis, cerebral embolism, kidney embolisms, pulmonary embolisms, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g. after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of serine proteases involved in the coagulation cascade, more specifically, inhibition of the coagulation factors: factor VIIa, factor IXa, factor Xa, factor XIa or thrombin.

The effectiveness of compounds of the present invention as inhibitors of the coagulation factors VIIa, IXa, Xa, XIa, or thrombin, can be determined using a relevant purified serine protease, respectively, and an appropriate synthetic substrate. The rate of hydrolysis of the chromogenic substrate by the relevant serine protease was measured both in the absence and presence of compounds of the present invention. Hydrolysis of the substrate resulted in the release of pNA, which was monitored spectrophotometrically by measuring the increase in absorbance at 405 nM, or the release of AMC (amino methylcoumarin, which was monitored spectrofluorometrically by measuring the increase in emission at 460 nM with excitation at 380 nM. A decrease in the rate of absorbance change at 405 nM in the presence of inhibitor is indicative of enzyme inhibition. Such methods are known to one skilled in the art. The results of this assay are expressed as inhibitory constant, $K_i$.

Factor VIIa determinations were made in 0.007 M calcium chloride, 0.1 M sodium chloride, 0.05 M trizma base containing 0.1% human serum albumin at a pH of 7.4. Determinations were made using purified human factor VIIa (Heamatologic Technologies Inc., Essex Jct., Vt.) at a final assay concentration of 2–5 nM, soluble tissue factor at a concentration of 28 nM and the synthetic substrate S-2288 (Chromogenix) at a concentration of 0.001 M. Compounds tested in the assay for Factor VIIa are considered to be active if they exhibit a $K_i$ of equal to or less than 25 μM. Preferred compounds of the present invention have $K_i$'s of equal to or less than 1 μM. More preferred compounds of the present invention have $K_i$'s of equal to or less than 0.1 μM. Even more preferred compounds of the present invention have $K_i$'s of equal to or less than 0.01 μM. Compounds of the present invention have demonstrated $K_i$ values of equal to or less than 25 μM in the assay for Factor VIa, thereby confirming the utility of the compounds of the present invention as effective inhibitors of coagulation factor VIa.

Factor IXa determinations were made in 0.005 M calcium chloride, 0.1 M sodium chloride, 0.05 M trizma base and 0.5% Carbowax PEG 8000 at a pH of 7.4. Determinations were made using purified human factor IXa (Haematologic Technologies) at a final assay concentration of 50–100 nM and the synthetic substrate PCIXA2100-B (CenterChem) at a concentration of 0.0002–0.0004 M. Compounds tested in the factor IXa assay are considered to be active if they exhibit a $K_i$ of equal to or less than 25 μM.

Factor Xa determinations were made in 0.1 M sodium phosphate buffer at a pH of 7.4 containing 0.2 M sodium chloride and 0.5% Carbowax PEG 8000. Determinations of the Michaelis constant, Km, for substrate hydrolysis were made using purified human factor Xa (Heamatologic Technologies Inc., Essex Jct., Vt.) at a final assay concentration of 0.5 nM and the synthetic substrate S-2222 (Chromogenix)

at a concentration of 0.0002–0.0004 M. Compounds tested in the factor Xa assay are considered to be active if they exhibit a $K_i$ of equal to or less than 25 µM.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using factor XIa at a final concentration of 75–200 µM (Haematologic Technologies) and the synthetic substrate S-2366 (Chromogenix) at a concentration of 0.0002–0.00025 M. Compounds tested in the factor XIa assay are considered to be active if they exhibit a $K_i$ of equal to or less than 25 µM.

Thrombin determinations were made in 0.1 M sodium phosphate buffer at a pH of 7.4 containing 0.2M sodium chloride and 0.5% Carbowax PEG 8000. Determinations were made using purified human alpha Thrombin (Heamatologic Technologies Inc., Essex Jct., Vt.) at a final assay concentration of 0.25 nM and the synthetic substrate S-2366 (Chromogenix) at a concentration of 0.0002 M. Compounds tested in the thrombin assay are considered to be active if they exhibit a $K_i$ of equal to or less than 25 µM.

Compounds of the present invention have demonstrated $K_j$ values of equal to or less than 25 µM in at least one of the above assays, thereby confirming the utility of the compounds of the present invention as effective inhibitors of the coagulation cascade and useful as anticoagulants for the prevention or treatment of thromboembolic disorders in mammals.

The Michaelis constant, Km, for substrate hydrolysis by each protease was determined at 25° C. using the method of Lineweaver and Burk. Values of $K_i$ were determined by allowing the protease to react with the substrate in the presence of the inhibitor. Reactions were allowed to go for periods of 20–180 minutes (depending on the protease) and the velocities (rate of absorbance change vs. time) were measured. The following relationship was used to calculate $K_i$ values:

$$(v_o-v_s)/v_s = I/(K_i(1+S/K_m)) \text{ for a competitive inhibitor with one binding site; or}$$

$$v_s/v_o = A + ((B-A)/1 + ((IC_{50}/(I)^n))) \text{ and}$$

$$K_i = IC_{50}/(1+S/K_m) \text{ for a competitive inhibitor}$$

where:
$v_o$ is the velocity of the control in the absence of inhibitor;
$v_s$ is the velocity in the presence of inhibitor;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme:inhibitor complex;
S is the concentration of substrate; and
$K_m$ is the Michaelis constant.

The effectiveness of compounds of the present invention as inhibitors of the coagulation factors XIa, VIIa, IXa, Xa, or thrombin, can be determined using relevant in vivo thrombosis models, including In Vivo Electrically-induced Carotid Artery Thrombosis Models and In Vivo Rabbit Arterio-venous Shunt Thrombosis Models.

In Vivo Electrically-induced Carotid Artery Thrombosis Model:

The antithrombotic effect of compounds of the present invention can be demonstrated in the electrically-induced carotid artery thrombosis (ECAT) model in rats. In this model, rats are anesthetized with a mixture of ketamine (110 mg/kg i.m.) and xylazine (10 mg/kg i.m.). A femoral vein and a femoral artery are isolated and catheterized. The carotid artery is also isolated such that its blood flow can be measured with a calibrated flow probe that is linked to a flowmeter. A stainless steel bipolar hook electrode is placed on the carotid artery and positioned caudally in relationship to the flow probe as a means of applying electrical stimulus. In order to protect the surrounding tissue, a piece of Parafilm is placed under the electrode.

Test compounds are considered to be effective as anticoagulants based on their ability to maintain blood flow in the carotid artery following the induction of thrombosis by an electrical stimulus. A test compound or vehicle is given as continuous intravenous infusion via the femoral vein, starting 1 h before electrical stimulation and continuing to the end of the test. Thrombosis is induced by applying a direct electrical current of 4 mA for 3 min to the external arterial surface, using a constant current unit and a d.c. stimulator. The carotid blood flow is monitored and the time to occlusion (decrease of blood flow to zero following induction of thrombosis) in minutes is noted. The change in observed blood flow is calculated as a percentage of the blood flow prior to induction of thrombosis and provides a measure of the effect of a test compound when compared to the case where no compound is administered. This information is used to estimate the $ED_{50}$ value, the dose that increases blood flow to 50% of the control (blood flow prior to induction of thrombosis) and is accomplished by nonlinear least square regression.

In Vivo Rabbit Arterio-venous Shunt Thrombosis Model:

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After 40 min, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The ID50 values (dose which produces 50% inhibition of thrombus formation) are estimated by linear regression.

The compounds of Formula (I) may also be useful as inhibitors of serine proteases, notably human thrombin, plasma kallikrein and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention may be shown to be direct acting inhibitors of the serine protease thrombin by their ability to inhibit the cleavage of small molecule substrates by thrombin in a purified system. In vitro inhibition constants may be determined by the method described by Kettner et al. in *J. Biol. Chem.* 1990, 265, 18289–18297, herein incorporated by reference. In these assays, thrombin-mediated hydrolysis of the chromogenic substrate S2238 (Helena Laboratories, Beaumont, Tex.) are monitored spectrophotometrically. Addition of an inhibitor to the assay mixture results in decreased absorbance and is indicative of thrombin inhibition. Human thrombin (Heamatologic Technologies Inc., Essex Jct., Vt.) at a concentration of 0.2 nM in 0.10 M sodium phosphate buffer, pH 7.5, 0.20 M NaCl, and 0.5% PEG 6000, is incubated with various substrate concentrations ranging from 0.20 to 0.02 mM. After 25 to 30 min of incubation, thrombin activity is assayed by monitoring the rate of increase in absorbance at 405 nm that arises owing to substrate hydrolysis. Inhibition constants are derived from reciprocal plots of the reaction velocity as a function of substrate concentration using the standard method of Lineweaver and Burk.

The compounds of the present invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of Formula (I) that, when administered alone or in combination with an additional therapeutic agent to a mammal, is effective to treat (i.e. prevent, inhibit or ameliorate) the thromboembolic disease condition or treat the progression of the disease in a host.

The compounds of the invention are preferably administered alone to a mammal in a therapeutically effective amount. However, the compounds of the invention can also be administered in combination with an additional therapeutic agent, as define below, to a mammal in a therapeutically effective amount. When administered in a combination, the combination of compounds is preferably, but not necessarily, a synergistic combination. Synergy, as described for example by Chou and Talalay, *Adv. Enzyme Regul.* 1984, 22, 27–55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

By "administered in combination" or "combination therapy" it is meant that the compound of Formula (I) and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Compounds which can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin, low molecular weight heparin (for example LOVANOX™), as well as other factor VIIa, VIIIa, IXa, Xa, XIa, prothrombin, TAFI, and fibrinogen inhibitors known in the art.

The term anti-platelet agents (or platelet inhibitory agents), as used herein, denotes agents that inhibit platelet function such as by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam are preferred. Other suitable anti-platelet agents include clopidrogel and ticlopidine, including pharmaceutically acceptable salts or prodrugs thereof. Ticlopidine is also a preferred compound since it is known to be gentle on the gastro-intestinal tract in use. Still other suitable platelet inhibitory agents include IIb/IIIa antagonists, thromboxane-A2-receptor antagonists and thromboxane-A2-synthetase inhibitors, prostacyclin mimetics, phosphodiesterase (PDE) inhibitors, such as dipyridamole or cilostazol, serotonin-2-receptor antagonists, and P2Y1 and P2Y12 receptor antagonists, as well as pharmaceutically acceptable salts or prodrugs thereof.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boroarginine derivatives and boropeptide thrombin inhibitors include those disclosed in PCT Application Publication Number 92/07869 and European Patent Application Publication Number 471,651 A2, the disclosures of which are hereby incorporated herein by reference.

The term thrombolytics (or fibrinolytic) agents (or thrombolytics or fibrinolytics), as used herein, denotes agents that lyse blood clots (thrombi). Such agents include tissue plasminogen activator (TPA), anistreplase, urokinase, streptokinase, PAI-I inhibitors, and inhibitors of α-2-antiplasmin, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

The term hypolipidemic agents, as used herein, includes HMG-CoA reductase inhibitors (for example, pravastatin, simvastatin, atorvastatin, and the like) and microsomal triglyceride transport protein inhibitors.

The term antihypertensive agents, as used herein, includes angiotensin-converting enzyme inhibitors (for example captopril, lisinopril, or fosinopril), angiotensin-II receptor antagonists (for example irbestatin, losartan, or valsartan), ACE/NEP inhibitors (for example omapatrilat or gemopatrilat) and β-blockers (for example propanolol, nadolo, or carvedilol).

Administration of the compounds of Formula (I) of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the inhibition of factor VIIa, IXa, Xa and/or XIa. Such compounds may be provided in a commercial kit, for example, for use in pharmaceutical research involving factor VIIa, IXa, Xa and/or XIa. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor VIIa, IXa, Xa, and/or XIa. For example, the presence of factor VIIa, IXa, Xa and/or XIa in an unknown sample could be determined by addition of the relevant chromogenic substrate, example S2222 for factor Xa, to a series of solutions containing test sample and optionally one of the compounds of the present invention. If production of pNA is observed in the solutions containing test sample, but not in the presence of a compound of the present invention, then one would conclude factor Xa was present.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about 1 to 3 milligrams of antiplatelet agents, per kilogram of patient body weight.

Where the compounds of Formula I are administered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

What is claimed is:

1. A compound of Formula (Ia):

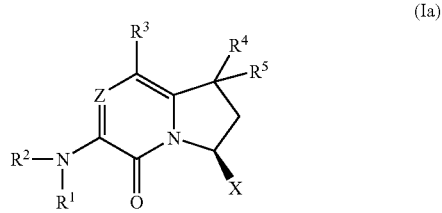

or a stereoisomer or pharmaceutically acceptable salt form thereof, wherein:

X is —C(=O)NH—CH$_2$—R$^8$, —S(=O)$_2$NH—CH$_2$—R$^8$, —CR$^{15}$R$^{15}$—NHC(=O) —CH$_2$—R$^8$, or —CR$^{15}$R$^{15}$—NHS(=O)$_2$—CH$_2$—R$^8$;

Z is N;

R$^1$ is H, methyl, ethyl, propyl, or butyl;

R² is H, —C(═O)R²ᵃ, —C(═O)OR²ᵃ, —C(═O)NHR²ᵃ, —S(═O)R²ᵃ, —S(═O)₂R²ᵃ, —S(═O)₂NHR²ᵃ, C₁–C₆ alkyl substituted with 0–3 R²ᵇ, C₂–C₆ alkenyl substituted with 0–3 R²ᵇ, C₂–C₆ alkynyl substituted with 0–3 R²ᵇ, C₃–C₆ carbocycle substituted with 0–3 R²ᶜ, aryl substituted with 0–3 R²ᶜ, or 5–6 membered heterocycle consisting of carbon atoms and 1–4 heteroatoms selected from the group: O, S, and N, and substituted with 0–3 R²ᶜ;

each R²ᵃ is, independently at each occurrence, H, C₁–C₆ alkyl substituted with 0–2 R²ᵇ, C₂–C₆ alkenyl substituted with 0–2 R²ᵇ, C₂–C₆ alkynyl substituted with 0–2 R²ᵇ, C₃–C₆ carbocycle substituted with 0–3 R²ᶜ, aryl substituted with 0–3 R²ᶜ, or 5–6 membered heterocyclic group consisting of carbon atoms and 1–4 heteroatoms selected from the group: O, S, and N; and said 5–6 membered heterocyclic group is substituted with 0–3 R²ᶜ;

provided when R² is —S(═O)R²ᵃ or —S(═O)₂R²ᵃ, then R²ᵃ is not H;

each R²ᵇ is, independently at each occurrence, H, F, Cl, Br, I, NO₂, CN, —NCS, CF₃, —OCF₃, CH₃, —CH₂CH₃, —OCH₃, ═O, OH, CO₂H, NH₂, —NH(CH₃), N(CH₃)₂, —CO₂R²¹, —C(═O)NR²¹R²¹, —NHC(═O)R²¹, —NR²¹R²¹, —NHSO₂R²¹, —SO₂R²¹, —SO₂NR²¹R²¹, —OR²¹ᵃ, —SR²¹ᵃ, —C(═O)R²¹ᵃ, —S(═O)R²¹ᵃ, C₁–C₄ haloalkyl, C₁–C₄ haloalkoxy, C₃–C₆ carbocycle substituted with 0–3 R²ᶜ, aryl substituted with 0–3 R²ᶜ, or 5–6 membered heterocycle consisting of carbon atoms and 1–4 heteroatoms selected from the group: O, S, and N, and substituted with 0–3 R²ᶜ;

each R²ᶜ is, independently at each occurrence, H, F, Cl, Br, I, NO₂, CN, —NCS, CF₃, —OCF₃, CH₃, —OCH₃, ═O, OH, CO₂H, NH₂, NH(CH₃), N(CH₃)₂, —CO₂R²¹, —C(═O)NR²¹R²¹, —NHC(═O)R²¹, —NR²¹R²¹, —NHSO₂R²¹, —SO₂R²¹, —SO₂NR²¹R²¹, —OR²¹ᵃ, —SR²¹ᵃ, —C(═O)R²¹ᵃ, —S(═O)R²¹ᵃ, C₁–C₄ haloalkyl, C₁–C₄ haloalkoxy, or C₁–C₄ alkyl;

R³ is selected from the group: Cl, Br, NO₂, CN, CF₃, C₁–C₄ alkyl, OH, CO₂H, —CO₂(C₁–C₄ alkyl), NH₂, —NH(C₁–C₄ alkyl), —N(C₁–C₄ alkyl)₂, —C(═O)NH₂, —C(═O)NH(C₁–C₄ alkyl), —C(═O)N(C₁–C₄ alkyl)₂, —SO₂(C₁–C₄ alkyl), —NHC(═O)H, —NHC(═O)(C₁–C₄ alkyl), —C(═O)H, and —C(═O)(C₁–C₄ alkyl);

R⁴ is selected from the group: H, halogen, CF₃, —OCF₃, OH, CN, NO₂, —OR²², —SR²², —NR²²R²³, —C(═O)R²², —C(═O)NR²²R²³, —NR²⁴C(═O)R²², —NR²⁴C(═O)NR²²R²³, —NR²⁴C(═O)NR²⁴C(═O)R²², —C(═O)OR²², —OC(═O)R²², —OC(═O)OR²², —NR²⁴C(═O)OR²², —OC(═O)NR²²R²³, —S(═O)R²², —S(═O)₂R²², —S(═O)NR²²R²³, —S(═O)₂NR²²R²³, —NR²⁴S(═O)₂NR²²R²³, —NR²⁴S(═O)R²², —NR²⁴S(═O)₂R²², C₁–C₄ haloalkyl, C₁–C₆ alkoxy, (C₁–C₄ haloalkyl)oxy, C₁–C₆ alkyl, C₂–C₆ alkenyl, C₂–C₆ alkynyl, and C₁–C₄ alkyl substituted with R⁴ᵃ;

R⁴ᵃ is selected from the group: —NR²²R²³, —C(═O)NR²²R²³, —NR²⁴C(═O)R²², —NR²⁴C(═O)NR²²R²³, —NR²⁴C(═O)NR²⁴C(═O)R²², —C(═O)OR²², —NR²⁴C(═O)OR²², —NR²⁴S(═O)₂NR²²R²³, —NR²⁴S(═O)₂R²², OH, and phenyl substituted with 0–2 R²⁶;

R⁵ is selected from the group: H, halo, C₁–C₄ haloalkyl, C₁–C₄ alkyl, C₂–C₄ alkenyl, and C₂–C₄ alkynyl;

R⁸ is phenyl substituted with one R⁸ᵃ and 0–1 R⁸ᵇ, naphthyl substituted with one R⁸ᵃ and 0–1 R⁸ᵇ, quinolinyl substituted with one R⁸ᵃ and 0–1 R⁸ᵇ, or isoquinolinyl substituted with one R⁸ᵃ and 0–1 R⁸ᵇ;

each R⁸ᵃ is, independently at each occurrence, —C(═NH)NH₂, —C(═O)NH₂, —NHC(═NH)NH₂, —NHCH(═NH), NH₂, —CH₂C(═NH)NH₂, —CH₂NHC(═NH)NH₂, —CH₂NHCH(═NH), —CH₂NH₂, or —CH₂C(═O)NH₂;

each R⁸ᵇ is, independently at each occurrence, H, halogen, C₁–C₄ alkyl, C₁–C₄ alkoxy, OH, CF₃, —OCF₃, CN, NO₂, —C(═O)NH₂, NH₂, —NH(C₁–C₃ alkyl), or —N(C₁–C₃ alkyl)₂;

each R¹⁵ is, independently at each occurrence, H, F, or methyl;

alternatively, —CR¹⁵R¹⁵— forms a gem disubstituted cyclopropyl group;

each R²¹ is, independently at each occurrence, H, C₁–C₄ alkyl, aryl, or aryl(C₁–C₃ alkyl)-;

each R²¹ᵃ is, independently at each occurrence, H, C₁–C₄ alkyl, aryl, aryl(C₁–C₃ alkyl)-, or C₁–C₄ haloalkyl;

each R²² is, independently at each occurrence, H, C₁–C₄ alkyl, C₂–C₄ alkenyl, C₃–C₆ cycloalkyl, phenyl substituted with 0–5 R²⁶, benzyl substituted with 0–5 R²⁶, or 5–6 membered heterocycle containing from 1–4 heteroatoms selected from the group consisting of N, O, and S, and substituted with 0–3 R²⁶;

provided when R⁴ or R⁴ᵃ are —OC(═O)OR²², —S(═O)R²², —S(═O)₂R²², —NR²⁴S(═O)R²², or —NR²⁴S(═O)₂R²², then R²² is not H;

each R²³ is, independently at each occurrence, H or C₁–C₄ alkyl;

alternatively, R²² and R²³, when attached to the same nitrogen, combine to form a 5–6 membered heterocycle consisting of one nitrogen atom, carbon atoms and 0–1 additional heteroatoms selected from the group consisting of —N(R²⁴)— and O;

each R²⁴ is, independently at each occurrence, H or C₁–C₄ alkyl; and each R²⁶ is, independently at each occurrence, H, OH, F, Cl, CN, NO₂, CF₃, —SO₂CH₃, —SO₂CH₂CH₃, NH₂, NH(CH₃), N(CH₃)₂, methyl, ethyl, propyl, allyl, —OCF₃, methoxy, ethoxy, —SCH₃, —SCH₂CH₃, —C(═O)CH₃, —C(═O)CH₂CH₃, —NHC(═O)CH₃, or —NHC(═O)CH₂CH₃.

2. A compound according to claim 1 of Formula (Ib):

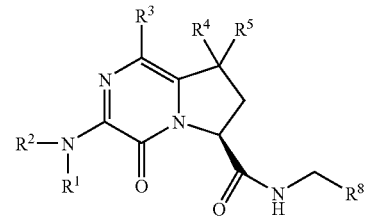

(Ib)

or a stereoisomer or pharmaceutically acceptable salt form thereof, wherein:

R¹ is H, methyl, or ethyl;

R² is H, —C(═O)R²ᵃ, —C(═O)OR²ᵃ, —S(═O)₂R²ᵃ, —NR²ᵃR²ᵃ, C₁–C₆ alkyl substituted with 0–1 R²ᵇ, C₂–C₆ alkenyl substituted with 0–1 R²ᵇ, C₂–C₆ alkynyl substituted with 0–1 R²ᵇ, C₃–C₆ carbocycle substituted with 0–3 R²ᶜ, aryl substituted with 0–3 R²ᶜ, or 5–6 membered heterocycle consisting of carbon atoms and 1–4 heteroatoms selected from the group: O, S, and N, and substituted with 0–3 $R^{2c}$;

each $R^{2a}$ is, independently at each occurrence, H, $C_1$–$C_6$ alkyl substituted with 0–1 $R^{2b}$, $C_2$–$C_6$ alkenyl substituted with 0–1 $R^{2b}$, $C_2$–$C_6$ alkynyl substituted with 0–1 $R^{2b}$, $C_3$–$C_6$ carbocycle substituted with 0–3 $R^{2c}$, aryl substituted with 0–3 $R^{2c}$, or 5–6 membered heterocycle consisting of carbon atoms and 1–4 heteroatoms selected from the group: O, S, and N, and substituted with 0–3 $R^{2c}$;

provided when $R^2$ is —S(=O)$R^{2a}$ or —S(=O)$_2R^{2a}$, then $R^{2a}$ is not H;

each $R^{2b}$ is, independently at each occurrence, H, F, Cl, Br, I, $NO_2$, CN, —NCS, $CF_3$, —$OCF_3$, —$SCH_3$, —$SCH_2CH_3$, —$SCF_3$, $CH_3$, —$CH_2CH_3$, —$CH(CH_3)_2$, —$OCH_3$, —$OCH_2CH_3$, =O, OH, $CO_2H$, $NH_2$, NH($CH_3$), N($CH_3$)$_2$, —NH($CH_2CH_3$), —N($CH_2CH_3$)$_2$, $CO_2H$, —$CO_2CH_3$, —$CO_2CH_2CH_3$, —C(=O)H, —C(=O)$CH_3$, —C(=O)$CH_2CH_3$, —C(=O)$CF_3$, —S(=O)$CH_3$, —S(=O)$CH_2CH_3$, —C(=O)$NH_2$, —C(=O)NH($CH_3$), —C(=O)NH($CH_2CH_3$), —C(=O)N($CH_3$)$_2$, —C(=O)N($CH_2CH_3$)$_2$, —NHC(=O)H, —NHC(=O)$CH_3$, —NHC(=O)$CH_2CH_3$, —$NHSO_2$($CH_3$), —$NHSO_2$($CH_2CH_3$), —$SO_2CH_3$, —$SO_2CH_2CH_3$, —$SO_2NH_2$, —$SO_2$NH($CH_3$), —$SO_2$NH($CH_2CH_3$), $C_3$–$C_6$ carbocycle substituted with 0–3 $R^{2c}$, aryl substituted with 0–3 $R^{2c}$, or 5–6 membered heterocycle consisting of carbon atoms and 1–4 heteroatoms selected from the group: O, S, and N, and is substituted with 0–3 $R^{2c}$;

each $R^{2c}$ is, independently at each occurrence, H, F, Cl, $NO_2$, CN, $CF_3$, $CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$C(CH_3)_3$, $NH_2$, NH($CH_3$), N($CH_3$)$_2$, —NH($CH_2CH_3$), —N($CH_2CH_3$)$_2$, $CO_2H$, —$CO_2CH_3$, —$CO_2CH_2CH_3$, —C(=O)$NH_2$, —C(=O)NH($CH_3$), —C(=O)NH($CH_2CH_3$), —C(=O)N($CH_3$)$_2$, —C(=O)N($CH_2CH_3$)$_2$, —NHC(=O)H, —NHC(=O)$CH_3$, —NHC(=O)$CH_2CH_3$, —$NHSO_2$($CH_3$), —$NHSO_2$($CH_2CH_3$), —$SO_2CH_3$, —$SO_2CH_2CH_3$, —$SO_2NH_2$, —$SO_2$NH($CH_3$), —$SO_2$NH($CH_2CH_3$), OH, —$OCH_3$, —$OCH_2CH_3$, —$OCF_3$, —$SCH_3$, —$SCH_2CH_3$, —$SCF_3$, —C(=O)H, —C(=O)$CH_3$, —C(=O)$CH_2CH_3$, —C(=O)$CF_3$, —S(=O)$CH_3$, or —S(=O)$CH_2CH_3$;

$R^3$ is selected from the group: Cl, Br, $NO_2$, CN, $CF_3$, $CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$C(CH_3)_3$, OH, $CO_2H$, —$CO_2CH_3$, —$CO_2CH_2CH_3$, $NH_2$, NH($CH_3$), N($CH_3$)$_2$, —NH($CH_2CH_3$), —N($CH_2CH_3$)$_2$, —C(=O)$NH_2$, —C(=O)NH($CH_3$), —C(=O)NH($CH_2CH_3$), —C(=O)N($CH_3$)$_2$, —C(=O)N($CH_2CH_3$)$_2$, —NHC(=O)H, —NHC(=O)$CH_3$, —NHC(=O)$CH_2CH_3$, —$SO_2CH_3$, —$SO_2CH_2CH_3$, —C(=O)H, —C(=O)$CH_3$, and —C(=O)$CH_2CH_3$;

$R^4$ is H, F, Cl, Br, $CF_3$, $C_2$–$C_4$ haloalkyl, $C_1$–$C_6$ alkyl, $C_2$–$C_6$ alkenyl, $C_2$–$C_6$ alkynyl, —$NR^{22}R^{23}$, —$NR^{24}$C(=O)$R^{22}$, —$CH_2NR^{22}R^{23}$, —$CH_2$C(=O)$NR^{22}R^{23}$, —$CH_2NR^{24}$C(=O)$R^{22}$, —$CH_2NR^{24}$C(=O)$NR^{22}R^{23}$, —$CH_2$C(=O)$OR^{22}$, —$CH_2NR^{24}$C(=O)$OR^{22}$, —$CH_2NR^{24}S$(=O)$_2NR^{22}R^{23}$, —$CH_2NR^{24}S$(=O)$_2R^{22}$, —$C_1$–$C_4$ alkyl-(OH), or —$C_1$–$C_4$ alkyl-(aryl);

$R^5$ is H, methyl, ethyl, propyl, butyl, or allyl;

$R^8$ is phenyl substituted with —C(=NH)$NH_2$ and 0–1 $R^{8b}$;

$R^{8b}$ is H, F, Cl, Br, $CH_3$, —$OCH_3$, OH, $CF_3$, —$OCF_3$, CN, $NO_2$, —C(=O)$NH_2$, $NH_2$, NH($CH_3$), or N($CH_3$)$_2$;

each $R^{22}$ is, independently at each occurrence, H, methyl, ethyl, propyl, butyl, allyl, cyclopropyl, cyclobutyl, cyclopentyl, cyclohexyl, phenyl, pyridinyl, furanyl, thienyl, pyrrolyl, pyrazolyl, pyrazinyl, piperazinyl, piperidinyl, imidazolyl, imidazolidinyl, isoxazolyl, morpholinyl, oxazolyl, oxazolidinyl, or tetrahydrofuranyl;

provided when $R^4$ is —$CH_2NR^{24}S$(=O)$_2R^{22}$, then $R^{22}$ is not H;

each $R^{23}$ is, independently at each occurrence, H, methyl, ethyl, propyl, or butyl; and alternatively, $R^{22}$ and $R^{23}$, when attached to the same nitrogen, combine to form pyrrolidinyl, piperidinyl, morpholinyl, piperazinyl, or N-methylpiperazinyl; and each $R^{24}$ is, independently at each occurrence, H, methyl, ethyl, propyl, or butyl.

3. A compound according to claim 2 of Formula (Ic):

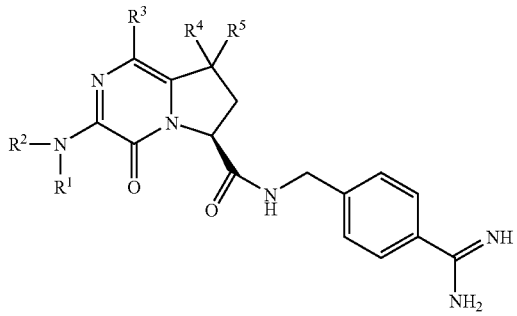

(Ic)

or a stereoisomer or pharmaceutically acceptable salt form thereof, wherein:

$R^1$ is H or methyl;

$R^2$ is H, —C(=O)$R^{2a}$, —C(=O)$OR^{2a}$, —S(=O)$_2R^{2a}$, N($CH_3$)$_2$, methyl, ethyl, propyl, butyl, pentyl, hexyl, propenyl, butenyl, pentenyl, cyclopropyl, cyclobutyl, cyclopentyl, cyclohexyl, methyl substituted with $R^{2b}$, ethyl substituted with $R^{2b}$, propyl substituted with $R^{2b}$, butyl substituted with $R^{2b}$, pentyl substituted with $R^{2b}$, propenyl substituted with 0–1 $R^{2b}$, butenyl substituted with 0–1 $R^{2b}$, pentenyl substituted with 0–1 $R^{2b}$, or phenyl substituted with 0–3 $R^{2c}$;

each $R^{2a}$ is, independently at each occurrence, methyl, ethyl, propyl, butyl, pentyl, hexyl, propenyl, butenyl, pentenyl, cyclopropyl, cyclobutyl, cyclopentyl, cyclohexyl, methyl substituted with $R^{2b}$, ethyl substituted with $R^{2b}$, propyl substituted with $R^{2b}$, butyl substituted with $R^{2b}$, pentyl substituted with $R^{2b}$, propenyl substituted with 0–1 $R^{2b}$, butenyl substituted with 0–1 $R^{2b}$, pentenyl substituted with 0–1 $R^{2b}$, or phenyl substituted with 0–3 $R^{2c}$;

each $R^{2b}$ is, independently at each occurrence, H, F, Cl, $NO_2$, CN, $CF_3$, $CH_3$, —$CH_2CH_3$, —$CH_2CH_2CH_3$, —$CH(CH_3)_2$, $NH_2$, NH($CH_3$), N($CH_3$)$_2$, —NH($CH_2CH_3$), —N($CH_2CH_3$)$_2$, $CO_2H$, —$CO_2CH_3$, —$CO_2CH_2CH_3$, —C(=O)$NH_2$, —C(=O)NH($CH_3$), —C(=O)NH($CH_2CH_3$), —C(=O)N($CH_3$)$_2$, —C(=O)N($CH_2CH_3$)$_2$, —NHC(=O)H, —NHC(=O)$CH_3$, —NHC(=O)$CH_2CH_3$, —$NHSO_2$($CH_3$), —$NHSO_2$($CH_2CH_3$), —$SO_2CH_3$, —$SO_2CH_2CH_3$, —$SO_2NH_2$, —$SO_2$NH($CH_3$), —$SO_2$NH($CH_2CH_3$), OH, —$OCH_3$, —$OCH_2CH_3$, —$OCF_3$, —$SCH_3$, —SCH₂CH₃, —SCF₃, —C(=O)H, —C(=O)CH₃, —C(=O)CH₂CH₃, —C(=O)CF₃, —S(=O)CH₃, —S(=O)CH₂CH₃, cyclopropyl, cyclobutyl, cyclopentyl, cyclohexyl, phenyl substituted with 0–3 $R^{2c}$, or furanyl substituted with 0–3 $R^{2c}$;

alternatively, $R^1$ and $R^2$ are combined to form morpholinyl or piperidinyl;

$R^4$ is H, F, methyl, ethyl, propyl, allyl, —$NR^{22}R^{23}$, —NHC(=O)$R^{22}$, —C(=O)NH$R^{22}$, —CH₂$NR^{22}R^{23}$, —CH₂C(=O)$NR^{22}R^{23}$, —CH₂NHC(=O)$R^{22}$, —CH₂NHC(=O)$NR^{22}R^{23}$, —CH₂C(=O)O$R^{22}$, —CH₂NHS(=O)₂$R^{22}$, —CH₂OH, —CH₂CH₂OH, benzyl, phenethyl, phenylpropyl, naphthylmethyl, naphthylethyl, or naphthylpropyl;

$R^5$ is H, methyl, ethyl, propyl, or allyl;

each $R^{22}$ is, independently at each occurrence, H, methyl, ethyl, propyl, allyl, cyclopropyl, cyclobutyl, cyclopentyl, cyclohexyl, phenyl, or benzyl;

provided when $R^4$ is —CH₂NHS(=O)₂$R^{22}$, then $R^{22}$ is not H;

$R^{23}$ is H, methyl, ethyl, propyl, or butyl; and alternatively, —$NR^{22}R^{23}$ forms piperidinyl.

4. A compound according to claim 1, wherein the compound is selected from the group:

(6S)-1-chloro-3-cyclobutylamino-4-oxo-4,6,7,8-tetrahydro-pyrrolo[1,2-a]pyrazine-6-carboxylic acid 4-carbamimidoyl-benzylamide hydrochloride;

(6S, 8R)-1-chloro-3-cyclobutylamino-4-oxo-8-(3-phenyl-propyl)-4,6,7,8-tetrahydro -pyrrolo[1,2-a]pyrazine-6-carboxylic acid 4-carbamimidoyl-benzylamide hydrochloride;

(6S, 8S)-1-chloro-3-cyclobutylamino-4-oxo-8-(3-phenyl-propyl)-4,6,7,8-tetrahydro-pyrrolo[1,2-a]pyrazine-6-carboxylic acid 4-carbamimidoyl-benzylamide hydrochloride;

(6S, 8R)-1-chloro-3-cyclobutylamino-8-(3-naphthalen-1-yl-propyl)-4-oxo-4,6,7,8-tetrahydro-pyrrolo[1,2-a]pyrazine-6-carboxylic acid 4-carbamimidoyl-benzylamide hydrochloride;

(6S, 8S)-1-chloro-3-cyclobutylamino-8-(3-naphthalen-1-yl-propyl)-4-oxo-4,6,7,8-tetrahydro-pyrrolo[1,2-a]pyrazine-6-carboxylic acid 4-carbamimidoyl-benzylamide hydrochloride;

(6S, 8R)-8-benzyl-1-chloro-3-cyclobutylamino-4-oxo-4,6,7,8-tetrahydro-pyrrolo[1,2-a]pyrazine-6-carboxylic acid 4-carbamimidoyl-benzylamide hydrochloride;

(6S, 8S)-8-benzyl-1-chloro-3-cyclobutylamino-4-oxo-4,6,7,8-tetrahydro-pyrrolo[1,2-a]pyrazine-6-carboxylic acid 4-carbamimidoyl-benzylamide hydrochloride;

(6S, 8R)-1-chloro-3-cyclobutylamino-8-naphthalen-2-yl-methyl-4-oxo-4,6,7,8-tetrahydro-pyrrolo[1,2-a]pyrazine-6-carboxylic acid 4-carbamimidoyl-benzylamide hydrochloride;

(6S, 8S)-1-chloro-3-cyclobutylamino-8-naphthalen-2-yl-methyl-4-oxo-4,6,7,8-tetrahydro-pyrrolo[1,2-a]pyrazine-6-carboxylic acid 4-carbamimidoyl-benzylamide hydrochloride;

(6S)-1-chloro-3-cyclobutylamino-8,8-dimethyl-4-oxo-4,6,7,8-tetrahydro-pyrrolo[1,2-a]pyrazine-6-carboxylic acid 4-carbamimidoyl-benzylamide trihydrochlroride;

(6S)-1-chloro-3-cyclopropylamino-8,8-dimethyl-4-oxo-4,6,7,8-tetrahydro-pyrrolo[1,2-a]pyrazine-6-carboxylic acid 4-carbamimidoyl-benzylamide hydrochloride;

(6S)-1-chloro-3-cyclopentylamino-8,8-dimethyl-4-oxo-4,6,7,8-tetrahydro-pyrrolo[1,2-a]pyrazine-6-carboxylic acid 4-carbamimidoyl-benzylamide hydrochloride;

(6S, 8R)-1-chloro-3-cyclobutylamino-8-hydroxymethyl-8-methyl-4-oxo-4,6,7,8-tetrahydro-pyrrolo[1,2-a]pyrazine-6-carboxylic acid 4-diaminomethyl-benzylamide hydrochloride;

(6S, 8R)-8-amino-1-chloro-8-methyl-4-oxo-3-(3-trifluoromethyl-benzylamino) -4,6,7,8-tetrahydro-pyrrolo[1,2-a]pyrazine-6-carboxylic acid 4-carbamimidoyl-benzylamide;

4-carbamimidoyl-N-(1-chloro-3-cyclobutylamino-4-oxo-4,6,7,8-tetrahydro-pyrrolo[1,2-a]pyrazin-6-ylmethyl)-benzamide hydrochloride;

1-chloro-3-cyclobutylamino-4-oxo-4,6,7,8-tetrahydro-pyrrolo[1,2-a]pyrazine-6-carboxylic acid (1-amino-isoquinolin-6-ylmethyl)-amide;

1-chloro-3-cyclobutylamino-8,8-dimethyl-4-oxo-4,6,7,8-tetrahydro-pyrrolo[1,2-a]pyrazine-6-carboxylic acid (1-amino-isoquinolin-6-ylmethyl)-amide;

1-chloro-8,8-diethyl-4-oxo-3-(3-phenyl-propylamino)-4,6,7,8-tetrahydro-pyrrolo[1,2-a]pyrazine-6-carboxylic acid (1-amino-isoquinolin-6-ylmethyl)-amide;

(6S)-1-chloro-8,8-dimethyl-3-[(5-methyl-furan-2-ylmethyl)-amino]-4-oxo-4,6,7,8-tetrahydro-pyrrolo[1,2-a]pyrazine-6-carboxylic acid 4-carbamimidoyl-benzylamide;

(6S)-1-chloro-8,8-dimethyl-4-oxo-3-(1,2,2-trimethyl-propylamino)-4,6,7,8-tetrahydro-pyrrolo[1,2-a]pyrazine-6-carboxylic acid 4-carbamimidoyl-benzylamide;

(6S)-1-chloro-3-(2-methoxy-1-methyl-ethylamino)-8,8-dimethyl-4-oxo-4,6,7,8-tetrahydro-pyrrolo[1,2-a]pyrazine-6-carboxylic acid 4-carbamimidoyl-benzylamide;

(6S)-1-chloro-3-(2-methoxy-ethylamino)-8,8-dimethyl-4-oxo-4,6,7,8-tetrahydro-pyrrolo[1,2-a]pyrazine-6-carboxylic acid 4-carbamimidoyl-benzylamide;

(6S)-1-chloro-3-(2-hydroxy-1-methyl-ethylamino)-8,8-dimethyl-4-oxo-4,6,7,8-tetrahydro-pyrrolo[1,2-a]pyrazine-6-carboxylic acid 4-carbamimidoyl-benzylamide;

(6R)-3-sec-butylamino-1-chloro-8,8-dimethyl-4-oxo-4,6,7,8-tetrahydro-pyrrolo[1,2-a]pyrazine-6-carboxylic acid 4-carbamimidoyl-benzylamide;

(6S)-3-sec-butylamino-1-chloro-8,8-dimethyl-4-oxo-4,6,7,8-tetrahydro-pyrrolo[1,2-a]pyrazine-6-carboxylic acid 4-carbamimidoyl-benzylamide;

(6S)-1-chloro-3-(1-hydroxymethyl-cyclopentylamino)-8,8-dimethyl-4-oxo-4,6,7,8-tetrahydro-pyrrolo[1,2-a]pyrazine-6-carboxylic acid 4-carbamimidoyl-benzylamide;

(6S)-1-chloro-3-(cyclopropylmethyl-amino)-8,8-dimethyl-4-oxo-4,6,7,8-tetrahydro-pyrrolo[1,2-a]pyrazine-6-carboxylic acid 4-carbamimidoyl-benzylamide;

(6S)-1-chloro-8,8-dimethyl-3-(morpholin-4-ylamino)-4-oxo-4,6,7,8-tetrahydro-pyrrolo[1,2-a]pyrazine-6-carboxylic acid 4-carbamimidoyl-benzylamide;

(6S)-3-(3-amino-propylamino)-1-chloro-8,8-dimethyl-4-oxo-4,6,7,8-tetrahydro-pyrrolo[1,2-a]pyrazine-6-carboxylic acid 4-carbamimidoyl-benzylamide;

(6S)-1-chloro-3-(cyclohexylmethyl-amino)-8,8-dimethyl-4-oxo-4,6,7,8-tetrahydro-pyrrolo[1,2-a]pyrazine-6-carboxylic acid 4-carbamimidoyl-benzylamide;

(6S)-3-tert-butylamino-1-chloro-8,8-dimethyl-4-oxo-4,6,7,8-tetrahydro-pyrrolo[1,2-a]pyrazine-6-carboxylic acid 4-carbamimidoyl-benzylamide;

(6S)-1-chloro-3-(N',N'-dimethyl-hydrazino)-8,8-dimethyl-4-oxo-4,6,7,8-tetrahydro-pyrrolo[1,2-a]pyrazine-6-carboxylic acid 4-carbamimidoyl-benzylamide;

(6S)-1-chloro-3-isobutylamino-8,8-dimethyl-4-oxo-4,6,7,8-tetrahydro-pyrrolo[1,2-a]pyrazine-6-carboxylicacid 4-carbamimidoyl-benzylamide;

(6S)-1-chloro-8,8-dimethyl-4-oxo-3-(3-phenyl-propylamino)-4,6,7,8-tetrahydro-pyrrolo[1,2-a]pyrazine-6-carboxylic acid 4-carbamimidoyl-benzylamide;

(6S)-1-chloro-3-ethylamino-8,8-dimethyl-4-oxo-4,6,7,8-tetrahydro-pyrrolo[1,2-a]pyrazine-6-carboxylic acid 4-carbamimidoyl-benzylamide;

(6S)-1-chloro-3-isopropylamino-8,8-dimethyl-4-oxo-4,6,7,8-tetrahydro-pyrrolo[1,2-a]pyrazine-6-carboxylic acid 4-carbamimidoyl-benzylamide;

(6S)-1-chloro-8,8-dimethyl-3-methylamino-4-oxo-4,6,7,8-tetrahydro-pyrrolo[1,2-a]pyrazine-6-carboxylic acid 4-carbamimidoyl-benzylamide;

(6S)-1-chloro-8,8-dimethyl-4-oxo-3-phenethylamino-4,6,7,8-tetrahydro-pyrrolo[1,2-a]pyrazine-6-carboxylic acid 4-carbamimidoyl-benzylamide;

(6S)-1-chloro-3-[2-(4-hydroxy-phenyl)-ethylamino]-8,8-dimethyl-4-oxo-4,6,7,8-tetrahydro-pyrrolo[1,2-a]pyrazine-6-carboxylic acid 4-carbamimidoyl-benzylamide;

(6S)-3-amino-1-chloro-8,8-dimethyl-4-oxo-4,6,7,8-tetrahydro-pyrrolo[1,2-a]pyrazine-6-carboxylic acid 4-carbamimidoyl-benzylamide;

(6S)-1-chloro-3-methylamino-4-oxo-4,6,7,8-tetrahydro-pyrrolo[1,2-a]pyrazine-6-carboxylic acid 4-carbamimidoyl-benzylamide;

(6S)-1-chloro-3-isopropylamino-4-oxo-4,6,7,8-tetrahydro-pyrrolo[1,2-a]pyrazine-6-carboxylic acid 4-carbamimidoyl-benzylamide;

(6S)-1-chloro-3-ethylamino-4-oxo-4,6,7,8-tetrahydro-pyrrolo[1,2-a]pyrazine-6-carboxylic acid 4-carbamimidoyl-benzylamide;

(6S)-1-chloro-3-cyclobutylamino-8,8-diethyl-4-oxo-4,6,7,8-tetrahydro-pyrrolo[1,2-a]pyrazine-6-carboxylic acid 4-carbamimidoyl-benzylamide;

(6S)-1-chloro-3-cyclopropylamino-8,8-diethyl-4-oxo-4,6,7,8-tetrahydro-pyrrolo[1,2-a]pyrazine-6-carboxylic acid 4-carbamimidoyl-benzylamide;

(6S)-1-chloro-8,8-diethyl-3-ethylamino-4-oxo-4,6,7,8-tetrahydro-pyrrolo[1,2-a]pyrazine-6-carboxylic acid 4-carbamimidoyl-benzylamide;

(6S)-1-chloro-8,8-diethyl-3-isopropylamino-4-oxo-4,6,7,8-tetrahydro-pyrrolo[1,2-a]pyrazine-6-carboxylic acid 4-carbamimidoyl-benzylamide;

(6S)-1-chloro-8,8-diethyl-4-oxo-3-(3-phenyl-propylamino)-4,6,7,8-tetrahydro-pyrrolo[1,2-a]pyrazine-6-carboxylic acid 4-carbamimidoyl-benzylamide;

(6S, 8R)-1-chloro-8-methyl-4-oxo-3-(3-phenyl-propylamino)-8-propyl-4,6,7,8-tetrahydro-pyrrolo[1,2-a]pyrazine-6-carboxylic acid 4-carbamimidoyl-benzylamide;

(6S)-1-chloro-3-cyclobutylamino-4-oxo-8,8-dipropyl-4,6,7,8-tetrahydro-pyrrolo[1,2-a]pyrazine-6-carboxylic acid 4-carbamimidoyl-benzylamide;

(6S)-1-chloro-3-ethylamino-4-oxo-8,8-dipropyl-4,6,7,8-tetrahydro-pyrrolo[1,2-a]pyrazine-6-carboxylic acid 4-carbamimidoyl-benzylamide;

(6S, 8R)-1-chloro-3-cyclobutylamino-8-methyl-4-oxo-4,6,7,8-tetrahydro-pyrrolo[1,2-a]pyrazine-6,8-dicarboxylic acid 6-(4-carbamimidoyl-benzylamide) 8-methylamide;

(6S, 8R)-1-chloro-3-cyclobutylamino-8-methyl-4-oxo-4,6,7,8-tetrahydro-pyrrolo[1,2-a]pyrazine-6,8-dicarboxylic acid 8-benzylamide 6-(4-carbamimidoyl-benzylamide);

(6S, 8R)-1-chloro-3-cyclobutylamino-8-ethyl-4-oxo-4,6,7,8-tetrahydro-pyrrolo[1,2-a]pyrazine-6-carboxylic acid -4-carbamimidoyl-benzylamide;

(6S, 8R)-1-chloro-3-cyclobutylamino-8-ethyl-4-oxo-4,6,7,8-tetrahydro-pyrrolo[1,2-a]pyrazine-6-carboxylic acid (1-amino-isoquinolin-6-ylmethyl)-amide; and 1-chloro-3-cyclobutylamino-8-ethyl-4-oxo-4,6,7,8-tetrahydro-pyrrolo[1,2-a]pyrazine-6-carboxylic acid 4-aminomethyl-benzylamide;

or a stereoisomer or pharmaceutically acceptable salt form thereof.

5. A pharmaceutical composition comprising a pharmaceutically acceptable carrier and a therapeutically effective amount of a compound of claim 1 or a pharmaceutically acceptable salt form thereof.

6. A method of treating thomboembolic disorders which comprises administering to a host in need of such treatment a therapeutically effective amount of a compound of claim 1 or a pharmaceutically acceptable salt form thereof.

7. A method according to claim 6, wherein the thromboembolic disorder is selected from the group consisting of arterial cardiovascular thromboembolic disorders, venous cardiovascular thromboembolic disorders, and thromboembolic disorders in the chambers of the heart.

8. A method according to claim 6, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

9. A compound according to claim 3, wherein:
$R^3$ is selected from the group: Cl, Br, $NO_2$, CN, $CF_3$, and $CH_3$.

10. A pharmaceutical composition comprising a pharmaceutically acceptable carrier and a therapeutically effective amount of a compound of claim 2 or a pharmaceutically acceptable salt form thereof.

11. A method of treating thomboembolic disorders which comprises administering to a host in need of such treatment a therapeutically effective amount of a compound of claim 2 or a pharmaceutically acceptable salt form thereof.

12. A method according to claim 11, wherein the thromboembolic disorder is selected from the group consisting of arterial cardiovascular thromboembolic disorders, venous cardiovascular thromboembolic disorders, and thromboembolic disorders in the chambers of the heart.

13. A method according to claim 11, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

14. A pharmaceutical composition comprising a pharmaceutically acceptable carrier and a therapeutically effective amount of a compound of claim 3 or a pharmaceutically acceptable salt form thereof.

15. A method of treating thomboembolic disorders which comprises administering to a host in need of such treatment a therapeutically effective amount of a compound of claim 3 or a pharmaceutically acceptable salt form thereof.

16. A method according to claim 15, wherein the thromboembolic disorder is selected from the group consisting of arterial cardiovascular thromboembolic disorders, venous cardiovascular thromboembolic disorders, and thromboembolic disorders in the chambers of the heart.

17. A method according to claim 15, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

18. A pharmaceutical composition comprising a pharmaceutically acceptable carrier and a therapeutically effective amount of a compound of claim 4 or a pharmaceutically acceptable salt form thereof.

19. A method of treating thomboembolic disorders which comprises administering to a host in need of such treatment a therapeutically effective amount of a compound of claim 4 or a pharmaceutically acceptable salt form thereof.

20. A method according to claim 19, wherein the thromboembolic disorder is selected from the group consisting of arterial cardiovascular thromboembolic disorders, venous cardiovascular thromboembolic disorders, and thromboembolic disorders in the chambers of the heart.

21. A method according to claim 19, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

22. A pharmaceutical composition comprising a pharmaceutically acceptable carrier and a therapeutically effective amount of a compound of claim 9 or a pharmaceutically acceptable salt form thereof.

23. A method of treating thomboembolic disorders which comprises administering to a host in need of such treatment a therapeutically effective amount of a compound of claim 9 or a pharmaceutically acceptable salt form thereof.

24. A method according to claim 23, wherein the thromboembolic disorder is selected from the group consisting of arterial cardiovascular thromboembolic disorders, venous cardiovascular thromboembolic disorders, and thromboembolic disorders in the chambers of the heart.

25. A method according to claim 23, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

* * * * *